US008367621B2

(12) United States Patent
Ruoslahti et al.

(10) Patent No.: US 8,367,621 B2
(45) Date of Patent: Feb. 5, 2013

(54) METHODS AND COMPOSITIONS RELATED TO INTERNALIZING RGD PEPTIDES

(75) Inventors: Erkki Ruoslahti, Buellton, CA (US); Tambet Teesalu, Goleta, CA (US); Kazuki Sugahara, Goleta, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 674 days.

(21) Appl. No.: 12/355,672

(22) Filed: Jan. 16, 2009

(65) Prior Publication Data

US 2009/0246133 A1 Oct. 1, 2009

Related U.S. Application Data

(60) Provisional application No. 61/022,131, filed on Jan. 18, 2008.

(51) Int. Cl.
*A61K 38/08* (2006.01)
(52) U.S. Cl. ....... 514/21.6; 514/1.1; 514/21.1; 530/317; 530/328
(58) Field of Classification Search .................. None
See application file for complete search history.

(56) References Cited

U.S. PATENT DOCUMENTS

| 6,967,238 B2* | 11/2005 | Blaschuk et al. ........... 530/317 |
| 2002/0193295 A1* | 12/2002 | Calenoff et al. ............ 514/12 |
| 2005/0054563 A1 | 3/2005 | Desnoyer |
| 2006/0172941 A1 | 8/2006 | Rastelli |
| 2006/0239968 A1 | 10/2006 | Arap |
| 2007/0299043 A1 | 12/2007 | Hunter |
| 2009/0226372 A1 | 9/2009 | Ruoslahti |

FOREIGN PATENT DOCUMENTS

WO 2004/074432 * 9/2004

OTHER PUBLICATIONS

Allam et al. Cholera toxin triggers apoptosis in human lung cancer cell lines. Cancer Res 57:2615-2618 1997.
Arap, W., et al. Cancer treatment by targeted drug delivery to tumor vasculature in a mouse model. Science 279:377-380, 1998.
Arbeit et al. Progressive squamous epithelial neoplasia in K14-human papillomavirus type 16 transgenic mice. J Virol 68:4358-4368, 1994.
Arleth, L., et al. Detailed structure of hairy mixed micelles formed by phosphatidylcholine and PEGylated phospholipids in aqueous media. Langmuir 21:3279-3290, 2005.
Bardeesy, et al. Pancreatic cancer biology and genetics. Nature Rev Cancer 2:897-909, 2002.
Cheresh, D.A., et al. Biosynthetic and functional properties of an Arg-Gly-Asp-directed receptor involved in human melanoma cell attachment to vitronectin, fibrinogen, and von Willebrand factor. J Biol Chem 262:17703-1771, 1987.
Curnis, F., et al. Coupling tumor necrosis factor-$\alpha$ with $\alpha_v$ integrin ligands improves its antineoplastic activity. Cancer Res 64:565-571, 2004.
Drake et al. Assessing tumor growth and distribution in a model of prostate cancer metastasis using bioluminescence imaging. Clin Exp Metastasis 22:674-684, 2005.
Elicieri, B.P., et al. Adhesion events in angiogenesis. Curr Opin Cell Biol 13(5):563, 2001.
Falanga V et al. Wound bed score and its correlation with healing of chronic wounds. Dermatol Ther 19:383-90, 2006.
Fogal, V., et al. Mitochondrial/cell-surface protein p32/gC1qR as a molecular target in tumor cells and tomor stroma. Cancer Res 68: 7210-7218, 2008.
Folkman J. Angiogenesis. Annu Rev Med. 57:1-18, 2006.
Hagerdorn, Target molecules for anti-angiogenic therapy: from basic research to clinical trials. Crit Rev Oncol Hematol 34:89-110, 2000.
Hanahan, Heritable formation of pancreatic $\beta$-cell tumors in transgenic mice expressing recombinant insulin/simian virus 40 oncogenes. Nature 315:115-122, 1985.
Hoffman, J.A. et al. Progressive vascular changes in a transgenic mouse model of squamous cell carcinoma. Cancer Cell 4:383-391, 2003.
International Preliminary Report on Patentability and Written Opinion for PCT/US2009/031305 dated Jul. 20, 2010.
International Search Report for PCT/US2009/031305 mailed Mar. 10, 2010.
Jain, A.K., Vascular and interstitial barriers to delivery of therapuetic agents in tumors. Cancer Metastasis Rev 9:253-266, 1990.
Jarvinen, T., et al. Molecular changes in the vasculature of injured tissues. Am J Path 171:702-711, 2007.
Joyce, J.A., et al. Stage-specific vascular markers revealed by phage display in a mouse model of pancreatic islet turmorigenesis. Cancer Cell 4:p. 393-403, 2003.
Karmali, P.P., et al. Targeting of albumin-embedded paclitaxel nanoparticles to tumors. Nanomedicine 5:73-82, 2008.
Kirsch et al. Anti-angiogenic treatment strategies for malignant brain tumors. J Neurooncol 50:149-163, 2000.
Koivunen, E., et al. Phage libraries displaying cyclic peptides with different ring sizes: ligand specifications of the RGD-directed integrins. Biotechnology (NY) 13:265-270, 1995.
Koivunen, E., et al. Selection of peptides binding to the $\alpha_5\beta_1$-ingtegrin from phage display library. J Biol Chem 268:20205-20210, 1993.
Kolonin MG et al. Synchronous selection of homing peptides for multiple tissues by in vivo phage display. FASEB 20:979-81, 2006.
Kreitman, et al. Recombinant toxins containing human granulocyte-macrophage colony-stimulating factor and either pseudomonas exotoxin or diphteria toxin kill gastrointestinal cancer and leukemia cells. Blood 90:252-259, 1997.
aakkonen P, et al. Antitumore activity of a homing peptide that targets tumor lymphatics and tumor cells. PNAS 101:9381-6, 2004.

(Continued)

*Primary Examiner* — Anish Gupta
(74) *Attorney, Agent, or Firm* — Pabst Patent Group LLP

(57) ABSTRACT

Disclosed are compositions and methods useful for targeting tissue undergoing angiogenesis or to cells or tissue expressing $\alpha v$ integrins. The compositions and methods are based on peptide sequences that selectively bind to and home to tissue undergoing angiogenesis or to cells or tissue expressing $\alpha v$ integrins in animals. The disclosed targeting is useful for delivering therapeutic and detectable agents to tissue experiencing angiogenesis or to cells or tissue expressing $\alpha v$ integrins.

21 Claims, 26 Drawing Sheets

OTHER PUBLICATIONS

Laakkonen, P, et al. A tumor-homing peptide with a targetign specificity related to lymphatic vessels. Nature Med 8:751-755, 2002.

Liu, C., et al. In vivo interrogation of the molecular display of atherosclerotic lesion surfaces. American Journal of Pathology 163:1859-71, 2003.

Marin J, et al. Role of vascular nitric oxide physiological and pathological conditions. Pharmacol Ther 75:111-34, 1997.

Martin, et al. Cancer gene therapy by thyroid hormone-mediated expression of toxin genes. Cancer Res 60:3218-3224, 2000.

Murphy, E.T., et al. Nanoparticle-mediated drug delivery to tumor vasculature suppresses metastasis. Proc Nat Acad Sci USA 105:9343-9348, 2008.

Osborne, C.K. Targeting the epidermal growth factor receptor in breast cancer cell lines with a recombinant ligand fusion toxin (DAB389EGF). Cancer J Sci Am 2:175, 1996.

Pasqualini, et al., αv integrins as receptors for tumor targeting by circulating ligands. Nature Biotechnol 15:542-546, 1997.

Pellet-Many, C., et al. Neuropilins: structure, function and role in disease. Biochem J 411:211-226, 2008.

Pellinen, T., et al. Integrin traffic. J Cell Sci 119:3723-3731, 2006.

Pierschbacher, M.D., et al. Cell attachment activity of fibronectin can be duplicated by small synthetic fragments of the molecule. Nature 309:30-33, 1984.

Pilch, J., et al. Peptides selected for binding to clotted plasma accumulate in tumor stroma and wounds. Proc Natl Acad Sci USA 103:2800-2804, 2006.

Porkka, K., et al. A fragment of the HMGN2 protein homes to the nuclei of tumor cells and tumor endothelial cells in vivo. Proc Natl Acad Sci USA 99:7444-7449, 2002.

Rajotte D, et al. Molecular heterogeneity of the vascular endothelium revealed by in vivo phage display. J Clin Invest 102:430-7, 1998.

Ruoslahti E., et al. Specialization of tumour vasculature. Nature Reviews Cancer 2:83-90, 2002.

Ruoslahti, E. Drug targeting to specific vascular sites. Drug Discovery Today. 7:1138-1143, 2002.

Ruoslahti, E. RGD story: a personal account. A Landmark Essay. Matrix Biology 2:459-465, 2003.

Ruoslahti, E., et al. Vascular homing peptides with cell-penetrating properties. Current Pharmaceutical Design. Special Issue: Cell-penetrating Pe[ptides, Mechanisms and Applications. Executive Editor: Ulo Langel. 11:3655-3660, 2005.

Ruosllahti, E. Vascular zipcodes in angiogenesis and metastasis. Biochem Soc Transact 32:397-402, 2004.

Rusnak et al. The effects of the novel, reversible epidermal growth factor receptor/ErbB-2 tyrosine kinase inhibitor, GW2016, on the growth of human normal and tumor-derived cell lines in vitro and in vivo. Mol Cancer Ther 1:85-94, 2001.

Simberg, D., et al. Biomimetic amplification of nanoparticle homing to tumors. Proc Natl Acad Sci USA 104:932-936, 2007.

Singer Aj, et al. Cutaneous wound healing. NEJM 341:738-46, 1999.

Sipkins, D.A., et al. Detection of tumor angiogenesis in vivo by $\alpha_v\beta_3$-targeted magnetic resonance imaging. Nature Med 4:623-626, 1998.

Sugahara, K.N., et al. Chondroitin sulfate E fragments enhance CD44 cleavage and CD44 dependent motility in tumor cells. Cancer Res 68:7191-7199, 2008.

Sugahara, K.N., et al. Hyaluronan oligosaccharides induce CD44 cleavage and promote cell migration in CD44-expressing tumor cells. J Biol Chem 278:32259-32265, 2003.

Thomas, G. Furin at the cutting edge: From protein traffic to embryogenesis and disease. Nat Rev Mol Cell Biol 3:753-766, 2002.

Uhland, K., Matriptase and its putative role in cancer. Cell Mol Life Sci 63:2968-2978, 2006.

von Maltzahn, et al. In vivo tumor cell targeting with "click" nanoparticles. Bioconjug Chem 19:1570-1578, 2008.

White, et al. Antibody-targeted immunotherapy for treatment of malignancy. Annu Rev Med 52:125-141, 2001.

Yang, et al. A fluorescent orthotopic bone metasis model of human prostate cancer. Cancer Res 59:781-786, 1999.

Zhang et al. Lymphatic zip codes in premalignant lesions and tumors. Cancer Res 66:5696-5706, 2006.

Hong, et al., "Targeting neuropilin 1 as an antitumor strategy in lung cancer", Clinical. Cancer Res., 13(6): 4759-68 (2007).

Sugahara, et al., "Tissue penetrating delivery of compounds and nanoparticles into tumors", Cancer Cell 16(6):510-20 (2009).

Sugahara, et al. "Coadministration of a tumor-penetrating peptide enhances the efficacy of cancer drugs", Am. Assoc. Adv of Sci., 328(5981):1031-35 (2010).

Teesalu, et al., "C-end rule peptides mediate neuropilin-1-dependent cell, vascular and tissue penetration", PNAS, 106(38):16157-62 (2009).

Vander Kool, et al., "Structural basis for ligand and heparin binding to neuropilin B domains", PNAS, 104(15):6152-57 (2007).

International Search Report PCT/US2009/31305, mailed Mar. 10, 2010.

GenBank Accession No. Q1YF93 "CueR-like heavy metal response, transcription regulator", 1 page, Submitted Mar. 2006, first published May 2, 2006, accessed Aug. 24, 2011.

\* cited by examiner

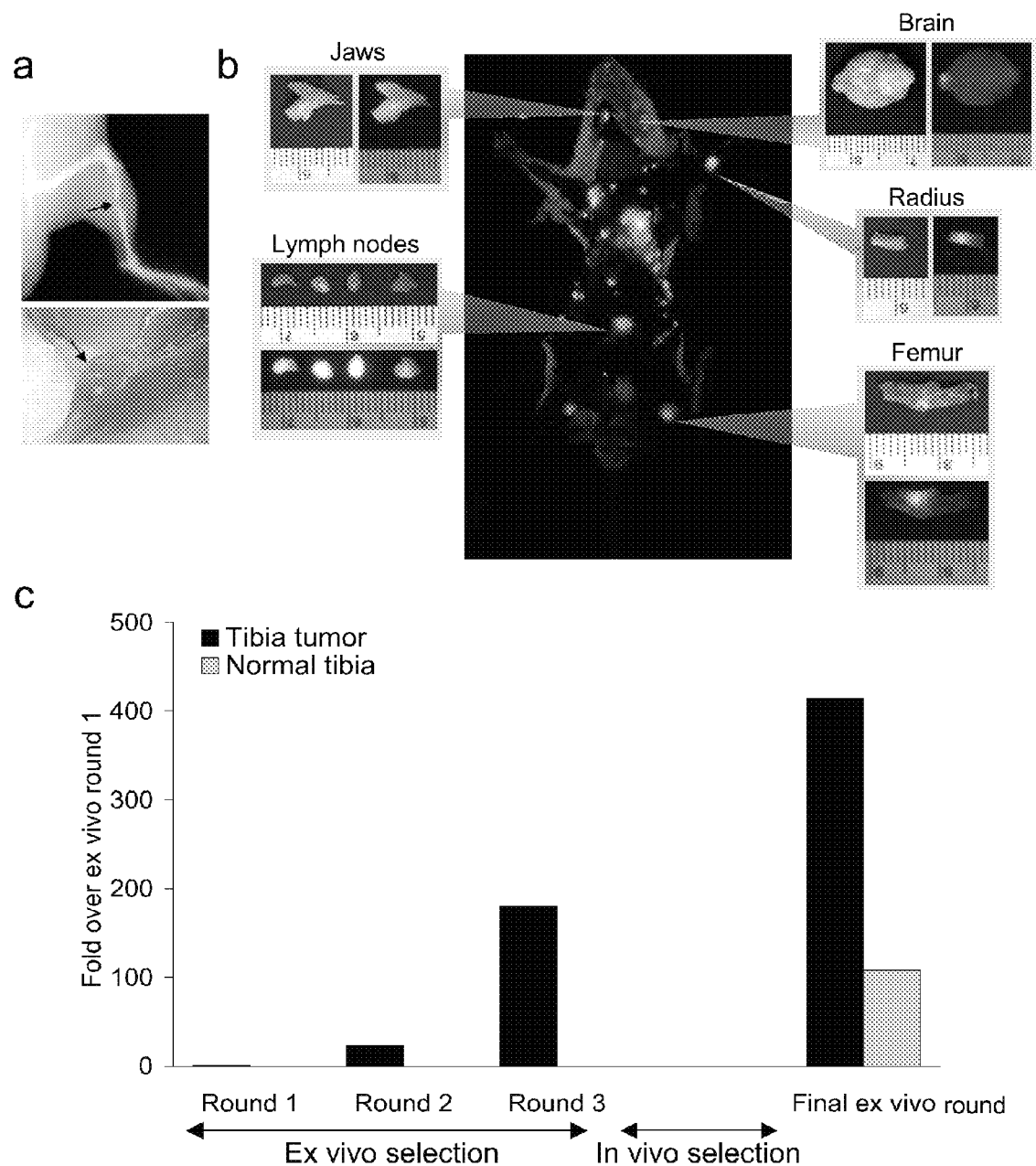

SEQUENCE LISTING

```
<160> NUMBER OF SEQ ID NOS: 330

<210> SEQ ID NO 1
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 1

Cys Arg Gly Asp Lys Gly Pro Asp Cys
1               5
```

```
<210> SEQ ID NO 2
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 2

Cys Arg Gly Asp Arg Gly Pro Asp Cys
1               5

<210> SEQ ID NO 3
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 3

Cys Arg Gly Asp Lys Gly Pro Glu Cys
1               5

<210> SEQ ID NO 4
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 4

Cys Asp Cys Arg Gly Asp Cys Phe Cys
1               5

<210> SEQ ID NO 5
<211> LENGTH: 6
<212> TYPE: PRT
<213> ORGANISM: Homo sapiens
<220> FEATURE:
<221> NAME/KEY: PEPTIDE
<222> LOCATION: (1)..(6)

<400> SEQUENCE: 5

Cys Arg Gly Asp Lys Gly
1               5

<210> SEQ ID NO 6
<211> LENGTH: 5
<212> TYPE: PRT
<213> ORGANISM: Homo sapiens
<220> FEATURE:
<221> NAME/KEY: PEPTIDE
<222> LOCATION: (1)..(5)

<400> SEQUENCE: 6

Cys Arg Gly Asp Lys
1               5

<210> SEQ ID NO 7
<211> LENGTH: 4
<212> TYPE: PRT
<213> ORGANISM: Homo sapiens
<220> FEATURE:
<221> NAME/KEY: PEPTIDE
<222> LOCATION: (1)..(4)
```

```
<400> SEQUENCE: 7

Cys Arg Gly Asp
1

<210> SEQ ID NO 8
<211> LENGTH: 3
<212> TYPE: PRT
<213> ORGANISM: Homo sapiens
<220> FEATURE:
<221> NAME/KEY: PEPTIDE
<222> LOCATION: (1)..(3)

<400> SEQUENCE: 8

Cys Arg Gly
1

<210> SEQ ID NO 9
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 9

Cys Lys Gly Asp Lys Gly Pro Asp Cys
1               5

<210> SEQ ID NO 10
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 10

Cys Asp Cys Arg Gly Asp Cys Phe Cys
1               5

<210> SEQ ID NO 11
<211> LENGTH: 4
<212> TYPE: PRT
<213> ORGANISM: Homo sapiens
<220> FEATURE:
<221> NAME/KEY: PEPTIDE
<222> LOCATION: (1)..(4)

<400> SEQUENCE: 11

Arg Gly Asp Lys
1

<210> SEQ ID NO 12
<211> LENGTH: 4
<212> TYPE: PRT
<213> ORGANISM: Homo sapiens
<220> FEATURE:
<221> NAME/KEY: PEPTIDE
<222> LOCATION: (1)..(4)

<400> SEQUENCE: 12

Arg Gly Asp Arg
1

<210> SEQ ID NO 13
<211> LENGTH: 4
<212> TYPE: PRT
<213> ORGANISM: Homo sapiens
```

```
<220> FEATURE:
<221> NAME/KEY: PEPTIDE
<222> LOCATION: (1)..(4)

<400> SEQUENCE: 13

Arg Xaa Xaa Lys
1

<210> SEQ ID NO 14
<211> LENGTH: 4
<212> TYPE: PRT
<213> ORGANISM: Homo sapiens
<220> FEATURE:
<221> NAME/KEY: PEPTIDE
<222> LOCATION: (1)..(4)

<400> SEQUENCE: 14

Arg Xaa Xaa Arg
1

<210> SEQ ID NO 15
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 15

Cys Arg Ser Thr Arg Ala Asn Pro Cys
1               5

<210> SEQ ID NO 16
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 16

Cys Ser Ser Val Ala Asn Glu Leu Cys
1               5

<210> SEQ ID NO 17
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 17

Cys Leu Pro Val Asn Gln Asn Cys
1               5

<210> SEQ ID NO 18
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 18

Cys Gly Asn Gly Ala Leu Asn Ile Cys
1               5
```

```
<210> SEQ ID NO 19
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 19

Cys Glu Val Gly Gln Asn Ala Ile Cys
1               5

<210> SEQ ID NO 20
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 20

Cys Gly Arg Gly Asp Ser Pro Asp Cys
1               5

<210> SEQ ID NO 21
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 21

Cys Gly Arg Gly Asp Ser Pro Asp Cys
1               5

<210> SEQ ID NO 22
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 22

Cys Gly Arg Gly Asp Ser Pro Asp Cys
1               5

<210> SEQ ID NO 23
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 23

Cys Asn Asn Glu Val Asn Ser Val Cys
1               5

<210> SEQ ID NO 24
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 24
```

```
Cys Glu Ala Glu Gly Leu Val Leu Cys
1               5
```

<210> SEQ ID NO 25
<211> LENGTH: 9
<212> TYPE: PRT
<213> ORGANISM: Homo sapiens
<220> FEATURE:
<221> NAME/KEY: peptide
<222> LOCATION: (1)..(9)

<400> SEQUENCE: 25

```
Cys Ala Ser Gly Glu Asn Gly Val Cys
1               5
```

<210> SEQ ID NO 26
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 26

```
Cys Pro Asp Gln Gly Leu Lys Phe Cys
1               5
```

<210> SEQ ID NO 27
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 27

```
Cys Asp Leu Met Ser Asn Glu Leu Cys
1               5
```

<210> SEQ ID NO 28
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 28

```
Ser Ser Val Asp Lys Leu Ala Ala Ala Leu Glu
1               5                   10
```

<210> SEQ ID NO 29
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 29

```
Cys Asp Asn Pro Phe Asp Pro Ser Cys
1               5
```

<210> SEQ ID NO 30
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)

<400> SEQUENCE: 30

Cys Arg Gly Gly Asn Glu Val Glu Cys
1               5

<210> SEQ ID NO 31
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 31

Cys Glu Ala Asp Gly Leu Ser Ile Cys
1               5

<210> SEQ ID NO 32
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 32

Cys Met Leu Asp Pro Ser Lys Pro Cys
1               5

<210> SEQ ID NO 33
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 33

Cys Glu Ser Pro Phe Glu Asp Asp Cys
1               5

<210> SEQ ID NO 34
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 34

Cys Gly Arg Gly Asp Ala Leu Pro Cys
1               5

<210> SEQ ID NO 35
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 35

Cys Thr Gly Asp Arg Arg Gly Asp Cys
1               5

<210> SEQ ID NO 36
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)

<400> SEQUENCE: 36

Cys Glu Arg Asp Gly Asn Asp Ile Cys
1               5

<210> SEQ ID NO 37
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 37

Cys Arg Gly Asp Lys Gly Glu Asn Cys
1               5

<210> SEQ ID NO 38
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 38

Cys Lys Lys Thr Gly Asn Arg Gly Cys
1               5

<210> SEQ ID NO 39
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 39

Cys Lys Ala Xaa Glu Asn His Ile Cys
1               5

<210> SEQ ID NO 40
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 40

Cys Thr Met Asp Gly Asn Glu Ile Cys
1               5

<210> SEQ ID NO 41
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 41

Cys Ser Asp Ser Leu Thr Val Cys
1               5
```

```
<210> SEQ ID NO 42
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 42

Cys Gly Arg Gly Asp Asn Leu Gln Cys
1               5

<210> SEQ ID NO 43
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 43

Cys Ala Asp Ser Thr Val Asp Gly Cys
1               5

<210> SEQ ID NO 44
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 44

Cys Arg Asn Asp Val Ser Ala Asp Cys
1               5

<210> SEQ ID NO 45
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 45

Cys Gly Thr Gly Asn Asn Met Val Cys
1               5

<210> SEQ ID NO 46
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 46

Cys Leu Lys Pro Pro Arg His Cys
1               5

<210> SEQ ID NO 47
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<400> SEQUENCE: 47

Cys Thr Pro Glu Gly Leu Thr Ile Cys
1               5

<210> SEQ ID NO 48
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 48

Cys Pro Met Asp Gly Asn Ser Ile Cys
1               5

<210> SEQ ID NO 49
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 49

Cys Gly Thr Gly Gly Asn Asn Val Cys
1               5

<210> SEQ ID NO 50
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 50

Cys Ala Asp Gln Thr Leu Thr Ile Cys
1               5

<210> SEQ ID NO 51
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 51

Cys Ser Met Asp Glu Asn Glu Leu Cys
1               5

<210> SEQ ID NO 52
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 52

Cys Lys Ala Asp Gly Leu Thr Val Cys
1               5

<210> SEQ ID NO 53
<211> LENGTH: 9
<212> TYPE: PRT
<213> ORGANISM: Homo sapiens
```

-continued

```
<220> FEATURE:
<221> NAME/KEY: PEPTIDE
<222> LOCATION: (1)..(9)

<400> SEQUENCE: 53

Cys Met Asn Asn Val Glu Met Asn Cys
1               5

<210> SEQ ID NO 54
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 54

Cys Val Ser Asn Asp Val Gly His Cys
1               5

<210> SEQ ID NO 55
<211> LENGTH: 10
<212> TYPE: PRT
<213> ORGANISM: Homo sapiens
<220> FEATURE:
<221> NAME/KEY: PEPTIDE
<222> LOCATION: (1)..(10)

<400> SEQUENCE: 55

Cys Lys Asn Gly Glu Ala Ser Gln Gly Cys
1               5                   10

<210> SEQ ID NO 56
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 56

Cys Gln Ser Asn Asp Ile Ala Thr Cys
1               5

<210> SEQ ID NO 57
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 57

Cys Arg Ser Thr Arg Ser Ser Pro Cys
1               5

<210> SEQ ID NO 58
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 58

Ala Arg Val Leu Arg Ser Gly Ser Ala Lys Leu Ala Ala Ala Leu Glu
1               5                   10                  15
```

```
<210> SEQ ID NO 59
<211> LENGTH: 10
<212> TYPE: PRT
<213> ORGANISM: Homo sapiens
<220> FEATURE:
<221> NAME/KEY: PEPTIDE
<222> LOCATION: (1)..(10)

<400> SEQUENCE: 59

Cys Ile Gln Asn Thr Asn Asn Ile Glu Cys
1               5                   10

<210> SEQ ID NO 60
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 60

Cys Gly Met Ser Gly Asn Glu Ile Cys
1               5

<210> SEQ ID NO 61
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 61

Cys Lys Pro Pro Arg Arg Ser Cys
1               5

<210> SEQ ID NO 62
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 62

Cys Asp Thr Lys Pro Pro Arg Cys
1               5

<210> SEQ ID NO 63
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 63

Cys Glu Leu Ala Ser Leu Thr Ile Cys
1               5

<210> SEQ ID NO 64
<211> LENGTH: 18
<212> TYPE: PRT
<213> ORGANISM: Homo sapiens
<220> FEATURE:
<221> NAME/KEY: PEPTIDE
<222> LOCATION: (1)..(18)

<400> SEQUENCE: 64
```

```
Cys Lys Pro Pro Gly Leu Ile Ala Lys Leu Ser Leu Arg Thr His Leu
1               5                   10                  15

Thr Ser

<210> SEQ ID NO 65
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 65

Cys Leu Thr Leu Cys Asp Tyr Cys
1               5

<210> SEQ ID NO 66
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 66

Cys Ser Gly Thr Ser Arg Gly Asp Cys
1               5

<210> SEQ ID NO 67
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 67

Cys Asp Gly Lys Gln Asn Arg Ala Cys
1               5

<210> SEQ ID NO 68
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 68

Cys Asp Leu Thr Gly Asn Asp Val Cys
1               5

<210> SEQ ID NO 69
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 69

Cys Arg Pro Pro Arg Arg Val Cys
1               5

<210> SEQ ID NO 70
<211> LENGTH: 8
<212> TYPE: PRT
<213> ORGANISM: Homo sapiens
```

```
<220> FEATURE:
<221> NAME/KEY: PEPTIDE
<222> LOCATION: (1)..(8)

<400> SEQUENCE: 70

Cys Asp Asn Leu Leu Pro Ala Cys
1               5

<210> SEQ ID NO 71
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 71

Cys Ser Leu Asn Asp Ile Cys
1               5

<210> SEQ ID NO 72
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 72

Cys Ala Ser Ala Gly Leu Val Val Cys
1               5

<210> SEQ ID NO 73
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 73

Cys Asn Pro Lys Pro Pro Arg Cys
1               5

<210> SEQ ID NO 74
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 74

Cys Met Asn Glu Val Asn Ala Lys Cys
1               5

<210> SEQ ID NO 75
<211> LENGTH: 6
<212> TYPE: PRT
<213> ORGANISM: Homo sapiens
<220> FEATURE:
<221> NAME/KEY: PEPTIDE
<222> LOCATION: (1)..(6)

<400> SEQUENCE: 75

Cys Thr Lys Pro Pro Arg
1               5
```

```
<210> SEQ ID NO 76
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 76

Ala Arg Gly Pro Arg Ile Ser Cys
1               5

<210> SEQ ID NO 77
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 77

Cys Glu Asn Gly Ser Leu Thr Leu Cys
1               5

<210> SEQ ID NO 78
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 78

Cys Asp Gly Asn Asn Ser Arg Cys
1               5

<210> SEQ ID NO 79
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 79

Cys Gly Lys Pro Ala Arg Lys Cys
1               5

<210> SEQ ID NO 80
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 80

Cys Glu Asn Arg Val Asp Gln Asp Cys
1               5

<210> SEQ ID NO 81
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 81
```

```
Cys Ser Lys Pro Pro Arg Gly Cys
1               5

<210> SEQ ID NO 82
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 82

Cys Val Lys Gln Lys Pro Leu Ile Cys
1               5

<210> SEQ ID NO 83
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 83

Cys Ser Lys Pro Pro Arg Ser Cys
1               5

<210> SEQ ID NO 84
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 84

Ala Arg Gly Pro Arg Ile Ser Cys
1               5

<210> SEQ ID NO 85
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 85

Cys Asn Asp Leu Ser Gly Cys
1               5

<210> SEQ ID NO 86
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 86

Cys Asp Thr Lys Pro Pro Arg Cys
1               5

<210> SEQ ID NO 87
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)

<400> SEQUENCE: 87

Cys Arg Gly Asp Lys Gly Pro Asp Cys
1               5

<210> SEQ ID NO 88
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 88

Cys Thr Asn Glu Ile Asn Gly Thr Cys
1               5

<210> SEQ ID NO 89
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 89

Cys Asp Ile Gly Ala Asn Met Val Cys
1               5

<210> SEQ ID NO 90
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 90

Cys Ser Lys Pro Pro Arg His Cys
1               5

<210> SEQ ID NO 91
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 91

Cys Arg Gly Asp Lys Gly Pro Asp Cys
1               5

<210> SEQ ID NO 92
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 92

Cys His Asp Gly Ser Leu Thr Val Cys
1               5

<210> SEQ ID NO 93
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)

<400> SEQUENCE: 93

Cys Ala Leu Glu Gly Asn Ala Val Cys
1               5

<210> SEQ ID NO 94
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 94

Cys Lys Lys Pro Tyr Lys Ser Cys
1               5

<210> SEQ ID NO 95
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 95

Cys Gly Val Asp Leu Asn Thr Ile Cys
1               5

<210> SEQ ID NO 96
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 96

Cys Ser Leu Ser Asn Asp Val Asp Cys
1               5

<210> SEQ ID NO 97
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 97

Cys Arg Gly Asp Lys Gly Pro Asp Cys
1               5

<210> SEQ ID NO 98
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 98

Cys Lys Asp Asn Asn Leu Ile Cys
1               5
```

```
<210> SEQ ID NO 99
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 99

Cys Ala Ser Asp Gly Leu Thr Val Cys
1               5

<210> SEQ ID NO 100
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 100

Cys Val Lys Pro Ala Arg Gly Cys
1               5

<210> SEQ ID NO 101
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 101

Cys Ser Ala Glu Gly Leu Val Val Cys
1               5

<210> SEQ ID NO 102
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 102

Cys Asn Glu Val Val Cys Arg Cys
1               5

<210> SEQ ID NO 103
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 103

Cys Leu Gly Asp Gly Val His Ile Cys
1               5

<210> SEQ ID NO 104
<211> LENGTH: 8
<212> TYPE: PRT
<213> ORGANISM: Homo sapiens
<220> FEATURE:
<221> NAME/KEY: PEPTIDE
<222> LOCATION: (1)..(8)
```

```
<400> SEQUENCE: 104

Cys Arg Pro Ala Arg Pro Leu Cys
1               5

<210> SEQ ID NO 105
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 105

Cys Ala Ser Asp Gly Leu Thr Val Cys
1               5

<210> SEQ ID NO 106
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 106

Cys Arg Gly Asp Lys Gly Val His Cys
1               5

<210> SEQ ID NO 107
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 107

Cys Thr Asp Gly Gly Leu Thr Val Cys
1               5

<210> SEQ ID NO 108
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 108

Cys Leu Val Ile Ser Gly Asp Ser Cys
1               5

<210> SEQ ID NO 109
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 109

Cys Gly Pro Asn Ser Leu Thr Val Cys
1               5

<210> SEQ ID NO 110
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)

<400> SEQUENCE: 110

Cys Asp Pro Arg Tyr Asp Asn Ala Cys
1               5

<210> SEQ ID NO 111
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 111

Cys Arg Ser Thr Arg Ser Ser Pro Cys
1               5

<210> SEQ ID NO 112
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 112

Cys Ser Thr Asp Ser Leu Thr Ile Cys
1               5

<210> SEQ ID NO 113
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 113

Cys Ser Asn Ala Gly Leu Thr Val Cys
1               5

<210> SEQ ID NO 114
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 114

Cys Ser Gly Gly Asp Asn Ala Cys
1               5

<210> SEQ ID NO 115
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 115

Cys Leu Gly Thr Gly Arg Gly Gly Cys
1               5
```

```
<210> SEQ ID NO 116
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 116

Cys Leu Ser Phe Glu Pro Cys Cys
1               5

<210> SEQ ID NO 117
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 117

Cys Gly Lys Pro Pro Arg Cys
1               5

<210> SEQ ID NO 118
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 118

Cys Lys Gly Gln Ser Leu Val Val Cys
1               5

<210> SEQ ID NO 119
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 119

Cys Arg Ser Thr Arg Asn Thr Glu Cys
1               5

<210> SEQ ID NO 120
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 120

Cys Asp Pro Ala Leu Asp Asn Ser Cys
1               5

<210> SEQ ID NO 121
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 121
```

Cys Arg Asp Asp Gly Ile Thr Ile Cys
1               5

<210> SEQ ID NO 122
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 122

Cys Arg Asp Asp Gly Ile Thr Ile Cys
1               5

<210> SEQ ID NO 123
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 123

Cys Pro Ala Gly Gly Leu Thr Val Cys
1               5

<210> SEQ ID NO 124
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 124

Cys Arg Glu Gly Ser Leu Thr Val Cys
1               5

<210> SEQ ID NO 125
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 125

Cys Arg Pro Pro Arg Ala Arg Cys
1               5

<210> SEQ ID NO 126
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 126

Cys Ala Ser Gly Lys Arg Gly Asp Cys
1               5

<210> SEQ ID NO 127
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)

<400> SEQUENCE: 127

Cys Ser Ala Asn Ser Leu Val Val Cys
1               5

<210> SEQ ID NO 128
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 128

Cys Glu Gly Glu Gly Leu Ile Leu Cys
1               5

<210> SEQ ID NO 129
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 129

Cys Asn Trp Ala Gly Asn Glu Val Cys
1               5

<210> SEQ ID NO 130
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 130

Cys Gly Ser Asp Gly Leu His Val Cys
1               5

<210> SEQ ID NO 131
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 131

Cys Val Gly Asp Gly Asn Ala Ile Cys
1               5

<210> SEQ ID NO 132
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 132

Cys Glu Gly Lys Asn Leu Thr Ile Cys
1               5

<210> SEQ ID NO 133
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)

<400> SEQUENCE: 133

Cys Ser Ala Ser Gly Gly Pro Arg Cys
1               5

<210> SEQ ID NO 134
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 134

Cys Gly Ser Asp Gly Leu Lys Ile Cys
1               5

<210> SEQ ID NO 135
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 135

Cys Arg Pro Pro Arg Gln His Cys
1               5

<210> SEQ ID NO 136
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 136

Cys Gly Glu Val Gly Ala Gly Thr Cys
1               5

<210> SEQ ID NO 137
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 137

Cys Arg Gly Asp Lys His Ala Asp Cys
1               5

<210> SEQ ID NO 138
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 138

Cys Asp Gly Ser Ser Leu Thr Val Cys
1               5
```

```
<210> SEQ ID NO 139
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 139

Cys Arg Pro Pro Arg Pro Asn Cys
1               5

<210> SEQ ID NO 140
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 140

Cys Gly Arg Gly Asp Lys Pro Gln Cys
1               5

<210> SEQ ID NO 141
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 141

Cys Gly Arg Gly Asp Met Pro Ser Cys
1               5

<210> SEQ ID NO 142
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 142

Cys Gly Ala Asp Gly Leu Thr Val Cys
1               5

<210> SEQ ID NO 143
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 143

Cys Gln Leu Asp Ser Leu Val Val Cys
1               5

<210> SEQ ID NO 144
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<400> SEQUENCE: 144

Cys Pro Ser Asn Ser Leu Thr Val Cys
1               5

<210> SEQ ID NO 145
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 145

Cys Val Gly Asp Gly Leu Gln Phe Cys
1               5

<210> SEQ ID NO 146
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 146

Cys Gly Pro Asp Ala Leu Val Leu Cys
1               5

<210> SEQ ID NO 147
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 147

Cys Asp Ala Glu Gly Leu Val Leu Cys
1               5

<210> SEQ ID NO 148
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 148

Cys Arg Gly Asp Lys Gly Pro Asp Cys
1               5

<210> SEQ ID NO 149
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 149

Cys Tyr Arg Lys Asn Glu Ile Glu Cys
1               5

<210> SEQ ID NO 150
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)

<400> SEQUENCE: 150

Cys Arg Gly Asp Lys Gly Val Gly Cys
1               5

<210> SEQ ID NO 151
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 151

Cys Asn Ser Leu Asn Ile Gly Ser Cys
1               5

<210> SEQ ID NO 152
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 152

Cys Lys Ser Asp Gly Leu Lys Ile Cys
1               5

<210> SEQ ID NO 153
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 153

Cys Ser Thr Arg Val Arg Ser Arg Cys
1               5

<210> SEQ ID NO 154
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 154

Cys Asp Gly Asn Gly Leu Asn Ile Cys
1               5

<210> SEQ ID NO 155
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 155

Cys Gly Arg Thr Glu Arg Lys Val Cys
1               5
```

```
<210> SEQ ID NO 156
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 156

Cys Gly Glu Asp Gly Leu Thr Val Cys
1               5

<210> SEQ ID NO 157
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 157

Cys Arg Gly Asp His Ala Ala Asn Cys
1               5

<210> SEQ ID NO 158
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 158

Cys Leu Val Phe Glu Ser Gly Lys Cys
1               5

<210> SEQ ID NO 159
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 159

Cys Arg Pro Thr Arg Ala Thr Asn Cys
1               5

<210> SEQ ID NO 160
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 160

Cys Glu Gly Thr Gly Leu Thr Ile Cys
1               5

<210> SEQ ID NO 161
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 161
```

Cys Met Asn Glu Gly Leu Thr Val Cys
1               5

<210> SEQ ID NO 162
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 162

Cys Ser Ala Asp Gly Leu Thr Val Cys
1               5

<210> SEQ ID NO 163
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 163

Cys Asp Gly Asn Gly Leu Thr Val Cys
1               5

<210> SEQ ID NO 164
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 164

Cys Ser Ala Asp Gly Leu Met Val Cys
1               5

<210> SEQ ID NO 165
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 165

Cys Glu Tyr Asp Ala Leu Thr Val Cys
1               5

<210> SEQ ID NO 166
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 166

Cys Cys Asp Lys Val Lys Thr Cys
1               5

<210> SEQ ID NO 167
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)

<400> SEQUENCE: 167

Cys Asn Ala Leu His Leu Glu Ser Cys
1               5

<210> SEQ ID NO 168
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 168

Cys Gly Arg Gly Asp Asp Lys Thr Cys
1               5

<210> SEQ ID NO 169
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 169

Cys Gly Ser Gly Gly Leu Thr Val Cys
1               5

<210> SEQ ID NO 170
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 170

Cys Pro Ser Asp Ser Leu Ala Leu Cys
1               5

<210> SEQ ID NO 171
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 171

Cys Asp Asn Gly Leu Val Leu Cys
1               5

<210> SEQ ID NO 172
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 172

Cys Arg Pro Thr Arg Asn Val Pro Cys
1               5

<210> SEQ ID NO 173
<211> LENGTH: 8
```

```
<212> TYPE: PRT
<213> ORGANISM: Homo sapiens
<220> FEATURE:
<221> NAME/KEY: PEPTIDE
<222> LOCATION: (1)..(8)

<400> SEQUENCE: 173

Cys Thr Lys Pro Pro Arg Gly Cys
1               5

<210> SEQ ID NO 174
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 174

Cys Met Gln Glu Gly Leu Asn Ile Cys
1               5

<210> SEQ ID NO 175
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 175

Cys Arg Gly Asp Ala Gly Ile Asn Cys
1               5

<210> SEQ ID NO 176
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 176

Cys Ser Arg Gly Ser Leu Lys Ile Cys
1               5

<210> SEQ ID NO 177
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 177

Cys Ala Thr Asn Ser Leu Thr Val Cys
1               5

<210> SEQ ID NO 178
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 178

Cys Gln Glu Thr Gly Leu Asn Ile Cys
1               5
```

```
<210> SEQ ID NO 179
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 179

Cys Arg Gly Asp Lys Gly Pro Glu Cys
1               5

<210> SEQ ID NO 180
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 180

Cys Glu Ile Gly Asp Asn Val Val Cys
1               5

<210> SEQ ID NO 181
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 181

Cys Gly Pro Gly Ala Leu Thr Val Cys
1               5

<210> SEQ ID NO 182
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 182

Cys Ala Ser Ser Gly Leu Thr Ile Cys
1               5

<210> SEQ ID NO 183
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 183

Cys Arg Gly Asp Ser Pro Leu Ser Cys Lys Leu Ala Ala Ala Leu Glu
1               5                   10                  15

<210> SEQ ID NO 184
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

<400> SEQUENCE: 184

Cys Met Ser Gly Thr Leu Thr Val Cys
1               5

<210> SEQ ID NO 185
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 185

Cys Leu Thr Phe Gly Lys Asp Lys Cys
1               5

<210> SEQ ID NO 186
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 186

Cys Val Gln Arg Pro Ala Arg Cys
1               5

<210> SEQ ID NO 187
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 187

Cys Asp Met Thr Ser Leu Thr Val Cys
1               5

<210> SEQ ID NO 188
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 188

Cys Gly Ser Gly Ser Leu Thr Val Cys
1               5

<210> SEQ ID NO 189
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 189

Cys Gly Arg Gly Asp Ala Phe Pro Cys
1               5

<210> SEQ ID NO 190
<211> LENGTH: 9
<212> TYPE: PRT
<213> ORGANISM: Homo sapiens

```
<220> FEATURE:
<221> NAME/KEY: PEPTIDE
<222> LOCATION: (1)..(9)

<400> SEQUENCE: 190

Cys Ala Ser Ser Ser Leu Thr Ile Cys
1               5

<210> SEQ ID NO 191
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 191

Cys Ala Ala Asn Pro Leu Val Leu Cys
1               5

<210> SEQ ID NO 192
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 192

Cys Arg Gly Asp Lys Gly Pro Glu Cys
1               5

<210> SEQ ID NO 193
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 193

Cys Leu Thr Ile Gly Gly Thr Ser Cys
1               5

<210> SEQ ID NO 194
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 194

Cys Glu Lys Arg Gly Asp Ser Leu Cys
1               5

<210> SEQ ID NO 195
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 195

Cys Ser Gly Lys Gly Leu Asn Ile Cys
1               5
```

```
<210> SEQ ID NO 196
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 196

Cys Ala Asp Asp Ala Leu Thr Phe Cys
 1               5

<210> SEQ ID NO 197
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 197

Cys Val Gly Ser Leu Thr Val Cys
 1               5

<210> SEQ ID NO 198
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 198

Cys Asn Ser Leu Asn Ile Gly Ser Cys
 1               5

<210> SEQ ID NO 199
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 199

Cys Asp Asp Glu Gly Leu Asn Leu Cys
 1               5

<210> SEQ ID NO 200
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 200

Cys Gly Ser Lys Ser Leu Val Leu Cys
 1               5

<210> SEQ ID NO 201
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 201
```

Cys Arg Gly Glu Glu Leu Thr Ile Cys
1               5

<210> SEQ ID NO 202
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 202

Cys Lys Asp Tyr Gly Ile Thr Val Cys
1               5

<210> SEQ ID NO 203
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 203

Cys Arg Gly Asp Lys Gly Pro Glu Cys
1               5

<210> SEQ ID NO 204
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 204

Cys Arg Thr Arg Ser Gly Gly Lys Cys
1               5

<210> SEQ ID NO 205
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 205

Ala Arg Val Leu Arg Ser Gly Ser Ala Lys Leu Ala Ala Ala Leu Glu
1               5                   10                  15

<210> SEQ ID NO 206
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 206

Cys Glu Val Gly Thr Arg Leu Asp Cys
1               5

<210> SEQ ID NO 207
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)

<400> SEQUENCE: 207

Cys Gly Arg Gly Asp Asn Leu Pro Cys
1               5

<210> SEQ ID NO 208
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 208

Cys Ser Leu Glu Asp Asn Ala Val Cys
1               5

<210> SEQ ID NO 209
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 209

Cys Met Ser Asp Gly Arg Asp Arg Cys
1               5

<210> SEQ ID NO 210
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 210

Cys Ser Asn Ala Pro Asn Lys Arg Cys
1               5

<210> SEQ ID NO 211
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 211

Ala Arg Gly Ser Leu Arg Val Ser Ala Lys Leu Ala Ala Ala Leu Glu
1               5                   10                  15

<210> SEQ ID NO 212
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 212

Cys Leu Arg Ser Asp Gly Ala Ser Cys
1               5

<210> SEQ ID NO 213
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)

<400> SEQUENCE: 213

Cys Leu Lys Asp Gly Arg Ser Ala Cys
1               5

<210> SEQ ID NO 214
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 214

Ser Ser Val Asp Lys Leu Ala Ala Ala Leu Glu
1               5                   10

<210> SEQ ID NO 215
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 215

Cys Leu Ala Asp Gly Arg Ala Lys Cys
1               5

<210> SEQ ID NO 216
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 216

Cys Leu Lys Asp Gly Arg Pro Ala Cys
1               5

<210> SEQ ID NO 217
<211> LENGTH: 13
<212> TYPE: PRT
<213> ORGANISM: Homo sapiens
<220> FEATURE:
<221> NAME/KEY: PEPTIDE
<222> LOCATION: (1)..(13)

<400> SEQUENCE: 217

Met Leu Gly Asp Pro Asn Pro Ala Arg Arg Val Gly
1               5                   10

<210> SEQ ID NO 218
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 218

Cys Ala Asn Ala Thr Tyr Glu Ala Cys
1               5
```

```
<210> SEQ ID NO 219
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 219

Cys Val Asp Ser Asn Asp Val Ser Cys
1               5

<210> SEQ ID NO 220
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 220

Cys Lys Gln Thr Arg Asn Thr Thr Cys
1               5

<210> SEQ ID NO 221
<211> LENGTH: 13
<212> TYPE: PRT
<213> ORGANISM: Homo sapiens
<220> FEATURE:
<221> NAME/KEY: PEPTIDE
<222> LOCATION: (1)..(13)

<400> SEQUENCE: 221

Met Leu Gly Asp Pro Asn Pro Ala Arg Arg Arg Val Gly
1               5                   10

<210> SEQ ID NO 222
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 222

Cys Asp Gly Val Val Leu Ser Cys
1               5

<210> SEQ ID NO 223
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 223

Cys Arg Gly Asp His Gly Val Glu Cys
1               5

<210> SEQ ID NO 224
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<400> SEQUENCE: 224

Cys Ser Glu Gln Gly Ile Thr Ile Cys
1               5

<210> SEQ ID NO 225
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 225

Cys Arg Ser Thr Arg Ser Lys Thr Cys
1               5

<210> SEQ ID NO 226
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 226

Cys Gly Lys Arg Gly Asp Ser Ile Cys
1               5

<210> SEQ ID NO 227
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 227

Ala Ser Arg Met Gly Gly Val Gly Ala Lys Leu Ala Ala Ala Leu Glu
1               5                   10                  15

<210> SEQ ID NO 228
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 228

Cys Arg Gly Asp Lys Gly Pro Asp Cys
1               5

<210> SEQ ID NO 229
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 229

Cys Glu Pro Thr Ala Lys Asn Asn Cys
1               5

<210> SEQ ID NO 230
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)

<400> SEQUENCE: 230

Cys Leu Asn Asp Gly Arg Pro Ala Cys
1               5

<210> SEQ ID NO 231
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 231

Cys Leu Leu Gly Ser Lys Asn Asp Cys
1               5

<210> SEQ ID NO 232
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 232

Cys Lys Ser Asn Pro Thr Gly Arg Cys
1               5

<210> SEQ ID NO 233
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 233

Ser Ser Val Asp Lys Leu Ala Ala Ala Leu Glu
1               5                   10

<210> SEQ ID NO 234
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 234

Cys Arg Gly Asp Lys Gly Pro Asp Cys
1               5

<210> SEQ ID NO 235
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 235

Cys Lys Ala Thr Arg Ser Thr Lys Cys
1               5
```

```
<210> SEQ ID NO 236
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 236

Cys Arg Gly Asp Arg Gly Pro Asp Cys
1               5

<210> SEQ ID NO 237
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 237

Cys Arg Gly Asp Lys Pro Leu Gly Cys
1               5

<210> SEQ ID NO 238
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 238

Cys Ile Asn Ser Pro Ser Ala Asp Cys
1               5

<210> SEQ ID NO 239
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 239

Cys Ser Arg Gly Gly Glu Asp Pro Cys
1               5

<210> SEQ ID NO 240
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 240

Cys Arg Gly Asp His Ala Gly Asp Cys
1               5

<210> SEQ ID NO 241
<211> LENGTH: 13
<212> TYPE: PRT
<213> ORGANISM: Homo sapiens
<220> FEATURE:
<221> NAME/KEY: PEPTIDE
<222> LOCATION: (1)..(13)

<400> SEQUENCE: 241
```

```
Ser Ser Val Asp Lys Leu Ser Thr Asp Tyr Thr Ala Asn
1               5                   10
```

<210> SEQ ID NO 242
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 242

```
Cys Thr Gly Arg Gly Asp Ala Leu Cys
1               5
```

<210> SEQ ID NO 243
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 243

```
Cys Pro Arg Asp Ser Asn Asn Val Cys
1               5
```

<210> SEQ ID NO 244
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 244

```
Ala Gly Leu Arg Gly Ser Ile Ser Ala Lys Leu Ala Ala Ala Leu Glu
1               5                   10                  15
```

<210> SEQ ID NO 245
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 245

```
Cys Val Arg Arg Gly Asp Ser Ala Cys
1               5
```

<210> SEQ ID NO 246
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 246

```
Cys Arg Gly Asp Arg Gly Pro Asp Cys
1               5
```

<210> SEQ ID NO 247
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)

<400> SEQUENCE: 247

Cys Lys Gly Ser Arg Asn Leu Asn Cys
1               5

<210> SEQ ID NO 248
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 248

Cys Gly Arg Gly Asp Asn Leu Ala Cys
1               5

<210> SEQ ID NO 249
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 249

Cys Arg Gln Val Ala Leu Gly Cys
1               5

<210> SEQ ID NO 250
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 250

Cys Ala Gln Ser Asn Arg Leu Asp Cys
1               5

<210> SEQ ID NO 251
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 251

Cys Glu Asn Trp Glu Lys Thr Ser Cys
1               5

<210> SEQ ID NO 252
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 252

Ser Gly Met Val Leu Arg Ser Ser Ala Lys Leu Ala Ala Ala Leu Glu
1               5                   10                  15

<210> SEQ ID NO 253
<211> LENGTH: 16
```

```
<212> TYPE: PRT
<213> ORGANISM: Homo sapiens
<220> FEATURE:
<221> NAME/KEY: PEPTIDE
<222> LOCATION: (1)..(16)

<400> SEQUENCE: 253

Ala Gly Arg Val Leu Arg Ser Ser Ala Lys Leu Ala Ala Ala Leu Glu
1               5                   10                  15

<210> SEQ ID NO 254
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 254

Cys Thr Pro His Ala His Pro Cys
1               5

<210> SEQ ID NO 255
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 255

Cys Arg Gly Asp Lys Gly Pro Asp Cys
1               5

<210> SEQ ID NO 256
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 256

Cys Arg Gly Asp Lys Gly Pro Asp Cys
1               5

<210> SEQ ID NO 257
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 257

Ala Gly Arg Val Leu Arg Ser Ser Ala Lys Leu Ala Ala Ala Leu Glu
1               5                   10                  15

<210> SEQ ID NO 258
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 258

Ala Gly Arg Val Leu Arg Ser Ser Ala Lys Leu Ala Ala Ala Leu Glu
1               5                   10                  15
```

<210> SEQ ID NO 259
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 259

Ala Gly Gly Gly Val Arg Ser Leu Ala Lys Leu Ala Ala Ala Leu Glu
1               5                   10                  15

<210> SEQ ID NO 260
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 260

Cys Arg Gly Asp Lys Gly Pro Asp Cys
1               5

<210> SEQ ID NO 261
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 261

Cys Arg Gly Asp Lys Ala Val Gly Cys
1               5

<210> SEQ ID NO 262
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 262

Cys Arg Gly Asp Arg Gly Val His Cys
1               5

<210> SEQ ID NO 263
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 263

Cys Leu Gly Asp Gly Arg Ala Lys Cys
1               5

<210> SEQ ID NO 264
<211> LENGTH: 9
<212> TYPE: PRT
<213> ORGANISM: Homo sapiens
<220> FEATURE:
<221> NAME/KEY: PEPTIDE
<222> LOCATION: (1)..(9)

```
<400> SEQUENCE: 264

Cys Val Val Gly Val Ser Arg Lys Cys
1               5

<210> SEQ ID NO 265
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 265

Cys Glu Lys Arg Gly Asp Asn Leu Cys
1               5

<210> SEQ ID NO 266
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 266

Ser Ser Val Asp Lys Leu Ala Ala Ala Leu Glu
1               5                   10

<210> SEQ ID NO 267
<211> LENGTH: 13
<212> TYPE: PRT
<213> ORGANISM: Homo sapiens
<220> FEATURE:
<221> NAME/KEY: PEPTIDE
<222> LOCATION: (1)..(13)

<400> SEQUENCE: 267

Met Leu Gly Asp Pro Asn Pro Ala Arg Arg Arg Val Gly
1               5                   10

<210> SEQ ID NO 268
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 268

Cys Gln Leu Leu Val Val Ser Cys
1               5

<210> SEQ ID NO 269
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 269

Ala Arg Val Ser Leu Arg Gly Ser Ala Lys Leu Ala Ala Ala Leu Glu
1               5                   10                  15

<210> SEQ ID NO 270
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)

<400> SEQUENCE: 270

Cys Arg Gly Asp Lys Gly Pro Glu Cys
1               5

<210> SEQ ID NO 271
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 271

Cys Arg Ser Asp Arg Trp Phe Cys
1               5

<210> SEQ ID NO 272
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 272

Cys Leu Pro Gly Ser Asp Ala Lys Cys
1               5

<210> SEQ ID NO 273
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 273

Cys Glu Lys Arg Gly Asp Ser Val Cys
1               5

<210> SEQ ID NO 274
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 274

Cys Gly Gly Ser Lys Lys Leu Ala Cys
1               5

<210> SEQ ID NO 275
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 275

Cys Arg Gly Asp His Ala Gly Asp Cys
1               5
```

```
<210> SEQ ID NO 276
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 276

Cys Arg Gly Asp Lys Thr Thr Asn Cys
1               5

<210> SEQ ID NO 277
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 277

Cys Arg Ala Ser Gly Ala Lys Lys Cys
1               5

<210> SEQ ID NO 278
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 278

Cys Gly Val Ala Pro Arg Asp Lys Cys
1               5

<210> SEQ ID NO 279
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 279

Ser Ser Val Asp Lys Leu Ala Ala Ala Leu Glu
1               5                   10

<210> SEQ ID NO 280
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 280

Cys Ser Gly Arg Gly Asp Ser Leu Cys
1               5

<210> SEQ ID NO 281
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 281
```

Cys Ala Asn Ala Asp Arg Val Thr Cys
1               5

<210> SEQ ID NO 282
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 282

Cys Glu Lys Arg Gly Asp Ser Val Cys
1               5

<210> SEQ ID NO 283
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 283

Ser Gly Met Val Leu Arg Ser Ser Ala Lys Leu Ala Ala Ala Leu Glu
1               5                   10                  15

<210> SEQ ID NO 284
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 284

Cys Arg Gly Asp Arg Gly Pro Asp Cys
1               5

<210> SEQ ID NO 285
<211> LENGTH: 15
<212> TYPE: PRT
<213> ORGANISM: Homo sapiens
<220> FEATURE:
<221> NAME/KEY: PEPTIDE
<222> LOCATION: (1)..(15)

<400> SEQUENCE: 285

Ala Val Arg Val Gly Val Arg Ala Lys Leu Ala Ala Ala Leu Glu
1               5                   10                  15

<210> SEQ ID NO 286
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 286

Cys Arg Gly Asp Ser Ala Cys
1               5

<210> SEQ ID NO 287
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)

<400> SEQUENCE: 287

Cys Gly Asn Glu Ile Ala Asp Lys Cys
1               5

<210> SEQ ID NO 288
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 288

Cys Glu Glu Gly Arg Arg Cys
1               5

<210> SEQ ID NO 289
<211> LENGTH: 16
<212> TYPE: PRT
<213> ORGANISM: Homo sapiens
<220> FEATURE:
<221> NAME/KEY: PEPTIDE
<222> LOCATION: (1)..(16)

<400> SEQUENCE: 289

Ala Gly Val Arg Met Gly Arg Gly Ala Lys Leu Ala Ala Ala Leu Glu
1               5                   10                  15

<210> SEQ ID NO 290
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 290

Cys Arg Gly Asp Arg Gly Pro Glu Cys
1               5

<210> SEQ ID NO 291
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 291

Cys Arg Gly Glu Lys Gly Pro Asp Cys
1               5

<210> SEQ ID NO 292
<211> LENGTH: 5
<212> TYPE: PRT
<213> ORGANISM: Homo sapiens
<220> FEATURE:
<221> NAME/KEY: PEPTIDE
<222> LOCATION: (1)..(5)

<400> SEQUENCE: 292

Cys Arg Gly Asp Cys
1               5

<210> SEQ ID NO 293
<211> LENGTH: 7
```

```
<212> TYPE: PRT
<213> ORGANISM: Homo sapiens
<220> FEATURE:
<221> NAME/KEY: PEPTIDE
<222> LOCATION: (1)..(7)

<400> SEQUENCE: 293

Arg Gly Asp Cys Cys Cys Cys
1               5

<210> SEQ ID NO 294
<211> LENGTH: 4
<212> TYPE: PRT
<213> ORGANISM: Homo sapiens
<220> FEATURE:
<221> NAME/KEY: PEPTIDE
<222> LOCATION: (1)..(4)

<400> SEQUENCE: 294

Lys Xaa Xaa Arg
1

<210> SEQ ID NO 295
<211> LENGTH: 4
<212> TYPE: PRT
<213> ORGANISM: Homo sapiens
<220> FEATURE:
<221> NAME/KEY: PEPTIDE
<222> LOCATION: (1)..(4)

<400> SEQUENCE: 295

Lys Xaa Xaa Lys
1

<210> SEQ ID NO 296
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 296

Arg Pro Ala Arg Pro Ala Arg
1               5

<210> SEQ ID NO 297
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 297

Arg Pro Ala Arg Pro Ala Arg Ala
1               5

<210> SEQ ID NO 298
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 298

Cys Arg Gly Asp Gly Gly Pro Asp Cys
1               5
```

```
<210> SEQ ID NO 299
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 299

Cys Gly Asn Lys Arg Thr Arg Gly Cys
1               5

<210> SEQ ID NO 300
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 300

Cys Arg Gly Asp Lys Arg Gly Pro Asp Glu Cys
1               5                   10

<210> SEQ ID NO 301
<211> LENGTH: 5
<212> TYPE: PRT
<213> ORGANISM: Homo sapiens
<220> FEATURE:
<221> NAME/KEY: PEPTIDE
<222> LOCATION: (1)..(5)

<400> SEQUENCE: 301

Cys Arg Asp Gly Cys
1               5

<210> SEQ ID NO 302
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 302

Cys Arg Asp Gly Lys Gly Pro His Cys
1               5

<210> SEQ ID NO 303
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 303

Cys Arg Asp Gly Arg Gly Pro His Cys
1               5

<210> SEQ ID NO 304
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<400> SEQUENCE: 304

Cys Ala Gly Asp Lys Gly Pro Asp Cys
1               5

<210> SEQ ID NO 305
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 305

Cys Arg Ala Asp Lys Gly Pro Asp Cys
1               5

<210> SEQ ID NO 306
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 306

Cys Arg Gly Ala Lys Gly Pro Asp Cys
1               5

<210> SEQ ID NO 307
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 307

Cys Arg Gly Asp Ala Gly Pro Asp Cys
1               5

<210> SEQ ID NO 308
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 308

Cys Arg Gly Asp Lys Ala Pro Asp Cys
1               5

<210> SEQ ID NO 309
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 309

Cys Arg Gly Asp Lys Gly Ala Asp Cys
1               5

<210> SEQ ID NO 310
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)

<400> SEQUENCE: 310

Cys Arg Gly Asp Lys Gly Pro Ala Cys
1               5

<210> SEQ ID NO 311
<211> LENGTH: 5
<212> TYPE: PRT
<213> ORGANISM: Homo sapiens
<220> FEATURE:
<221> NAME/KEY: PEPTIDE
<222> LOCATION: (1)..(5)

<400> SEQUENCE: 311

Cys Arg Gly Asp Arg
1               5

<210> SEQ ID NO 312
<211> LENGTH: 4
<212> TYPE: PRT
<213> ORGANISM: Homo sapiens
<220> FEATURE:
<221> NAME/KEY: PEPTIDE
<222> LOCATION: (1)..(4)

<400> SEQUENCE: 312

Gly Pro Asp Cys
1

<210> SEQ ID NO 313
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 313

Cys Arg Gly Asp His Gly Pro Asp Cys
1               5

<210> SEQ ID NO 314
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 314

Cys Arg Gly Asp His Gly Pro Glu Cys
1               5

<210> SEQ ID NO 315
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 315

Cys Arg Gly Asp His Gly Pro His Cys
1               5
```

```
<210> SEQ ID NO 316
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 316

Cys Arg Gly Asp His Gly Val Asp Cys
1               5

<210> SEQ ID NO 317
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 317

Cys Arg Gly Asp His Gly Val Glu Cys
1               5

<210> SEQ ID NO 318
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 318

Cys Arg Gly Asp His Gly Val His Cys
1               5

<210> SEQ ID NO 319
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 319

Cys Arg Gly Asp Lys Gly Val Asp Cys
1               5

<210> SEQ ID NO 320
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 320

Cys Arg Gly Asp Lys Gly Val Glu Cys
1               5

<210> SEQ ID NO 321
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 321
```

Cys Arg Gly Asp Lys Gly Val His Cys
1               5

<210> SEQ ID NO 322
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 322

Cys Arg Gly Asp Arg Gly Val Asp Cys
1               5

<210> SEQ ID NO 323
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 323

Cys Arg Gly Asp Arg Gly Val Glu Cys
1               5

<210> SEQ ID NO 324
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 324

Cys Arg Gly Asp Arg Gly Val His Cys
1               5

<210> SEQ ID NO 325
<211> LENGTH: 6
<212> TYPE: PRT
<213> ORGANISM: Homo sapiens
<220> FEATURE:
<221> NAME/KEY: PEPTIDE
<222> LOCATION: (1)..(6)

<400> SEQUENCE: 325

Arg Gly Asp Arg Lys His
1               5

<210> SEQ ID NO 326
<211> LENGTH: 12
<212> TYPE: PRT
<213> ORGANISM: Homo sapiens
<220> FEATURE:
<221> NAME/KEY: PEPTIDE
<222> LOCATION: (1)..(12)

<400> SEQUENCE: 326

Cys Arg Gly Asp Arg Lys His Gly Pro Asp His Cys
1               5                   10

<210> SEQ ID NO 327
<211> LENGTH: 13
<212> TYPE: PRT
<213> ORGANISM: Homo sapiens
<220> FEATURE:
<221> NAME/KEY: PEPTIDE

```
<222> LOCATION: (1)..(13)

<400> SEQUENCE: 327

Cys Arg Gly Asp Arg Lys His Gly Pro Asp Glu His Cys
1               5                   10

<210> SEQ ID NO 328
<211> LENGTH: 14
<212> TYPE: PRT
<213> ORGANISM: Homo sapiens
<220> FEATURE:
<221> NAME/KEY: PEPTIDE
<222> LOCATION: (1)..(14)

<400> SEQUENCE: 328

Cys Arg Gly Asp Arg Lys His Gly Pro Val Asp Glu His Cys
1               5                   10

<210> SEQ ID NO 329
<211> LENGTH: 9
<212> TYPE: PRT
<213> ORGANISM: Homo sapiens
<220> FEATURE:
<221> NAME/KEY: MISC
<222> LOCATION: (5)..(5)
<223> OTHER INFORMATION: X can be arginine, lysine, or histidine
<220> FEATURE:
<221> NAME/KEY: MISC
<222> LOCATION: (8)..(8)
<223> OTHER INFORMATION: X can be aspartic acid, glutamic acid, or
      histidine

<400> SEQUENCE: 329

Cys Arg Gly Asp Xaa Gly Val Xaa Cys
1               5

<210> SEQ ID NO 330
<211> LENGTH: 9
<212> TYPE: PRT
<213> ORGANISM: Homo sapiens
<220> FEATURE:
<221> NAME/KEY: MISC
<222> LOCATION: (8)..(8)
<223> OTHER INFORMATION: X can be aspartic acid, glutamic acid, or
      histidine

<400> SEQUENCE: 330

Cys Arg Gly Asp His Gly Pro Xaa Cys
1               5
```

METHODS AND COMPOSITIONS RELATED TO INTERNALIZING RGD PEPTIDES

CROSS-REFERENCE TO RELATED APPLICATIONS

This application claims benefit of U.S. Provisional Application No. 61/022,131, filed Jan. 18, 2008. Application No. 61/022,131, filed Jan. 18, 2008, is hereby incorporated herein by reference in its entirety.

STATEMENT REGARDING FEDERALLY SPONSORED RESEARCH

This invention was made with government support under grants CA104898, CA 119414, CA 119335, CA124427, CA115410, and 30199 from the National Cancer Institute of the NIH and grant BC 076050 from the Department of Defense. The government has certain rights in the invention.

REFERENCE TO SEQUENCE LISTING

The Sequence Listing submitted Aug. 1, 2011 as a text file named "SBMRI_36_8402_Updated_Sequence_Listing.txt," created on Jul. 20, 2011, and having a size of 64,958 bytes is hereby incorporated by reference pursuant to 37 C.F.R. §1.52(e)(5).

FIELD OF THE INVENTION

The present invention relates generally to the fields of molecular medicine, oncology, and vascular biology, more specifically, to integrin-binding peptides containing the RGD sequence that selectively home to tumors and sites of angiogenesis.

BACKGROUND OF THE INVENTION

The RGD (arginine-glycine-aspartic acid) is a key recognition sequence of cell surface receptors in many cell adhesion-promoting extracellular matrix proteins, including fibronectin, vitronectin, laminin, some collagens, and many others (Ruoslahti, 2003). Integrins, a large family of cell surface receptors, bind to extracellular matrix at the RGD sequence. Roughly one third of integrins use the RGD sequence as their recognition site; the others recognize other sequences. The RGD sequence also mediates the binding of platelets to fibrinogen in blood clotting. RGD peptides and peptidomimetics can be used to modulate integrin activity. These compounds are also useful in delivering therapeutic and diagnostic compounds to sites where integrins are active. A vast drug discovery effort centers on the RGD and related peptides and a number of RGD-based drugs are already on the market or in clinical trials (Ruoslahti, 2003; 2004).

Tumors, tissue regeneration, and inflammation induce the growth of new blood vessels from pre-existing ones. This process, angiogenesis, is a vital requirement for wound healing as the formation of new blood vessels allows a variety of mediators nutrients, and oxygen to reach the healing tissue (Marin 1997, Singer & Clark 1999, Falanga 2006, Folkman 2006). Newly formed blood vessels differ in structure from preexisting vasculature. Such differences have been extensively characterized by comparing tumor vasculature to normal vessels (Ruoslahti, 2002). Angiogenic vessels in non-malignant tissues and in pre-malignant lesions share markers with tumor vessels, but distinct markers also exist (Hoffman et al., 2003; Joyce et al., 2003).

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life. Thus, there is a need for new therapeutic strategies for selectively targeting tumors to increase the efficacy of diagnosis and treatment, and to reduce the side effects associated with systemic therapy. The present invention satisfies this need by providing molecules that selectively home to tumors, and which are suitable for selectively targeting drugs, gene therapy vectors or other agents to the appropriate tissue. Related advantages also are provided.

BRIEF SUMMARY OF THE INVENTION

Disclosed herein is an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions. The peptide can have a length of less than 100, 50, or 20 residues. The amino acid segment can be cyclic, such as via a disulfide bond. The peptide can selectively home to a site of angiogenesis, a site of injury, a surgical site, a tumor, a site of arthritis, or a cell or tissue expressing one or more αv integrins, neuropilin-1, or both. For example, the cell or tissue can be expressing one or more αv integrins or the cell or tissue can be expressing one or more αv integrins and neuropilin-1. The integrin can be, for example, αvβ3 integrin, αvβ5 integrin, α5β1 integrin, or a combination. In some forms, the amino acid segment can comprise the amino acid sequence RGD(R/K/H) (SEQ ID NO:325). For example, the amino acid segment can comprise the amino acid sequence CRGD(R/K/H)GP(D/H)C (SEQ ID NO:326). As another example, the amino acid segment can comprise the amino acid sequence CRGD(R/K/H)GP(D/E/H)C (SEQ ID NO:327). As another example, the amino acid segment can comprise the amino acid sequence CRGD(R/K/H)G(P/V)(D/E/H)C (SEQ ID NO:328). Thus, for example, the amino acid segment can comprise the amino acid sequence CRGDHGPDC (SEQ ID NO:313), CRGDHGPEC (SEQ ID NO:314), CRGDHGPHC (SEQ ID NO:315), CRGDHGVDC (SEQ ID NO:316), CRGDHGVEC (SEQ ID NO:317), CRGDHGVHC (SEQ ID NO:318), CRGDKGPDC (SEQ ID NO:1), CRGDKGPEC (SEQ ID NO:3), CRGDKGPHC (SEQ ID NO:302), CRGDKGVDC (SEQ ID NO:319), CRGDKGVEC (SEQ ID NO:320), CRGDKGVHC (SEQ ID NO:321), CRGDRGPDC (SEQ ID NO:2), CRGDRGPEC (SEQ ID NO:290), CRGDRGPHC (SEQ ID NO:303), CRGDRGVDC (SEQ ID

NO:322), CRGDRGVEC (SEQ ID NO:323), OR CRGDRGVHC (SEQ ID NO:324).

Also disclosed herein is a conjugate, wherein the conjugate comprises a moiety linked to an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions. The moiety can be an anti-angiogenic agent, a pro-angiogenic agent, a cancer chemotherapeutic agent, a cytotoxic agent, an anti-inflammatory agent, an anti-arthritic agent, a nanoparticle, a polypeptide, a nucleic acid molecule, a small molecule, a fluorophore, fluorescein, rhodamine, a radionuclide, indium-111, technetium-99, carbon-11, carbon-13, or a combination. The moiety can be a therapeutic agent, such as decorin. The moiety can also be a detectable agent. The conjugate can comprise a virus, such as a phage. Further disclosed is a method of directing a moiety to angiogenesis, comprising administering to the subject a conjugate, wherein the conjugate comprises a moiety linked to an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions. The moiety is used to treat cancer, diabetic blindness, age-related macular degeneration, rheumatoid arthritis, or psoriasis, or promote wound healing. The conjugate can have a therapeutic effect, such as that comprising a reduction in inflammation, an increase in speed of wound healing, a reduction in amounts of scar tissue, decrease in pain, decrease in swelling, or decrease in necrosis. The subject can have one or more sites to be targeted, wherein the moiety is directed to one or more of the sites to be targeted. The subject can have cancer, wherein the moiety is directed to tumor angiogenesis in the subject. For example, the conjugate can have a therapeutic effect on the cancer. For example, the size of a tumor can be reduced, or the growth of a tumor can be reduced, stopped or reversed. The moiety can also be used to detect the cancer, visualize one or more tumors, or both.

Also disclosed is a method of directing a moiety to a tumor, comprising administering to the subject the conjugate, wherein the conjugate comprises a moiety linked to an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions. The method can further comprise determining if a tumor in the subject expresses one or more αv integrins, neuropilin-1, or both, and if the tumor expresses one or more αv integrins, neuropilin-1, or both, administering the conjugate to the subject. For example, the tumor can be expressing one or more αv integrins or the tumor can be expressing one or more αv integrins and neuropilin-1. The method can further comprise determining if a tumor in the subject expresses neuropilin-1 at a level higher than normal, and if the tumor expresses neuropilin-1 at a level higher than normal, administering the conjugate to the subject. The cells in the tumor can express a αv integrin. The cells in the tumor can express neuropilin-1. The cells in the tumor can express neuropilin-2. The cells in the tumor can express neuropilin-1, neuropilin-2, or both. The cells in the tumor can express a αv integrin and neuropilin-1. The cells in the tumor can express neuropilin-1 at a level higher than normal. The integrin can be, for example, αvβ3 integrin, αvβ5 integrin, α5β1 integrin, or a combination.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

iRGD phage binding without inhibitors was considered as 100% in a. n=3; error bars, s.d.; single asterisk, p<0.05; double asterisk, p<0.01; triple asterisk, p<0.001.

FIGS. 14A-14E show CendR motif in iRGD internalization within tumor cells. a, The internalization of trypsin-treated iRGD phage within PPC1 cells pre-treated or not with non-infectious RPARPAR (SEQ ID NO:296) or RPARPARA (SEQ ID NO:297) phage. b, Inhibition of CRGDK (SEQ ID NO:6) phage binding to PPC1 by synthetic CRGDK (SEQ ID N:6), RPARPAR (SEQ ID NO:296), and RPARPARA (SEQ ID NO:297) peptides, and corresponding non-infectious phage. c, CRGDK (SEQ ID NO:6) phage binding to PPC1 cells treated with anti-neuropilin-1 blocking antibodies (anti-NRP-1) or control goat-IgG (left panel), and M21 cells transfected with neuropilin-1 cDNA to induce forced expression of neuropilin-1 (NRP-1), vector alone, or without transfection (right panel). d, Inhibition of iRGD and iRGE phage internalization within PPC1 by non-infectious phage displaying the CendR-internalizing peptides RPARPAR (SEQ ID NO:296) and CRGDK (SEQ ID NO:6). e, Dose-dependent inhibition of iRGD phage internalization within PPC1 cells by anti-neuropilin-1 antibodies (anti-NRP-1) to block neuropilin-1 function. Statistical analyses were performed with ANOVA (a, b, d) or Student's t-test (c, e). CRGDK (SEQ ID NO:6) phage binding without inhibitors was considered as 100% in b. n=3; error bars, s.d.; single asterisk, p<0.05; double asterisk, p<0.01; triple asterisk, p<0.001.

Figure 15:
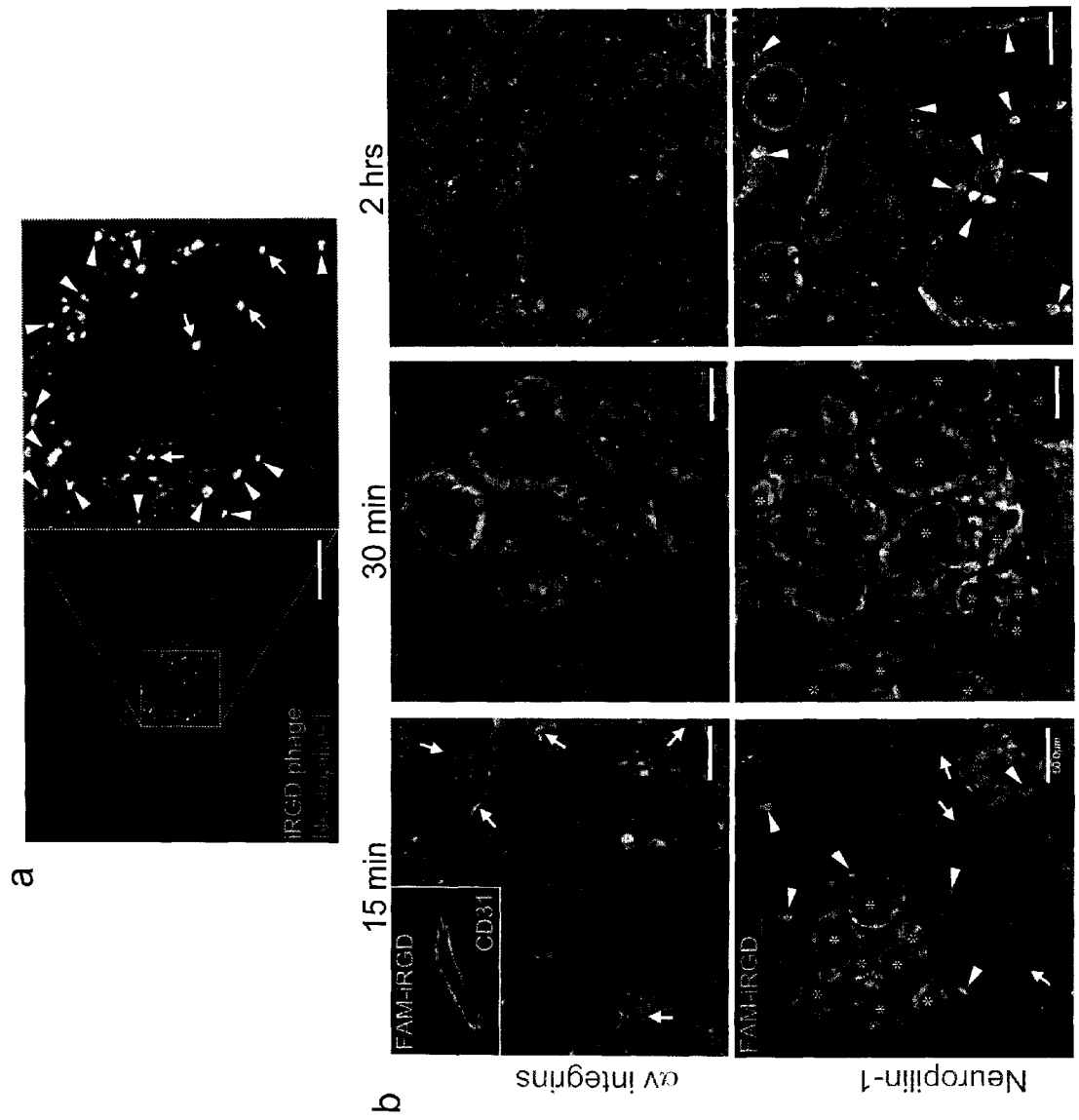
Figure 15A:
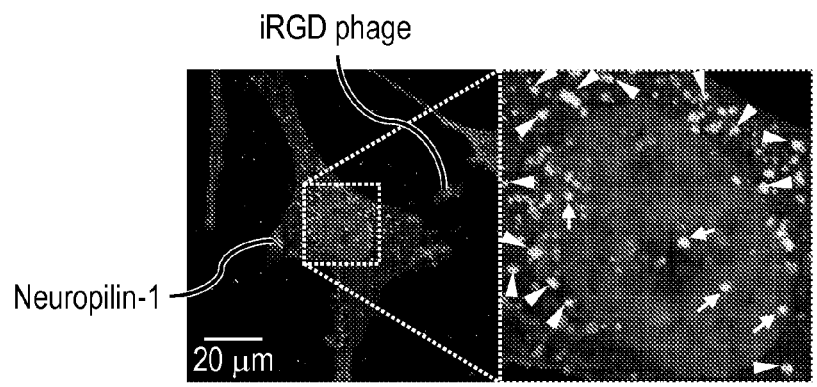
Figure 15B:
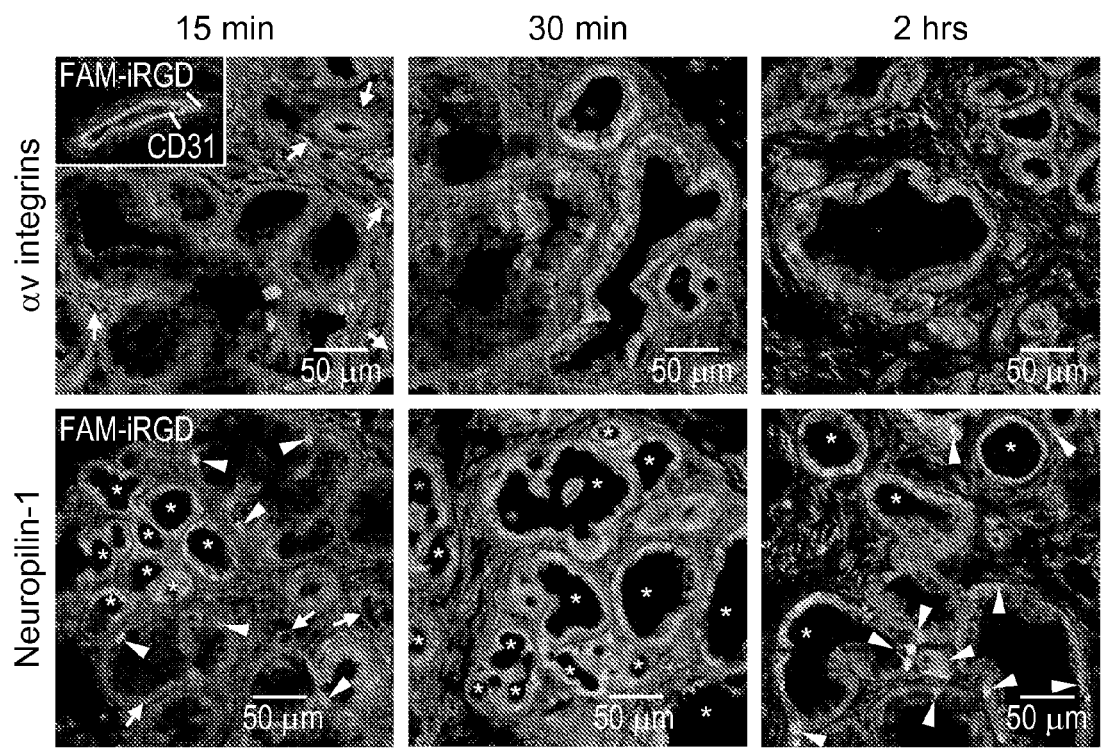

FIGS. 15A and 15B show internalization of iRGD within tumor cells involves neuropilin-1. a, Confocal microscopy images of PPC1 cells incubated with iRGD phage. The cells were stained for phage, neuropilin-1, and nuclei. The right panel is a high magnification view of the dotted area in the left panel. Note that iRGD phage internalizes within PPC1 cells and co-localizes with neuropilin-1 in the perinuclear area (arrowheads) and in the nucleus (arrows). Scale bar=20 µm. b, Time-dependent homing of FAM-iRGD peptide (green) in relation to the expression of αv integrins (right panels) and neuropilin-1 (left panels) in PDACs (Bardeesy and DePinho (2002)). The blood vessels targeted by FAM-iRGD were positive for both αv integrins and neuropilin-1 (arrows). The inset shows CD31 staining of the vasculature targeted by FAM-iRGD. In almost all tumor ducts examined, αv integrins were positive. Tumor cells (arrowheads) and tumor ducts (asterisks) also strongly positive for neuropilin-1 were extremely potent in internalizing and retaining FAM-iRGD. Scale bars=50 µm.

FIGS. 16A and 16B show homing of synthetic iRGD peptide to orthotopic xenografts and spontaneous mouse tumors. Approximately 200 µg of FAM-iRGD in PBS was intravenously administered to mice bearing tumors. The peptides were allowed to circulate for 2 hours and organs were collected and viewed under UV or white light. Arrowheads point to the tumors. a, The tumors were brain and tibia xenografts of a human prostate cancer PPC1 (Zhang et al., Lymphatic zip codes in premalignant lesions and tumors. *Cancer Res.* 66, 5696-5706 (2006)), and orthotopic xenografts of 22rv-1 (Drake et al., Assessing tumor growth and distribution in a model of prostate cancer metastasis using bioluminescence imaging. *Clin. Exp. Metastasis* 22, 674-684 (2005)), a human pancreatic carcinoma MIA PaCa-2 (Sugahara et al., Chondroitin sulfate E fragments enhance CD44 cleavage and CD44-dependent motility in tumor cells. *Cancer Res.* 68, 7191-7199 (2008)), and a human breast cancer BT474 (Rusnak et al., The effects of the novel, reversible epidermal growth factor receptor/ErbB-2 tyrosine kinase inhibitor, GW2016, on the growth of human normal and tumor-derived cell lines in vitro and in vivo. *Mol. Cancer. Ther.* 1, 85-94 (2001)). b, Spontaneous mouse tumors were pancreatic islet tumors of RIP-Tag2 mice (Hanahan, Heritable formation of pancreatic β-cell tumors in transgenic mice expressing recombinant insulin/simian virus 40 oncogenes. *Nature* 315, 115-122 (1985)) and cervical tumors of K14-HPV16 mice (Arbeit et al., Progressive squamous epithelial neoplasia in K14-human papillomavirus type 16 transgenic mice. *J. Virol.* 68, 4358-4368 (1994)).

Figure 17:
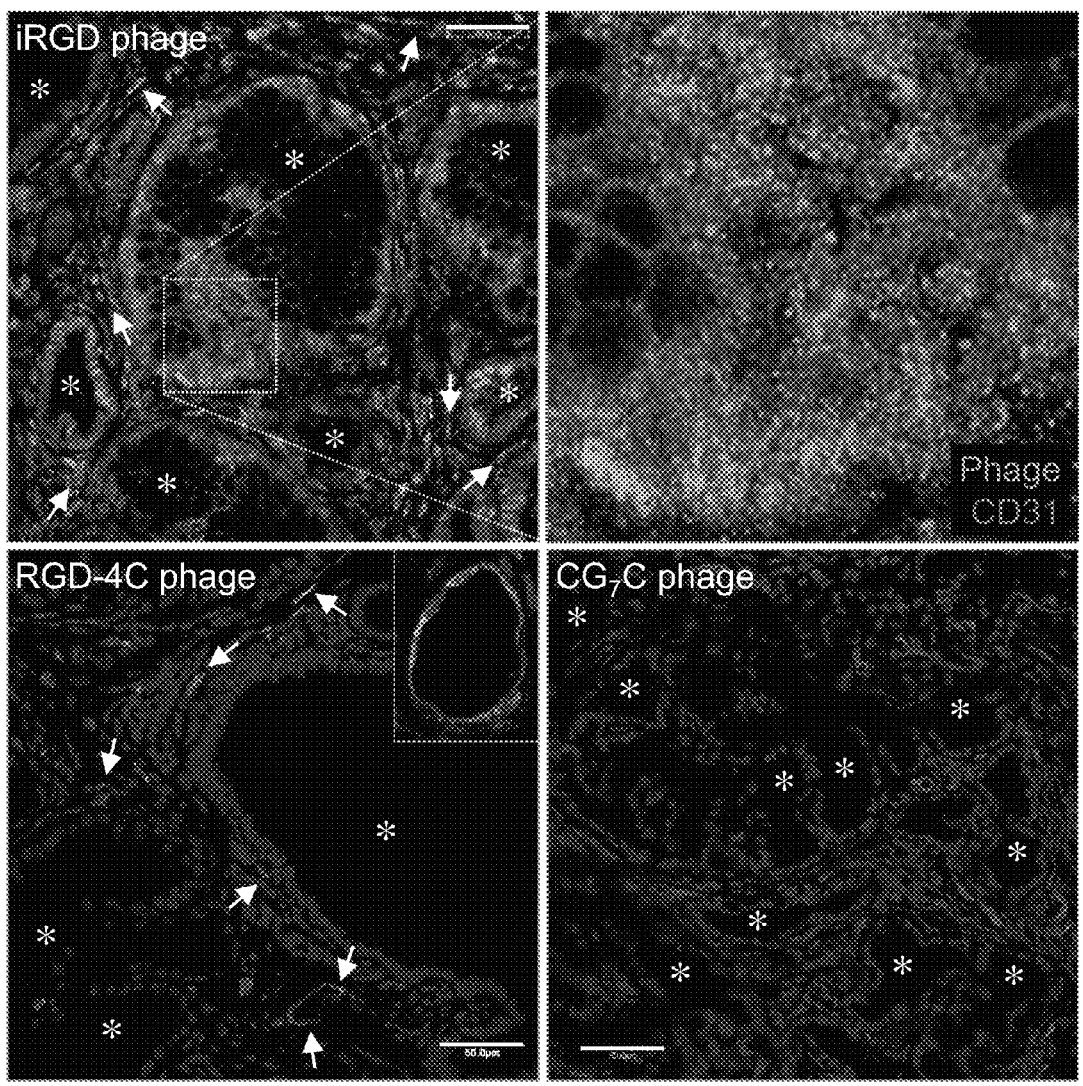

FIG. 17 shows iRGD phage penetrates into the tumor tissue and internalizes into the tumor cells. Confocal images of PDAC tumors from transgenic mice injected with iRGD, RGD-4C, or CG$_7$C phage. Arrows point to blood vessels positive for phage, and asterisks show the tumor ducts. The upper right panel shows a magnified view of the dotted area in the upper left panel. The inset represents a blood vessel targeted by RGD-4C phage. iRGD phage spreads widely into the tumor parenchyma and internalizes into tumor cells, while RGD-4C phage targets the blood vessels but stays in close association with the vasculature. CG$_7$C phage showed no tumor homing. Scale bars=50 µm.

Figure 18:
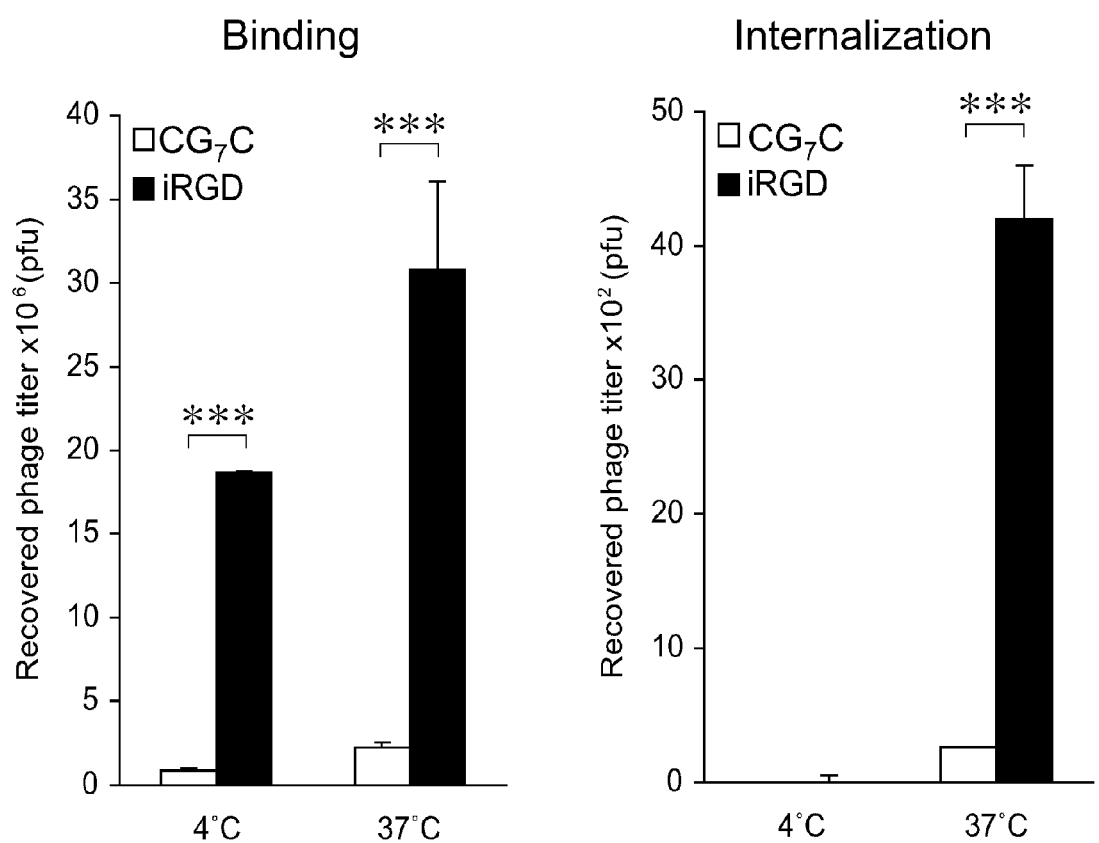

FIG. 18 shows binding and internalization to PPC1 cells of iRGD phage in comparison to CG$_7$C phage. PPC1 cells were treated with iRGD or CG$_7$C phage for 1 hour at 4° C. or 37° C. To assess the internalization, the phage that bound to the cell surface were removed by washing the cells with acid buffer before phage titration. Note that the internalization of iRGD phage does not occur at 4° C. Statistical analysis was performed with Student's t-test. n=3, error bars represent s.d.

Figure 19:
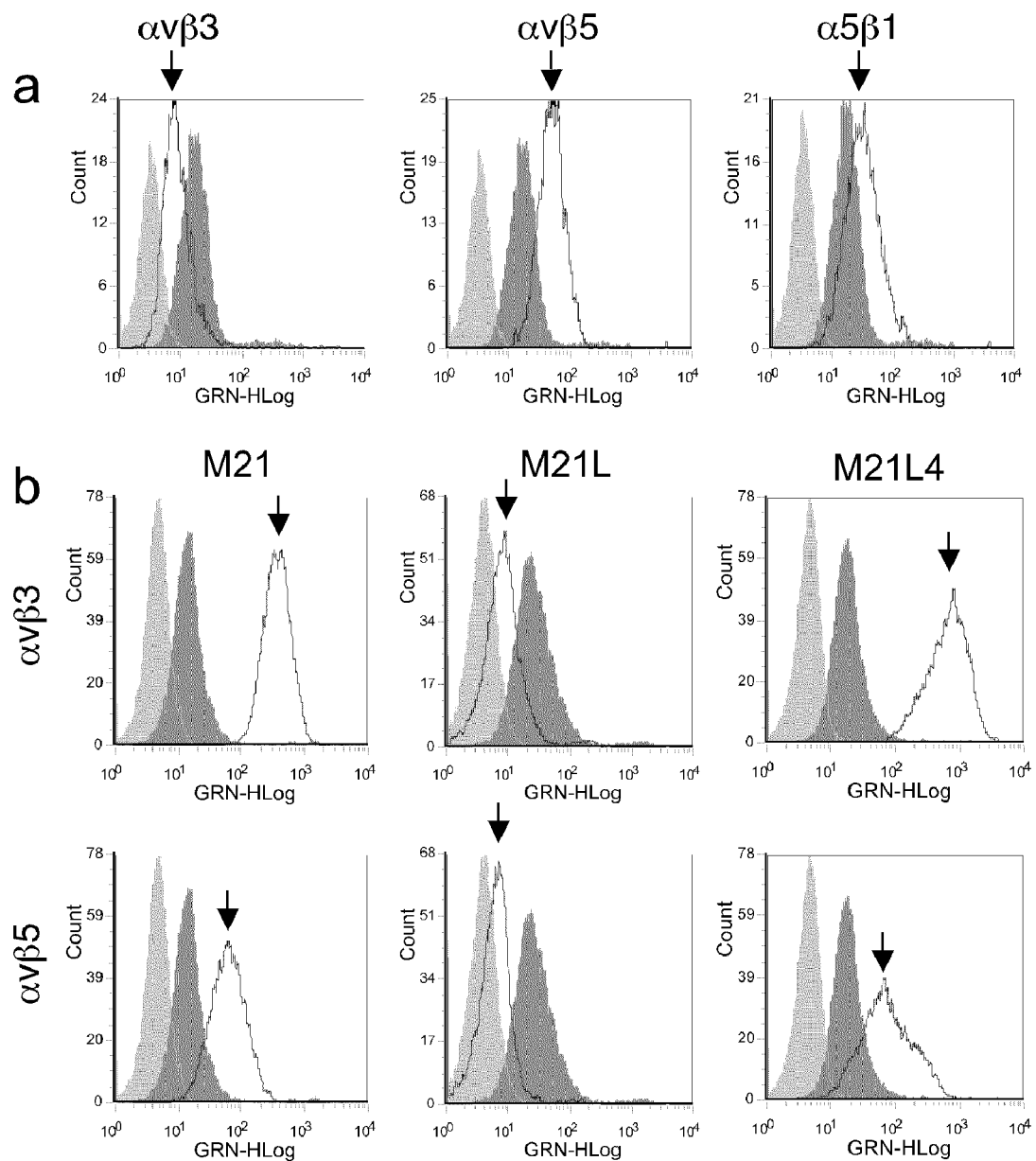

FIGS. 19A and 19B show integrin expression in tumor cells. a, b, Integrin expression in PPC1 (a) and M21 cells (b) analyzed by flow cytometry. The profiles represent the values of unstained cells (light gray), and cells incubated with mouse IgG (dark gray) or appropriate integrin antibodies (unshaded with arrows) as primary antibodies.

Figure 20:
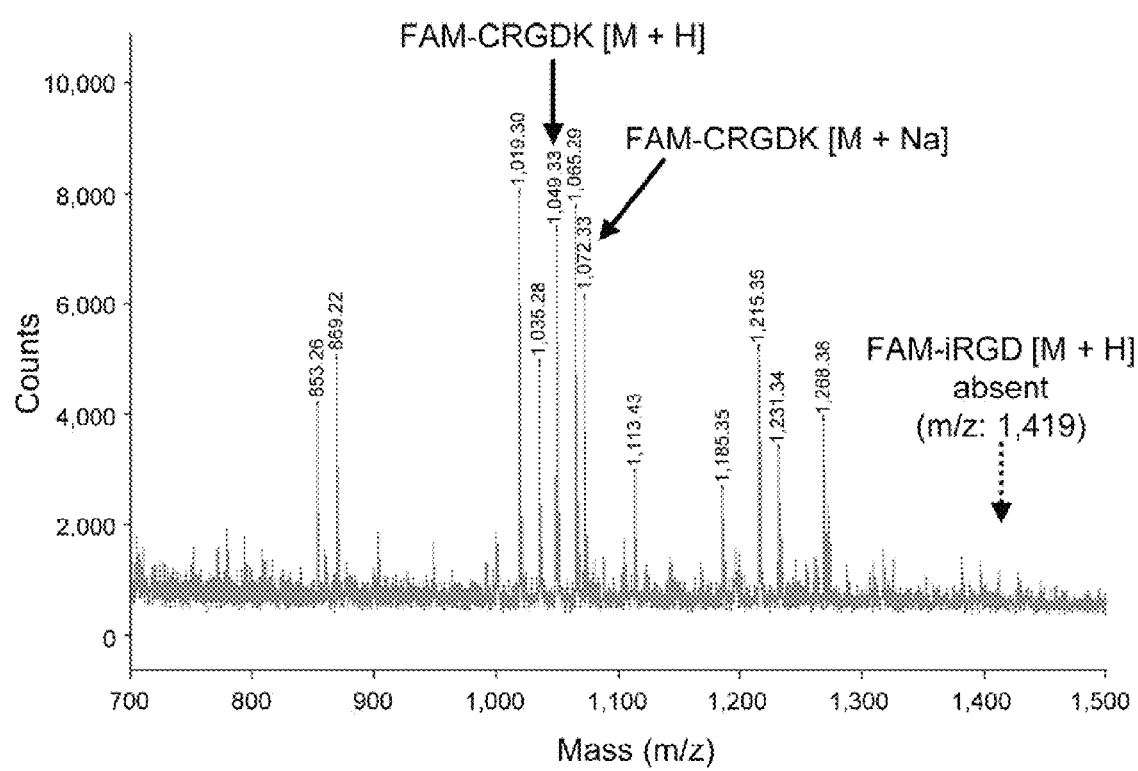

FIG. 20 shows peptide fragments recovered from PPC1 cells treated with FAM-iRGD peptides. PPC1 cells were incubated with FAM-iRGD peptide (FAM at the N-terminus) at 37° C. for 90 min in the presence of the proteasome inhibitor MG132. Peptide fragments were recovered with an anti-FITC affinity column, and analyzed by mass spectrometry. Note the presence of FAM-CRGDK [M+H] (m/z: 1,049) (SEQ ID NO:6) and FAM-CRGDK [M+Na] (m/z: 1,072) (SEQ ID NO:6), and the absence of the full-length FAM-iRGD (m/z: 1,419). No major peptide fragments were recovered from mouse IgG column used as an isotype control for the anti-FITC affinity column, or when a lysate of PPC1 cells that had not been exposed to FAM-iRGD was fractionated on anti-FITC (not shown). An iRGD peptide labeled with FAM at the C-terminus yielded no GPDC-FAM (the 988 mass unit fragment expected from an iRGD cleavage that produces CRGDK (SEQ ID NO:6)) from the cells (not shown). This indicates that the only neuropilin-1-binding N-terminal fragment (CRGDK; SEQ ID NO:6)) internalizes, which could happen if the iRGD peptide is proteolytically cleaved at the K-G bond, and the disulfide bond is reduced, before internalization. Omitting MG132 yielded only peptides smaller than FAM-CRGDK (SEQ ID NO:6) (not shown), indicating that intracellular FAM-CRGDK (SEQ ID NO:6) is degraded in proteasomes.

Figure 21:
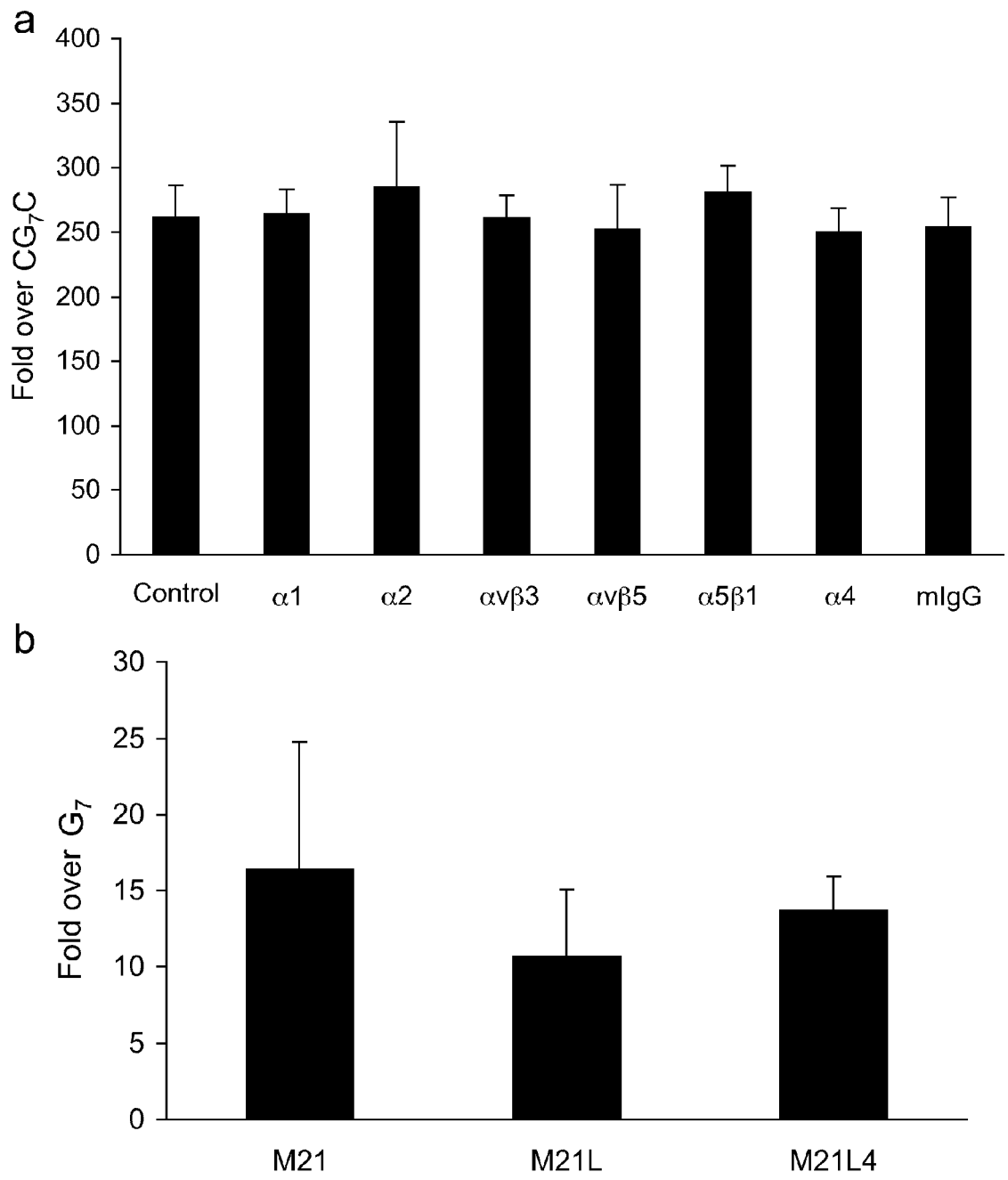

FIGS. 21A and 21B show binding of CRGDK (SEQ ID NO:6) phage to tumor cells in relation to integrin expression. a, Integrin antibodies do not inhibit the binding of CRGDK (SEQ ID NO:6) phage to PPC1 cells. b, CRGDK (SEQ ID NO:6) phage binds similarly to M21 cells with different αv integrin expression levels (refer to FIG. 19B for the αv integrin expression patterns).

Figure 22:
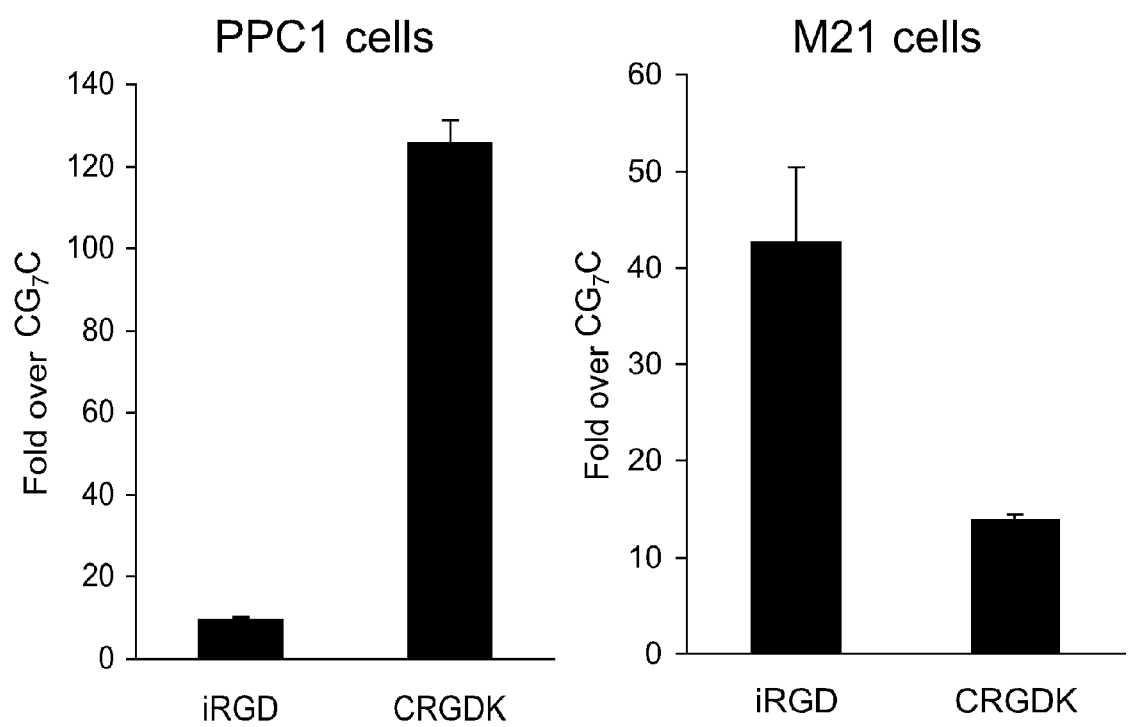

FIG. 22 shows internalization of iRGD and CRGDK (SEQ ID NO:6) phage into PPC1 and M21 cells. Cells were treated with iRGD or CRGDK (SEQ ID NO:6) phage for 1 hour at 37° C. followed by an acid buffer wash to remove the phage that bound to the cell surface. Note that CRGDK (SEQ ID NO:6) phage internalized more efficiently than iRGD phage in PPC1 cells that have high expression of neuropillin-1, whereas it is reversed in M21 cells.

Figure 23:
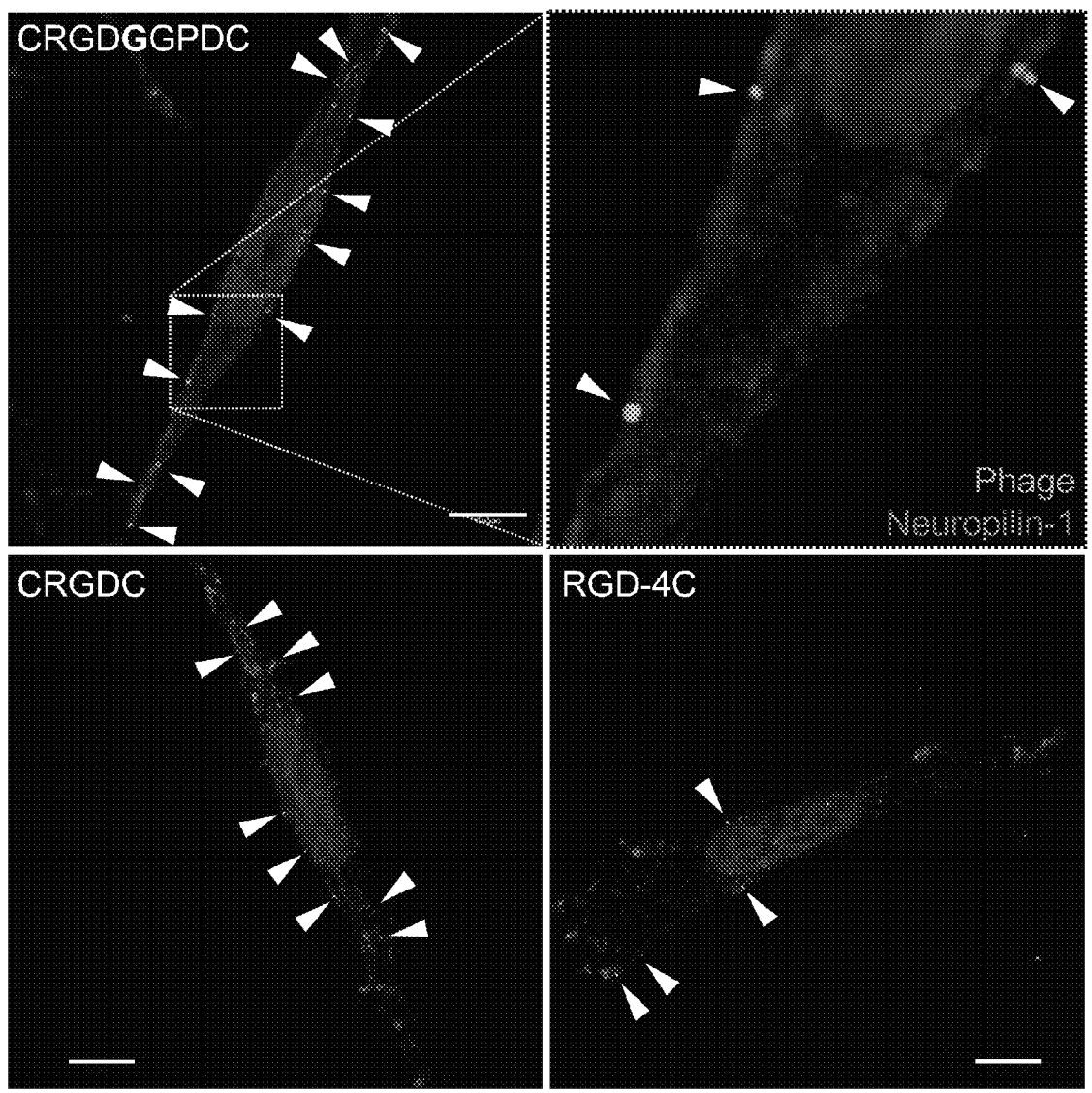

FIG. 23 shows RGD phage that lack a CendR element do not internalize into tumor cells efficiently. Confocal microscopy images of PPC1 cells incubated with T7 phage that express an iRGD phage variant CRGDGGPDC (SEQ ID NO:298), CRGDC (SEQ ID NO:292), or RGD-4C. The cells were stained for phage (arrowed), neuropilin-1 (distal and flanking), and nuclei (central mass). The right panel of CRGDGGPDC (SEQ ID NO:298) phage is a high magnification view of the dotted area in the left panel. Note that the RGD phage bind to the surface of the cells (arrowheads) but do not internalize efficiently into the cells. Scale bars=10 μm.

Figure 24:
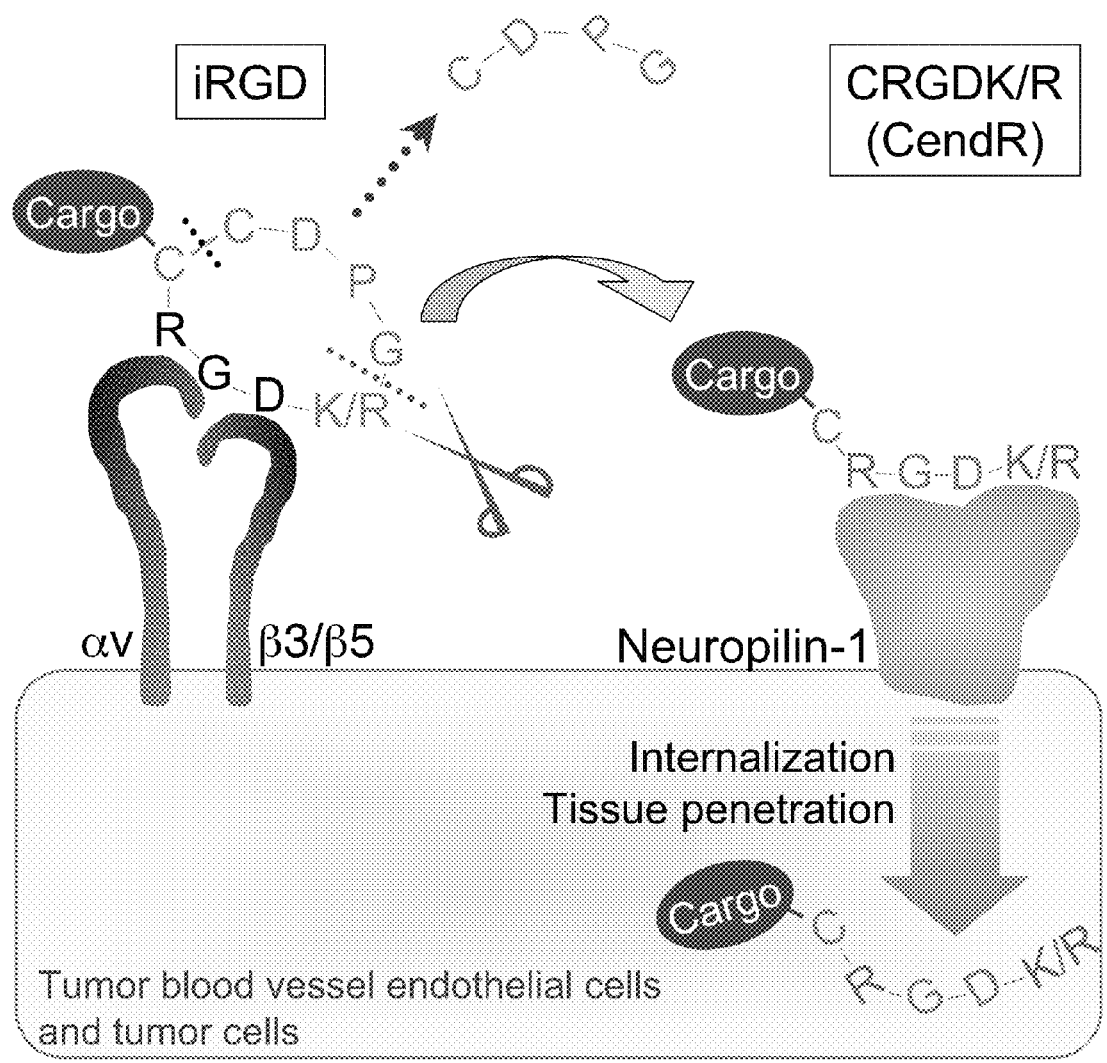

FIG. 24 shows the two step internalization mechanism of iRGD. The iRGD peptide (SEQ ID NO:1) accumulates at the surface of αv integrin-expressing endothelial and other cells in tumors. The RGD motif mediates the integrin binding. The peptide is cleaved by a cell surface-associated protease(s) to expose the cryptic CendR element, RXXK/R (SEQ ID NOs: 13 and 14), at the C-terminus (dotted line with scissors) (SEQ ID NOs:6 and 311). The CendR element then mediates binding to neuropilin-1, with resulting internalization into cells. The peptide can carry into cells a cargo, such as a simple chemical or a nanoparticle, provided that the cargo is attached to the N-terminus of the iRGD peptide because the disulfide bond apparently breaks before the peptide is internalized (arrowed dotted line). The discarded peptide is SEQ ID NO:312.

FIGS. 25A-25C show tumors and enrichment data from phage display screening. a, PPC1 tibia xenografts: Upper panel, x-ray picture taken with Image Station In Vivo FX of the area shown in the lower panel. Arrows point to tumors in tibia. b, GFP-PC-3 tumors disseminated from an injection of one million tumor cells into the left ventricle of the heart. The mouse was imaged under UV light using the Illumatool Bright Light System LT-9900. Tumors that grew in the bones (e.g., jaws, radius, femur) were used for the screening. c, An example of the enrichment obtained in successive rounds of phage display screening.

DETAILED DESCRIPTION OF THE INVENTION

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. General

In vivo screening of phage-displayed peptide libraries was used to probe vascular specialization in tumors. This method has revealed a large degree of heterogeneity in the vasculature; and tissue-specific homing peptides have been identified for a large number of normal organs and tissues, tumors and atherosclerotic lesions (Rajotte at aL, 1998; Ruoslahti, 2002; Liu et al., 2003; Zhang et al., 2005; Kolonin et al., 2006). Tumors have been shown to carry specific vascular markers, both in the blood vessels and lymphatics (Ruoslahti, 2002; Laakkonen et al., 2002; 2004; Zhang et al., 2006). It was reasoned that surveying tumor types that have not been used as targets in phage display screening might reveal additional homing peptide sequences selective for tumors. Prostate cancer and prostate cancer metastases were selected as the target tumors.

A class of peptides has been discovered that selectively target new vasculature or cells and tissue that express αv integrins. In some forms, the peptides have the sequence CRGD(R/K)GP(D/E)C (SEQ ID NO:300). In particular, three peptides that selectively target new vasculature have been identified: CRGDKGPDC (referred to as iRGD1, SEQ ID NO: 1), CRGDRGPDC (referred to as iRGD2, SEQ ID NO: 2), and CRGDKGPEC (referred to as iRGD3, SEQ ID NO: 3). Other examples of this class of peptides include CRGDRGPEC (SEQ ID NO:290). In some forms, the peptides can have the sequence RGD(R/K/H) (SEQ ID NO:325). For example, the peptides can have the sequence CRGD(R/K/H)GP(D/H)C (SEQ ID NO:326). As another example, the peptides can have the sequence CRGD(R/K/H)GP(D/E/H)C (SEQ ID NO:327). As another example, t the peptides can have the sequence CRGD(R/K/H)G(P/V)(D/E/H)C (SEQ ID NO:328). Thus, for example, the peptides can have the sequence CRGDHGPDC (SEQ ID NO:313), CRGDHGPEC (SEQ ID NO:314), CRGDHGPHC (SEQ ID NO:315), CRGDHGVDC (SEQ ID NO:316), CRGDHGVEC (SEQ ID NO:317), CRGDHGVHC (SEQ ID NO:318), CRGDKGPDC (SEQ ID NO:1), CRGDKGPEC (SEQ ID NO:3), CRGDKGPHC (SEQ ID NO:302), CRGDKGVDC (SEQ ID NO:319), CRGDKGVEC (SEQ ID NO:320), CRGDKGVHC (SEQ ID NO:321), CRGDRGPDC (SEQ ID NO:2), CRGDRGPEC (SEQ ID NO:290), CRGDRGPHC (SEQ ID NO:303), CRGDRGVDC (SEQ ID NO:322), CRGDRGVEC (SEQ ID NO:323), OR CRGDRGVHC (SEQ ID NO:324).

These homing peptides demonstrate the feasibility of systemic targeting of tumors to deliver anti-cancer agents.

B. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed are methods and compositions related to an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) or related amino acid sequences.

Also disclosed are isolated peptides comprising an amino acid segment comprising, for example, the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C_ (SEQ ID NO:330) having one or more conservative amino acid substitutions. One of skill in the art is readily able to assess which amino acids can be substituted and retain the function of the peptide.

The peptides can have, for example, a length of less than 100 residues. The peptides can have, for example, a length of less than 50 residues. The peptides can have, for example, a length of less than 20 residues. The disclosed amino acid segments can comprise, for example, the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330). The disclosed amino acid segments can comprise, for example, the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions. The disclosed peptides can be, for example, circular or cyclic. The disclosed peptides can be, for example, circularized or cyclized via a disulfide bond. The disclosed peptides can be, for example, non-circular or linear. The disclosed amino acid segments can be, for example, circular or cyclic. The disclosed amino acid segments can be, for example, circularized or cyclized via a disulfide bond. The disclosed amino acid segments can be, for example, non-circular or linear. The disclosed peptides can consist of, for example, the amino acid segment. The disclosed peptides can selectively home to, for example, sites of angiogenesis, such as wound sites or tumors.

Also disclosed are conjugates, wherein the conjugate comprises a moiety linked to a disclosed peptide, such as a peptide comprising an amino acid segment comprising, for example, the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions.

The moiety can be, for example, an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination. The moiety can be, for example, a therapeutic agent. The moiety can be, for example, a detectable agent. The conjugate can comprise, for example, a virus. The conjugate can comprise, for example, a phage. The conjugate can further comprise, for example, a second peptide, wherein the second peptide can comprise, for example, an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions.

The conjugate is directed to, or targeted to, or homes to, angiogenic tissue in the subject, which thus directs the moiety to angiogenic tissue. When a tumor is being treated, the moiety can thus be directed to an angiogenic tissue associated with the tumor. The conjugate can be used, for example, to treat the cancer. The conjugate can have a therapeutic effect on the cancer. For example, the size of a tumor can be reduced and/or the growth of a tumor can be reduced, stopped or reversed. The moiety can be used to detect the cancer, visualize one or more tumors, or both.

The subject can have a wound in which angiogenesis is taking place. The wound, for example, can be chronic, or can be acute. The wound can be in any stage of healing, from the inflammatory stage, to granulation, to contraction, to epithelialization, to the remodeling phase, which includes collagenation and the formation of scar tissue. The wound can be, for example, from an auto, boat, or airplane accident, a gunshot, stabbing or knife accident, a fall, an industrial accident, or impalement. The wound can also be formed during surgery, for example. The wound can also be, for example, the result of a treatment, such as the implanting of a port.

The conjugate can be used, for example, to treat at least one of the sites of injury. The conjugate can have a therapeutic effect on at least one of the sites of injury. The moiety can be used, for example, to detect, visualize, or image at least one of the sites of injury, or a combination.

The conjugate can also be used to treat, for example, diabetic blindness, age-related macular degeneration, rheumatoid arthritis, or psoriasis, for example.

The conjugate can be used, for example, to direct the moiety to a cell or tissue expressing one or more αv integrins, neuropilin-1, or both. For example, the cell or tissue can be expressing one or more αv integrins or the cell or tissue can be expressing one or more αv integrins and neuropilin-1. The integrin can be, for example, αvβ3 integrin, αvβ5 integrin, α5β1 integrin, or a combination.

A. Homing Molecules

Disclosed are homing molecules that selectively home to sites of angiogenesis. A variety of homing molecules can be used in the disclosed compositions, conjugates and methods. Such homing molecules include, without limitation, peptides as disclosed herein. In particular, reference herein to, and description of, a homing molecule and its use are also specifically contemplated to refer to and apply to the disclosed peptides. The disclosed compounds, compositions, conjugates and methods can include or use the disclosed homing molecules in various forms. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby.

As used herein, the term "molecule" is used broadly to mean a polymeric or non-polymeric organic chemical such as a small molecule drug; a nucleic acid molecule such as an RNA, a DNA such as a cDNA or oligonucleotide; a peptide; or a protein such as a growth factor receptor or an antibody or fragment thereof such as an Fv, Fd, or Fab fragment or another antibody fragment containing the antigen-binding domain.

The term "homing molecule" as used herein, means any molecule that selectively homes in vivo to a site of angiogenesis, or tumors in preference to normal tissue (specifically, the vasculature of tumors). Similarly, the term "homing peptide" means a peptide that selectively homes in vivo to a site of angiogenesis. It is understood that a homing molecule that selectively homes in vivo to a site of angiogenesis can exhibit preferential homing to such a site.

By "selectively homes" is meant that in vivo, the homing molecule binds preferentially to the target as compared to non-target. Such a homing molecule can selectively home, for example, to a site of angiogenesis. Selective homing to, for example, an angiogenesis site generally is characterized by at least a two-fold greater localization within angiogenesis, as compared to several tissue types of tissue not undergoing angiogenesis. A homing molecule can be characterized by 5-fold, 10-fold, 20-fold or more preferential localization to regenerating tissue as compared to several or many tissue types of non-regenerating tissue, or as compared to-most or all non-regenerating tissue. Thus, it is understood that, in some cases, a homing molecule homes, in part, to one or more normal organs in addition to homing to regenerating tissue, wound tissue, or tumors. Selective homing can also be referred to as targeting.

The term "angiogenesis" is defined as a physiological process involving the growth of new blood vessels from pre-existing vessels. Vasculogenesis is the term used for spontaneous blood-vessel formation, and intussusception is the term for new blood vessel formation by splitting off existing ones. Angiogenesis is a normal process in growth and development, as well as in wound healing. It is also a fundamental step in the transition of tumors from a dormant state to a malignant state. Angiogenesis is said to be taking place when there is a 10% or more increase in the growth of new blood vessels in a given area when compared with the same tissue prior to angiogenesis or to a standard or control.

In some embodiments, a homing molecule can be a molecule that selectively homes to tissue undergoing angiogenesis, such as wound tissue, or tumors and which is not an antibody or antigen-binding fragment thereof. The term "antibody" is an art-recognized term that refers to a peptide or polypeptide containing one or more complementarity determining regions (CDRs). See, for example, Borrabaeck, Antibody Engineering 2nd Edition, Oxford University Press, New York (1995).

Homing, including preferential and/or selective homing, does not mean that the homing molecule does not bind to any normal and/or non-targeted areas (for example, non-tumor, non-clot, and/or non-wound). In some embodiments, homing selectivity can be, for example, at least about 20-fold, at least about 30-fold, at least about 50-fold, at least about 75-fold, at least about 100-fold, at least about 150-fold, or at least about 200-fold selective for a corresponding target in terms of relative $K_i$ over other non-target components. In some embodiments, the homing molecule can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, the homing molecule can have a $K_i$ value against a target of less than about 200 nM, less than about 150 nM, less than about 100 nM, or less than about 75 nM. In some preferred embodiments, the homing molecule can have a $K_i$ value against a target of more than about 50 nM, more than about 25 nM, more than about 20 nM, more than about 15 nM, more than about 10 nM, more than about 5 nM, more than about 3 nM, or more than about 1 nM. In some preferred embodiments, the targeting moiety binds its target with a $K_D$ less than about $10^{-8}$M, less than about $10^{-9}$ M, less than about $10^{-10}$ M, less than about $10^{-11}$ M, less than about $10^{-12}$ M, less than about $10^{-13}$ M, or less than about $10^{-14}$ M.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces.

1. Peptides and Peptidomimetics

Disclosed are methods and compositions related to an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) or related amino acid sequences. The isolated peptides can comprise, for example, an amino acid segment comprising, for example, the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions.

The amino acid segment can comprise an amino acid sequence at least about 90%, 80%, 70%, or 60% identical to the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or any percentage in between that represents a change, including addition or deletion, of one or more amino acid. The amino acid segment can comprise the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330). The amino acid segment can comprise the amino acid sequence of SEQ ID NO: 1, SEQ ID NO: 2, SEQ ID NO: 3, SEQ ID NO:290, one of the amino acid sequences CRGD(R/K/H)GV (D/E/H)C (SEQ ID NO:329), or one of the amino acid sequences CRGDHGP(D/E/H)C (SEQ ID NO:330) having one, two, three, four, five, six, seven, eight, or nine conservative amino acid substitutions. The amino acid segment can comprise a chimera of the amino acid sequence SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330). Such a chimera can be additive, where sequence of one sequence is added to another sequence, substitutional, where sequence of one sequence is substituted for sequence of another sequence, or a combination. The disclosed peptides can consist of the amino acid segment.

The amino acid segment can be, for example, non-circular, linear, circular or cyclic. The amino acid segment can be circularized or cyclized via any suitable linkage, for example, a disulfide bond. The peptide can have any suitable length, such as a length of less than 100 residues. The peptide can have a length of, for example, less than 50 residues. The peptide can have a length of, for example, less than 20 residues.

The disclosed peptides can selectively home to tissue undergoing angiogenesis, such as wound tissue, or tumors. The disclosed peptides can selectively interact with such tissue or tumors.

Also disclosed are isolated peptides which have a length of less than 100 residues and which include the amino acid sequence SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) or a peptidomimetic thereof. Such an isolated peptide can have, for example, a length of less than 50 residues or a length of less than 20 residues. In particular embodiments, disclosed can be a peptide that includes the amino acid sequence SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), and has a length of less than 20, 50 or 100 residues.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

i. Peptide Variants

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent than those discussed above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides which contains a homing peptide fused to a second peptide having a separate function. Such bifunctional peptides have at least two functions conferred by different portions of the full-length molecule and can, for example, display anti-angiogenic activity or pro-apoptotic activity in addition to selective homing activity.

Also disclosed are isolated multivalent peptides that includes at least two subsequences each independently containing a homing molecule (for example, the amino acid sequence SEQ ID NO: 1, SEQ ID NO: 2, SEQ ID NO: 3, SEQ ID NO:290, one of the amino acid sequences CRGD(R/K/H) GV(D/E/H)C (SEQ ID NO:329), or one of the amino acid sequences CRGDHGP(D/E/H)C (SEQ ID NO:330), or a conservative variant or peptidomimetic thereof). The multivalent peptide can have, for example, at least three, at least five or at least ten of such subsequences each independently containing a homing molecule (for example, the amino acid sequence of SEQ ID NO: 1, SEQ ID NO: 2, SEQ ID NO: 3, SEQ ID NO:290, one of the amino acid sequences CRGD(R/K/H) GVD/E/HC (SEQ ID NO:329), or one of the amino acid sequences CRGDHGP(D/E/H)C (SEQ ID NO:330), or a conservative variant or peptidomimetic thereof). In particular embodiments, the multivalent peptide can have two, three, four, five, six, seven, eight, nine, ten, fifteen or twenty identical or non-identical subsequences. In a further embodiment, the multivalent peptide can contain identical subsequences, which consist of a homing molecule (for example, the amino acid sequence SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) or a conservative variant or peptidomimetic thereof). In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

If desired, an isolated peptide, or a homing molecule as discussed further elsewhere herein, can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl) benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

B. Conjugates

Disclosed are conjugates comprising a moiety and a homing molecule, such as a peptide as disclosed herein. For example, disclosed are conjugates containing a therapeutic agent linked to a homing molecule that selectively homes to tissue undergoing angiogenesis. Disclosed conjugates can comprise, for example, a moiety linked to a peptide comprising an amino acid segment comprising, for example, the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330).

Any form or type of homing molecule as disclosed herein can be used in the disclosed conjugates. The moiety can be any molecule. Preferably the moiety is a molecule that is usefully targeted to the target of the homing molecule. For example, moieties that affect the target, such as moieties with therapeutic effect, or that facilitate detection, visualization or imaging of the target, such as fluorescent molecule or radionuclides. Disclosed peptides that home to tissue undergoing angiogenesis can be usefully combined with, for example, moieties that can, for example, promote wound healing, treat inflammation or pain, or treat cancer. A variety of therapeutic agents are useful in the conjugates including, without limitation, a moiety that is an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination.

A conjugate containing multiple homing molecules can include, for example, two or more, three or more, five or more, ten or more, twenty or more, thirty or more, forty or more, fifty or more, 100 or more, 200 or more, 300 or more, 400 or more, 500 or more, or 1000 or more homing molecules. In one embodiment, the conjugate includes homing molecules that all have an identical amino acid sequence. In another embodiment, the conjugate includes homing molecules having two or more non-identical amino acid sequences. For example, SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) can be used separately or together. Moieties useful in a conjugate incorporating multiple homing molecules include, without limitation, phage, retroviruses, adenoviruses, adeno-associated viruses and other viruses, cells, liposomes, polymeric matrices, non-polymeric matrices, particles such as gold particles, microdevices, nanodevices, and nano-scale semiconductor materials.

A conjugate can contain, for example, a liposome or other polymeric matrix linked to at least two homing molecules. If desired, the liposome or other polymeric matrix can be linked to at least ten, at least 100 or at least 1000 homing molecules. Liposomes can be useful in such conjugates; liposomes consist of phospholipids or other lipids, are nontoxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule. Components of the disclosed conjugates can be combined, linked and/or coupled in any suitable manner. For example, moieties and homing molecules can be associated covalently or non-covalently, directly or indirectly, with or without a linker moiety.

C. Moieties

Disclosed are compositions and methods of directing a moiety to a target. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide. Useful moieties include, yet are not limited to an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate.

1. Therapeutic Agents

The moiety incorporated into a conjugate can be a therapeutic agent. As used herein, the term "therapeutic agent" means a molecule which has one or more biological activities in a normal or pathologic tissue. A variety of therapeutic agents can be included in a conjugate.

The conjugates disclosed herein can be used to home to wounds or tissue injuries. Moieties useful for this purpose can include molecules belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue.

The conjugate can also contain a cancer chemotherapeutic agent. As used herein, a "cancer chemotherapeutic agent" is a chemical agent that inhibits the proliferation, growth, lifespan or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

A therapeutic agent useful in a conjugate can be an antibody such as a humanized monoclonal antibody. As an example, the anti-epidermal growth factor receptor 2 (HER2) antibody, trastuzumab (Herceptin; Genentech, South San Francisco, Calif.) is a therapeutic agent useful in a conjugate for treating HER2/neu overexpressing breast cancers (White et al., Annu Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. A therapeutic agent useful in a conjugate also can be an anti-angiogenic agent. As used herein, the term "anti-angiogenic agent" means a molecule that reduces or prevents angiogenesis, which is the growth and development of blood vessels. The conjugates can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

2. Detectable Agents

The moiety in the disclosed conjugates can also be a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed conjugates and imaging methods include yet are not limited to radiolabels and fluorescent molecules. The detectable agent can be, for example, any moiety that facilitates detection, either directly or indirectly, preferably by a non-invasive and/or in vivo visualization technique.

In preferred embodiments, the detectable agent can be coupled to the homing molecule in such a way so as not to interfere with the ability of the homing molecule to home to the target. In some embodiments, the detectable agent can be chemically bound to the homing molecule. In some embodiments, the detectable agent can be chemically bound to a moiety that is itself chemically bound to the homing molecule, indirectly linking the imaging and targeting moieties.

D. Pharmaceutical Compositions and Carriers

The disclosed conjugates can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

Methods

Disclosed herein are methods of using the disclosed homing molecules, such as the disclosed peptides. For example, disclosed are methods of directing a moiety to tissue undergoing angiogenesis comprising administering to the subject a conjugate as disclosed herein. As discussed above, the tissue can be at the site of a tumor, or a wound, such as those caused by injury or surgery.

The conjugates disclosed herein can be useful in subjects with tumors, since tumors are associated with angiogenesis. Disclosed is a method of directing a moiety to tumors, comprising administering to the subject any of the conjugates disclosed herein. For example, the conjugate can have a therapeutic effect. The subject can have one or more sites to be targeted, wherein the moiety is directed to one or more of the sites to be targeted. For example, the subject can have multiple wounds or lesions that can be treated with the moieties disclosed herein. The subject can also have cancer, and the moiety can be directed to tumor angiogenesis in the subject. In this case, the conjugate can have a therapeutic effect on the cancer. For example, the size of the tumor can be reduced, or the growth of the tumor can be reduced, stopped, or reversed. The moiety can also be used to detect the cancer, visualize one or more tumors, or both.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Cancers and tumors that are particularly useful as targets for the disclosed compositions and methods are cancers and tumors that express one or more αv integrins, neuropilin-1, or both. For example, the cancers and tumors can be expressing one or more αv integrins or the cancers and tumors can be expressing one or more αv integrins and neuropilin-1. Cancers and tumors that express higher than normal neuropilin-1 are particularly useful targets. For these purposes, it is also sufficient that some cells in or near a tumor express one or more αv integrins and some cells in the tumor express neuropilin-1. As used herein, a normal level of expression of a gene or protein is the level of expression in a normal tissue or cell. Any suitable comparison tissue or cell can be used. For example, in the case of cancer cells and tumors, the level in non-cancerous or non-tumorous tissue can be used to establish what is a normal level of expression. It may be useful to use normal cells or tissues of the same type as the source of the cancer or tumor.

Disclosed is a method of directing a moiety to tumors, comprising determining if a tumor in a subject expresses one or more αv integrins, neuropilin-1, or both, and if the tumor expresses one or more αv integrins, neuropilin-1, or both, administering to the subject any of the conjugates disclosed herein. For example, the tumor can be expressing one or more αv integrins or the tumor can be expressing one or more αv integrins and neuropilin-1. Also disclosed is a method of directing a moiety to tumors, comprising determining if a tumor in a subject expresses neuropilin-1 at a level higher than normal, and if the tumor expresses o neuropilin-1 at a level higher than normal, administering to the subject any of the conjugates disclosed herein.

Also disclosed is a method of directing a moiety to a tumor, comprising administering to the subject the conjugate, wherein the conjugate comprises a moiety linked to an isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), or the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330) having one or more conservative amino acid substitutions. The method can further comprise determining if a tumor in the subject expresses one or more αv integrins, neuropilin-1, or both, and if the tumor expresses one or more αv integrins, neuropilin-1, or both, administering the conjugate to the subject. For example, the tumor can be expressing one or more αv integrins or the tumor can be expressing one or more αv integrins and neuropilin-1. The method can further comprise determining if a tumor in the subject expresses neuropilin-1 at a level higher than normal, and if the tumor expresses neuropilin-1 at a level higher than normal, administering the conjugate to the subject. The cells in the tumor can express a αv integrin. The cells in the tumor can express neuropilin-1. The cells in the tumor can express a αv integrin and neuropilin-1. The cells in the tumor can express neuropilin-1 at a level higher than normal. The integrin can be, for example, αvβ3 integrin, αvβ5 integrin, α5β1 integrin, or a combination.

Disclosed are methods wherein the therapeutic effect comprises a reduction in inflammation. By "reduction in inflammation" is meant a decrease in inflammation compared to if the inflammation were not treated. The reduction in inflammation can be about 5, 10, 15, 20, 25, 30, 35, 40, 45, 50, 55, 60, 65, 70, 75, 80, 85, 90, 95, or 100% increase, or about 1, 2, 3, 4, 5, 6, 7, 8, 9, 10, 20, 30, 40, 50, 60, 70, 80, 90, or 100 fold, or higher. There can also be an increase in speed of wound healing, as compared to an untreated wound. The increase in speed of wound healing can be about 5, 10, 15, 20, 25, 30, 35, 40, 45, 50, 55, 60, 65, 70, 75, 80, 85, 90, 95, or 100% increase, or about 1, 2, 3, 4, 5, 6, 7, 8, 9, 10, 20, 30, 40, 50, 60, 70, 80, 90, or 100 fold, or higher. There can also be a reduction in the amount of scar tissue as compared to an untreated site of injury or wound. The reduction in the amount of scar tissue can be about 5, 10, 15, 20, 25, 30, 35, 40, 45, 50, 55, 60, 65, 70, 75, 80, 85, 90, 95, or 100%. There can also be a reduction in the amount of pain experienced by the subject in need thereof, compared to the amount of pain experienced if not treated for pain. This reduction in pain can be about a 5, 10, 15, 20, 25, 30, 35, 40, 45, 50, 55, 60, 65, 70, 75, 80, 85, 90, 95, or 100% reduction. There can also be a decrease in swelling. This decrease in swelling can be compared to untreated swelling, and can be about a 5, 10, 15, 20, 25, 30, 35, 40, 45, 50, 55, 60, 65, 70, 75, 80, 85, 90, 95, or 100% decrease in swelling. There can also be a decrease in tissue necrosis, compared to untreated tissue. The decrease in necrosis can be about 5, 10, 15, 20, 25, 30, 35, 40, 45, 50, 55, 60, 65, 70, 75, 80, 85, 90, 95, or 100%.

The conjugates disclosed herein can also be useful in subjects with arthritis and other inflammatory diseases, as such lesions are often associated with angiogenesis. The conjugates can be used to treat or diagnose any disease, condition, or disorder associated with angiogenesis. For example, macular degeneration and diabetic vascular complications can be diagnosed and/or treated.

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330), is to link two or more peptides or polypeptides together by protein chemistry techniques. For example, peptides or polypeptides can be chemically synthesized using currently available laboratory equipment using either Fmoc (9-fluorenylmethyloxy-carbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Figure 1:
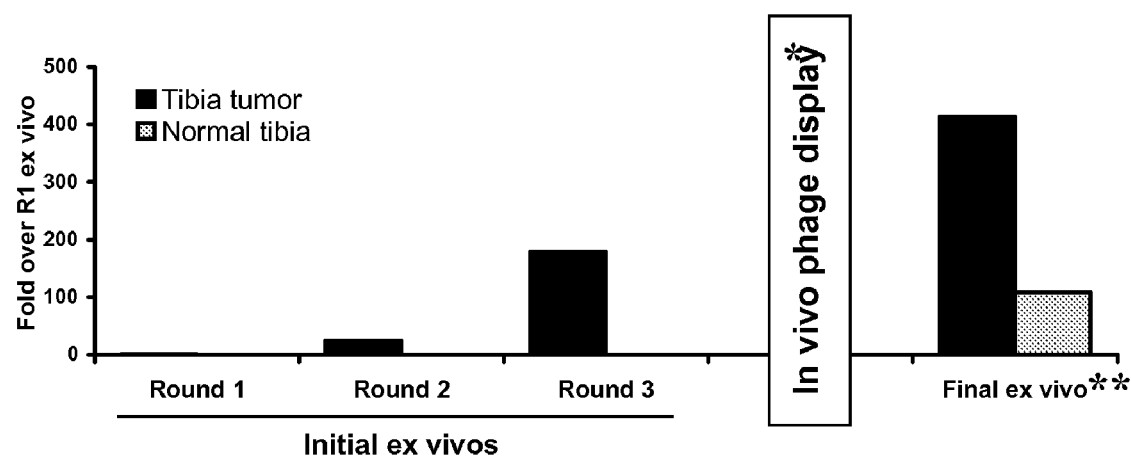
FIG. 1 shows an example of the enrichment pattern of the T7 phage library during screening for peptides that selectively home to the vasculature in bone (tibia) xenografts of human prostate cancer. Three rounds of ex vivo phage display were performed followed by one round of in vivo phage display. The selected phage pool was then subjected to an additional round of ex vivo phage display and its binding to the target tumor was compared with binding to normal bone. Random individual phage clones were sequenced from the in vivo selection rounds and the final ex vivo rounds. The results are shown in Table 1.

Molecular Changes in the Vasculature of Injured Tissues i. Identification of Homing Peptides by Phage Display To identify candidate peptides that home to the vasculature in tumors, a peptide library in T7 phage was screened. An example of the enrichment of the library observed during the screenings is shown in FIG. 1. Ex vivo screening was performed by incubating the T7 phage library (diversity approximately $10^9$) with cell suspensions made out of bone xenografts of various human prostate cancer cells, and the phage that bound to the cells were recovered for titration, and amplified for further rounds. The ex vivo rounds were repeated three times before moving into an in vivo phage display. Ex vivo and in vivo phage selections were performed as described in Hoffman et al., "In vivo and ex vivo selections using phage-displayed libraries," in Clarkson and Lowman (Eds.) Phage Display: A Practical Approach Oxford, U.K.: Oxford University Press (2004)).

In the in vivo phase of the screening, the ex vivo selected phage pool was intravenously injected into nude (immune deficient) mice bearing bone xenografts of human prostate cancer cells. The mice were sacrificed 10 min later by perfusing through the heart with PBS, and the tumor and other tissues were collected for phage titration and recovery. The phage from tumor tissue were amplified and used to perform a final ex vivo phage display. Here, the binding of the phage pool to the target tumor was compared with that to a normal bone. A limited number of individual phage clones were randomly picked up from the target tumor and the normal bone, and were subjected for sequencing.

Sequencing of individual phage clones revealed peptide sequences that appeared multiple times in the selected pools (Table 1). Three sequences, each containing an RGD motif, were chosen for further analysis. The selected peptides are cyclic peptides CRGDKGPDC (referred to as iRGD1, SEQ ID NO: 1), CRGDRGPDC (referred to as iRGD2, SEQ ID NO: 2), and CRGDKGPEC (referred to as iRGD3, SEQ ID NO: 3).

ii. Tumor-Homing of iRGD Peptide

Figure 2:
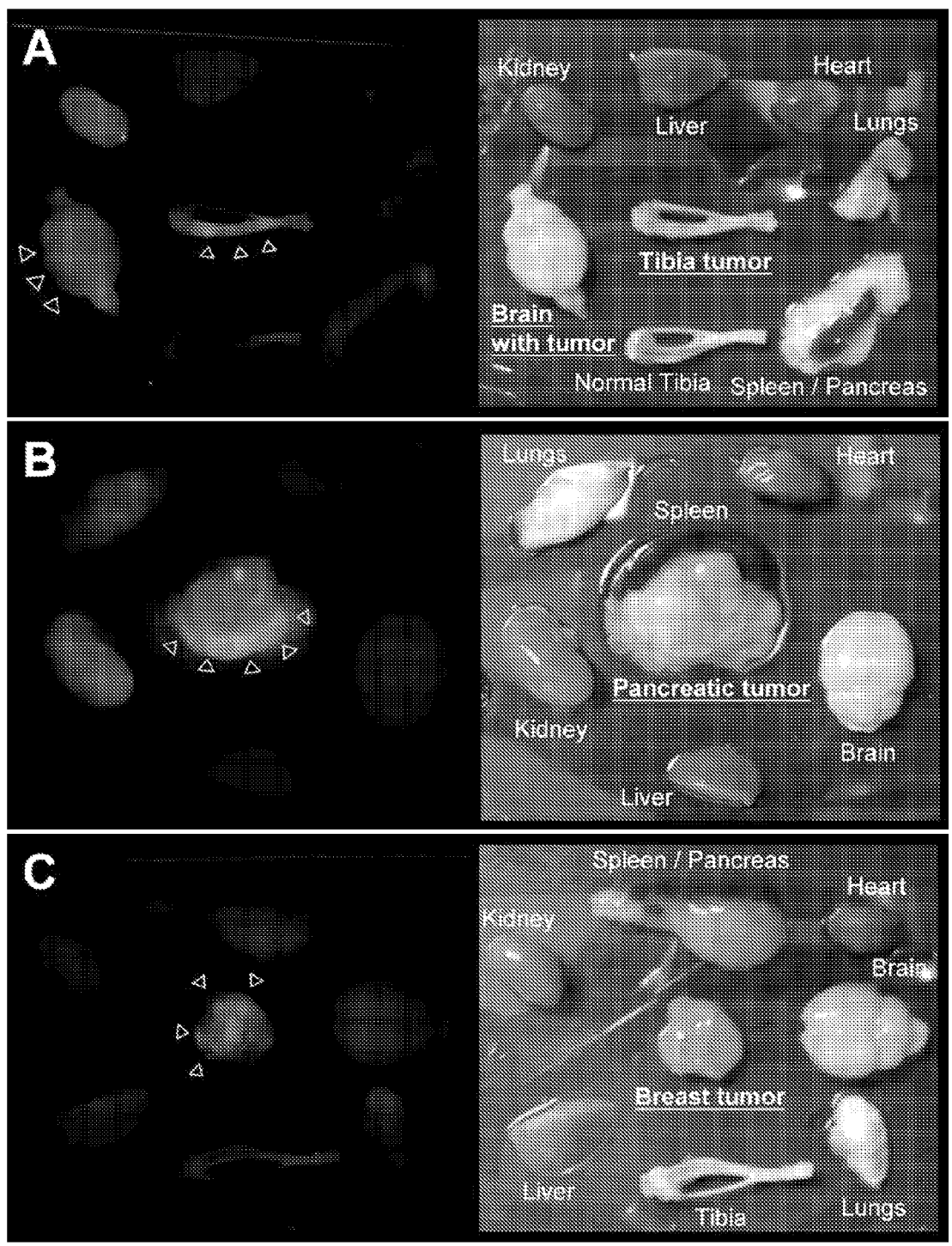
FIGS. 2A, 2B and 2C show homing of iRGD1 peptide to various human xenograft tumors. Fluorescamine-labeled iRGD1 peptide (200 μg) was injected through the tail vein into immune deficient mice bearing PPC1 human prostate cancer xenografts in the tibia and the brain (A), MIA PaCa-2 human pancreatic orthotopic xenograft tumors (B), or MDA-MB-435 breast carcinoma orthotopic xenograft tumors (C). After 4.5 hrs of circulation the mice were perfused to remove unbound peptide and the organs were harvested and observed under UV light (left panels) and white light (right panels).
Figure 3:
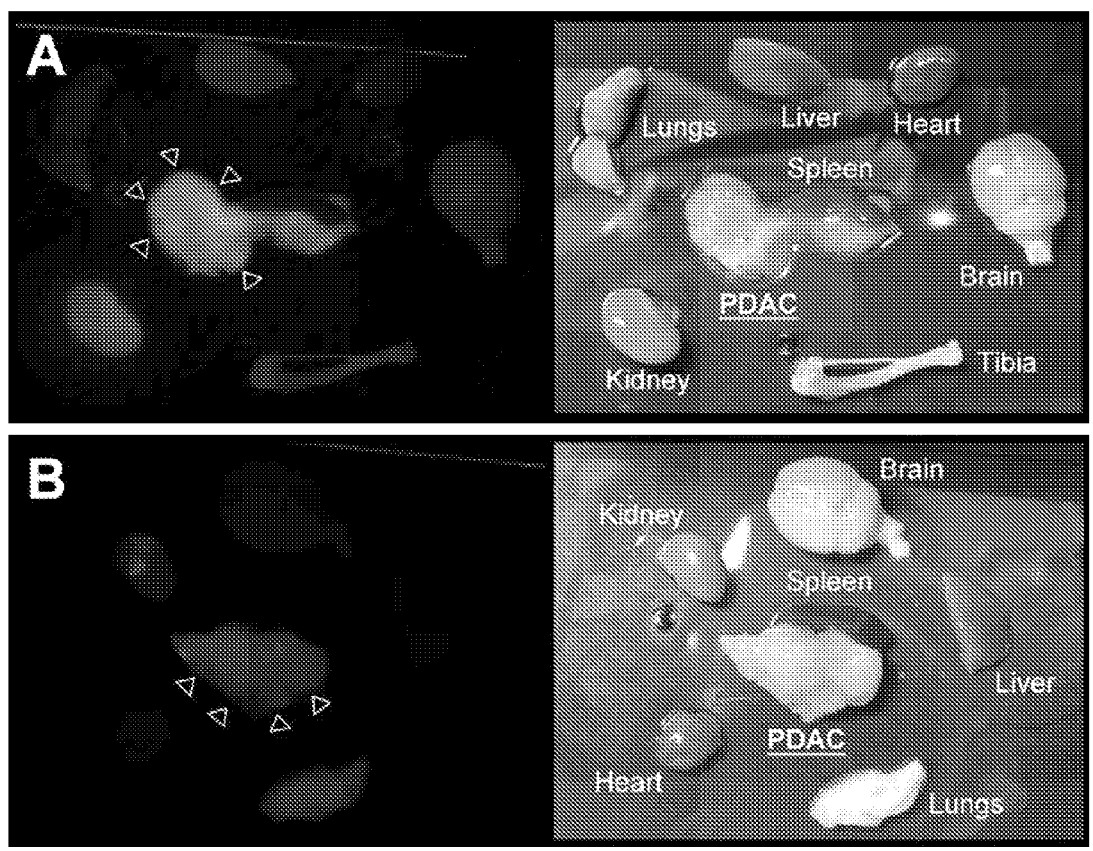
FIGS. 3A and 3B show tumor homing of iRGD1 peptide into murine pancreatic carcinoma. A, 200 μg of fluorescamine-labeled iRGD1 peptide was injected through the tail vein into transgenic mice with pancreatic ductal adenocarcinoma (PDAC) and the peptide was allowed to circulate for 4.5 hrs. B, An excess of non-labeled iRGD1 (2 mg/mouse) was injected into the PDAC mice 30 min prior to the injection of the fluorescamine-labeled iRGD1 peptide as described in A. Shown are harvested organs observed under UV light (left) and white light (right).
Figure 4:
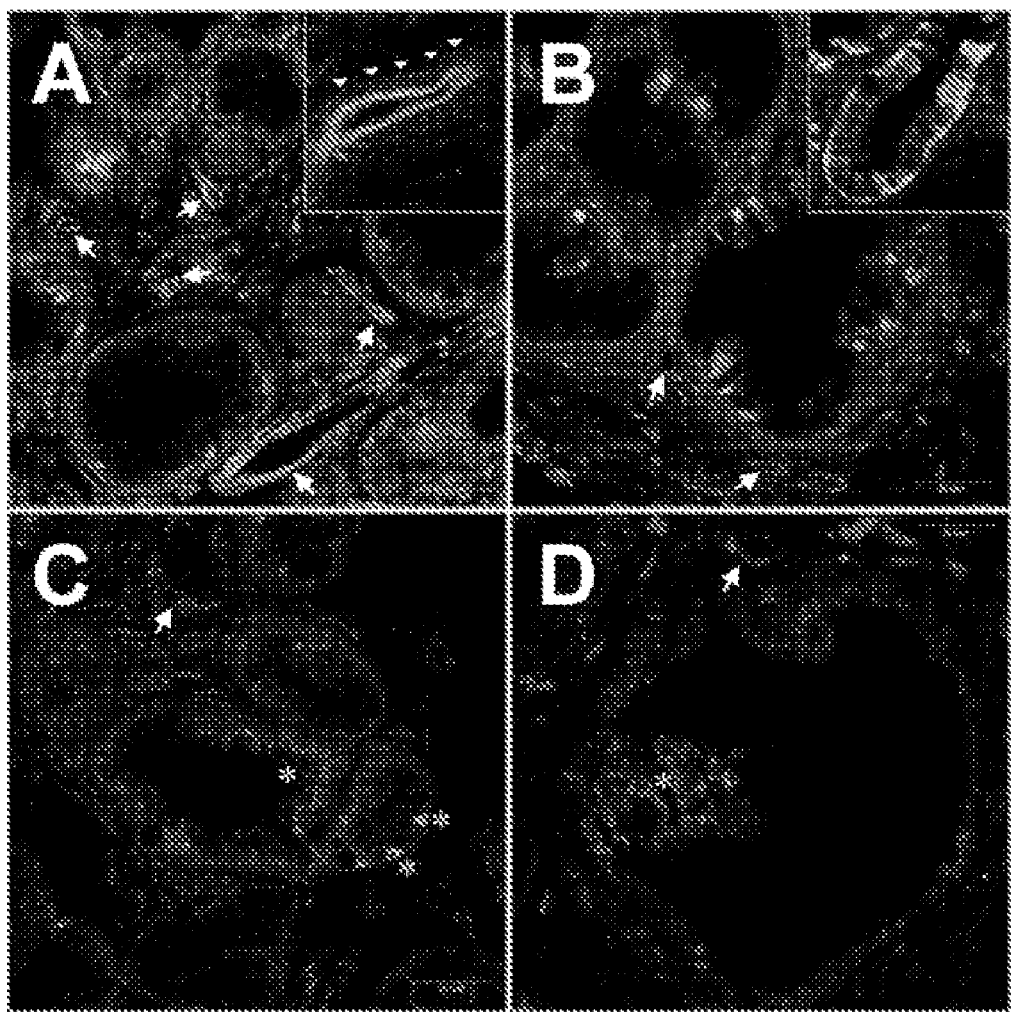
FIGS. 4A, 4B, 4C and 4D show the time-dependent in vivo homing patterns of FAM-iRGD peptide in PDAC lesions. Approximately 200 μg of FAM-iRGD1 was injected into mice bearing PDACs and allowed to circulate for 15 min (A), 30 min (B), 2 hrs (C) and 4.5 hrs (D). The nuclear staining with DAPI and vascular endothelial cell staining with an anti-CD31 antibody, respectively are shown. Note that at 15 (A) to 30 min (B) post-injection of FAM-iRGD1, the dye stays in the vessels (arrows) or in the cells surrounding the vessels (A, arrowheads in window at the right upper corner), but no vascular staining with the peptides is observed after 2 hrs (C, arrow) or 4.5 hrs (D, arrow). At 30 min post peptide injection, the peptide fluorescence appears in tumor glands (B, main panel and upper right corner inset); some individual cells within the tumor are strongly positive after 2 hrs (C, asterisks) and 4.5 hrs (D, asterisk).

Tumor homing of the iRGD sequences identified in phage display was confirmed by studying the ability of the iRGD1 peptide to home to tumors. Approximately 200 μg of fluorescamine-labeled iRGD1 peptide (FAM-iRGD1) was injected through the tail vein into immuno-deficient mice bearing xenograft of PPC1 human prostate carcinoma, MIA PaCa-2 human pancreatic carcinoma, or MDA-MB-435 human breast carcinoma and was allowed to circulate for 4.5 hrs (FIG. 2). Examination of harvested organs under UV light showed that the tumors of the iRGD-injected mice were strongly fluorescent, whereas normal tissues were not. Similar results were obtained when FAM-iRGD1 was injected into transgenic mice bearing spontaneous pancreatic ductal adenocarcinoma (PDAC) tumors (Bardeesy and DePinho, 2002) (FIG. 3A). Co-injecting an excess of unlabeled iRGD1 peptide inhibited the accumulation of the FAM-iRGD1 in the PDAC tumors, demonstrating specificity of the iRGD1 homing (FIG. 3B). Confocal microscopy of PDAC tumor sections from animals injected with FAM-iRGD1 indicated time-dependent in vivo homing dynamics for this peptide. The peptide initially accumulated in tumor vessels (FIG. 4A, arrows), then in the cells surrounding the vasculature (FIG. 4A, arrowheads), and after 30 min shifted to tumor cells in tumor glands (FIG. 4B). By this time only a faint trace in the vasculature was seen (FIG. 4B, arrows) and no vessel fluorescence was seen at the later time points studied (FIGS. 4C and D). The peptide fluorescence associated with the tumors cells was condensed into the perinuclear area of the tumor cells (FIGS. 4C and 4D, asterisks). These observations show that iRGD target both tumor vessels and tumor cells, and that it accumulates within tumor cells.

iii. Internalization of iRGD into Tumor Cells

Figure 5:
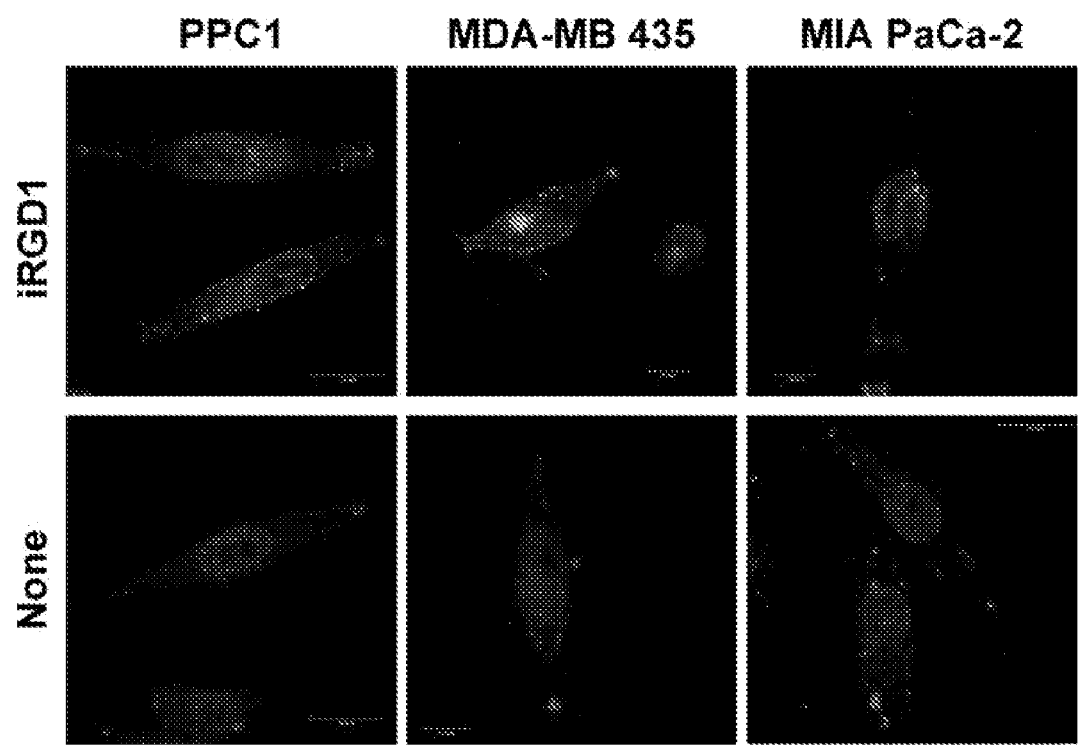
FIG. 5 shows internalization of iRGD1 peptide into tumor cells in vitro. PPC1, MDA-MB-435, and MIA PaCa-2 cells cultured on cover slips coated with type I collagen were incubated with 10 μM fluorescamine-iRGD1 for 2 hours at 37° C., stained with a plasma membrane marker and nuclear stain DAPI, and imaged under a confocal microscope.
Figure 6:
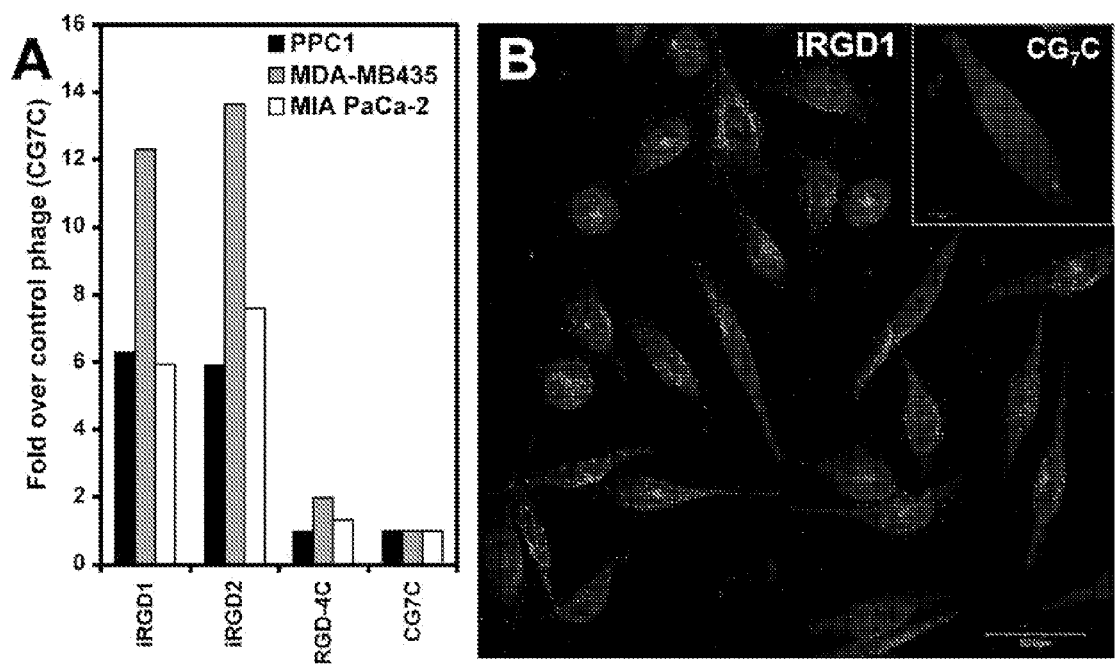
FIGS. 6A and 6B show internalization of iRGD phage into tumor cells. A, T7 phage displaying iRGD peptides, RGD-4C(CDCRGDCFC, SEQ ID NO: 4), or CG7C (control phage) were incubated with various tumor cell lines at 37° C. for 30 min. Phage bound to the cell surface were removed by washing the cells with a acidic buffer, and internalized phage were rescued and titrated. The internalization of iRGD phage is markedly more efficient that that of RGD-4C(CDCRGD-CFC, SEQ ID NO: 4). B, T7 phage displaying iRGD peptides (main panel) or CG7C control peptides (right upper window) were incubated with PPC1 cells cultured on coverslips coated with type I collagen for 2 hours at 37° C., stained with anti T7 antibody, a plasma membrane marker and DAPI to visualize the nuclei, and imaged by a confocal microscope. Note that iRGD phage extensively internalizes into the tumor cells, whereas the control phage (inset) does not.
Figure 7:
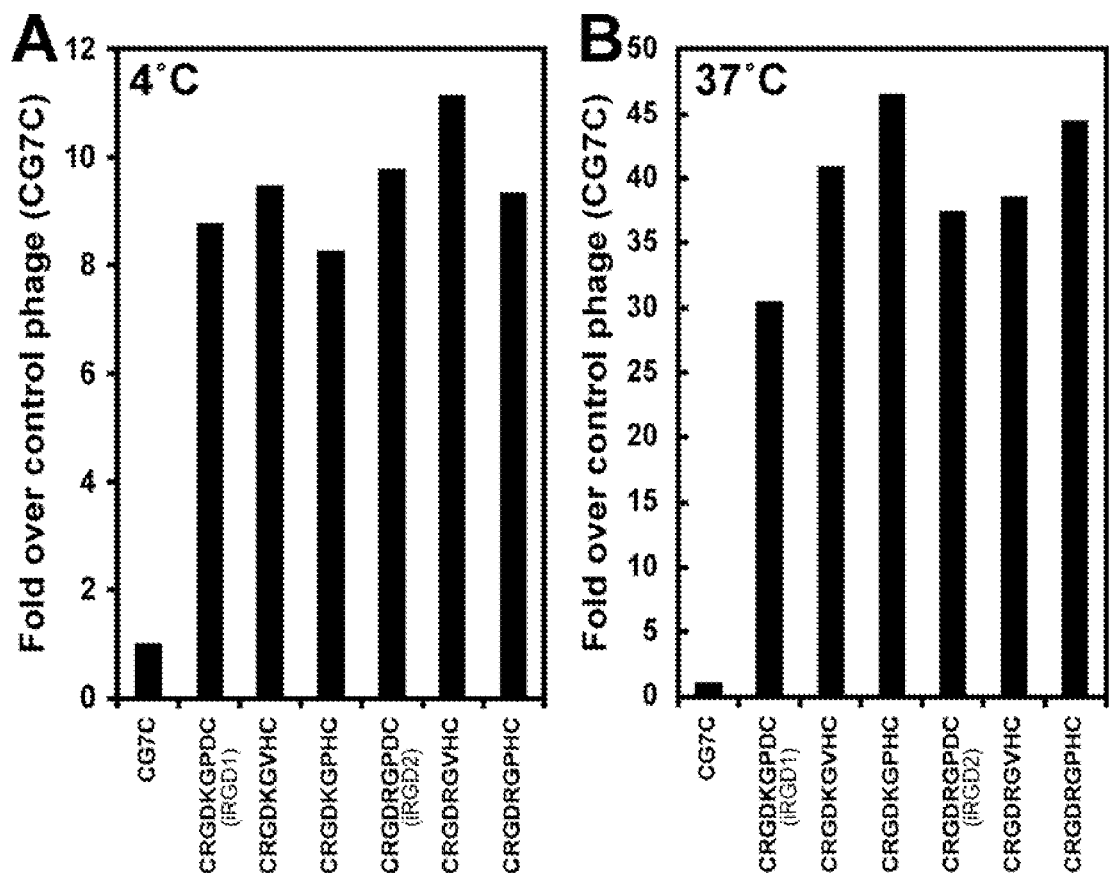
FIGS. 7A and 7B show the binding (A) and internalization (B) of phage displaying CG7C (control phage), or examples of iRGD variants that were seen in the screening (SEQ ID NOs:1, 106, 302, 2, 262, and 303). PPC1 cells were incubated with the phage for 1 hour at 4° C. (A) or 37° C. (B). Phage that bound to the cell surface (A) or those that had internalized into the cells (B) were rescued for titration.
Figure 8:
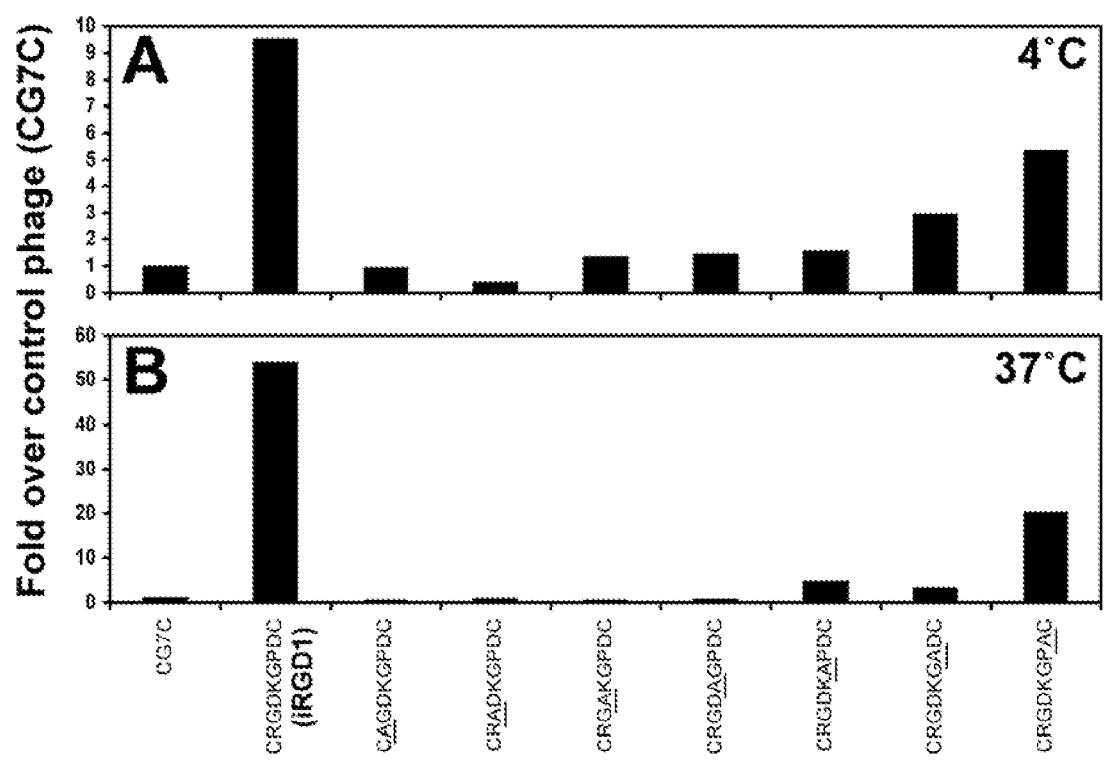
FIGS. 8A and 8B show the binding (A) and internalization (B) of phage displaying CG7C (control phage), iRGD1, and iRGD1 mutants that carry an alanine substitution for each amino acid (underlined) (SEQ ID NOs:1 and 304-310). PPC1 cells were incubated with the phage for 1 hour at 4° C. (A) or 37° C. (B). Phage that bound to the cell surface (A) or those that internalized into the cells were rescued for titration. Note that an alanine mutation of any one of the 5 residues among R, G, D, K, and G eliminates or greatly reduces the binding and internalization of iRGD phage to the tumor cells.
Figure 9:
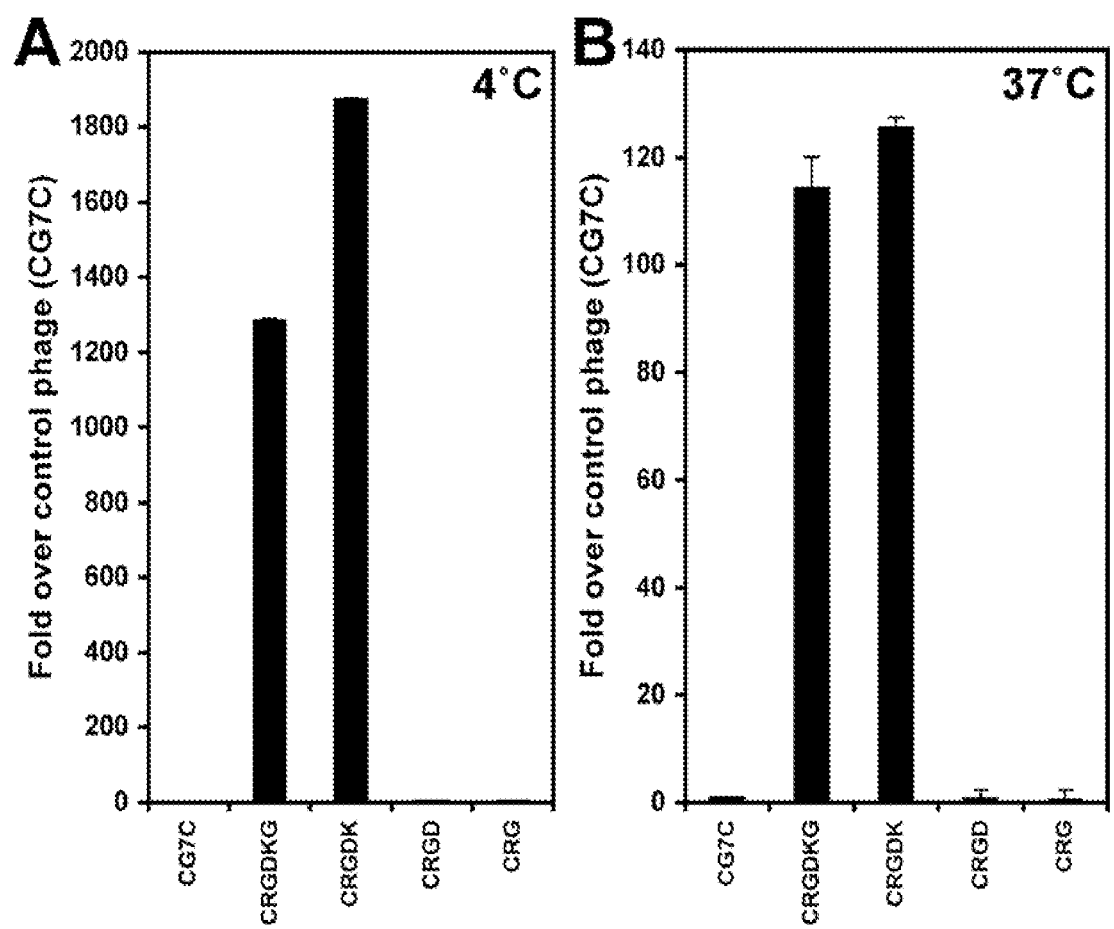
FIGS. 9A and 9B show the binding (A) and internalization (B) of phage displaying CG7C (control phage), CRGDKG, CRGDK, CRGD, or CRG (SEQ ID NOS: 5-8, respectively). PPC1 cells were incubated with the phage for 1 hour at 4° C. (A) or 37° C. (B). Phage that bound to the cell surface (A) or those that had internalized into the cells were rescued for titration.

The notion that the iRGD peptides internalize into tumor cells was confirmed by confocal microscopy. When various types of tumor cells were incubated with FAM-iRGD1 for 2 hours at 37° C., peptide fluorescence accumulated within the cells (FIG. 5). In addition, iRGD phage also became internalized into tumor cells, and the internalization was much more extensive than that of phage displaying other RGD peptides such as RGD-4C(CDCRGDCFC, SEQ ID NO: 10) or CG7C control peptide (FIG. 6). Thus, iRGD can cause internalization of a simple chemical compound (fluoresceine) as well as of a nanoparticle (the T7 phage is a nanoparticle with a diameter of about 50 nm). Certain variants of iRGD, such as CRGDKGPDC, CRGDRGPDC, or CRGDKGPEC (SEQ ID NOS: 1, 2, and 3, respectively) showed similar tumor cell binding and internalization as CRGDKGPDC (FIG. 7. SEQ ID NO: 1), suggesting that the critical motif of iRGD lies in the 5 amino acids, RGDK/RG. To identify the motif in iRGD, two experiments were performed. First, an alanine scan of iRGD was carried out. Mutating any one of the 5 residues among R, G, D, K, or G into an alanine eliminated or greatly reduced the internalization of the iRGD phage (FIG. 8). Second, phage displaying CRGDKG, CRGDK, CRGD, or CRG (SEQ ID NOS: 5-8), were constructed and tested for their ability to bind and internalize to tumor cells (FIG. 9). CRGDKG and CRGDK (SEQ ID NOS: 5 and 6) phage both bound and internalized to tumor cells while CRGD and CRG did not. Collectively, these results suggest that the critical motif of iRGD consists of RGDK/R (SEQ ID NOS: 11 and 12).

iv. Receptors for iRGD

Figure 10:
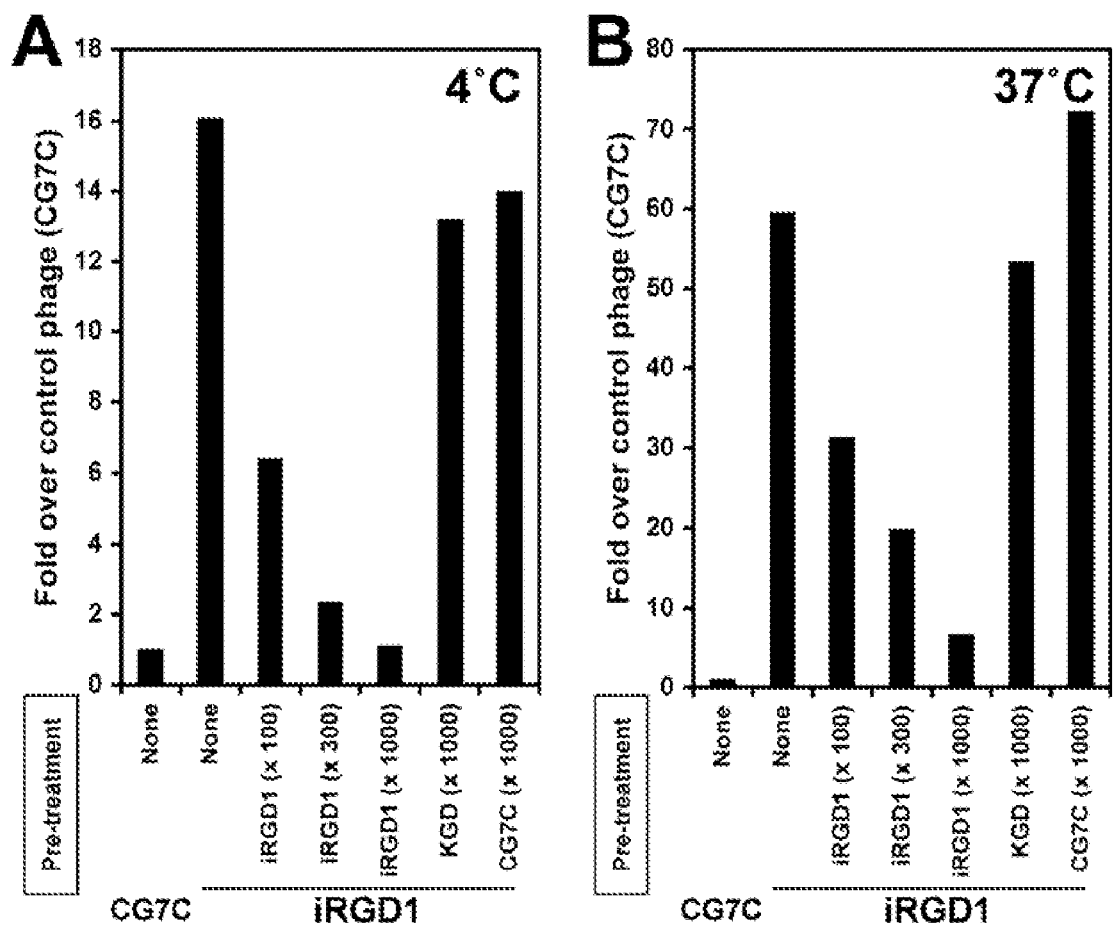
FIGS. 10A and 10B show inhibition of iRGD1 phage binding to tumor cells (A) and internalization into them (B) by UV-inactivated phage displaying series of peptides. A, PPC1 cells were pre-treated with 100-1000 fold excess of UV-inactivated phage displaying iRGD1, KGD (CKGDKGPDC, SEQ ID NO: 9), or CG7C (control phage), followed by co-incubation with active iRGD phage or CG7C phage for 1 hour at 4° C. Phage that bound to the cell surface were titered. B, PPC1 cells were treated as described in A except that they were co-incubated with iRGD1 or CG7C phage at 37° C. The internalized phage were rescued for titering as described in the legend for FIG. 5A.

The binding and internalization of iRGD phage to PPC1 human prostate cancer cells were dramatically inhibited by UV-inactivated iRGD phage in a dose-dependent manner but not by UV-inactivated phage expressing CG7C control peptide or KGD (CKGDKGPDC, SEQ ID NO: 1) peptide, suggesting a receptor-mediated mechanism involved in the binding and internalization of iRGD to the tumor cells (FIG. 10).

The RGD motif is an integrin recognition sequence, and RGD-directed integrins, such as αVβ3, αVβ5, and α5β1, are known to be upregulated in angiogenic endothelial cells and certain tumor cells (Elicieri and Cheresh, 2001; Ruoslahti, 2002). Hence, the effect of antibodies against RGD-directed integrins on the tumor cell binding an internalization of iRGD were tested.

Figure 11:
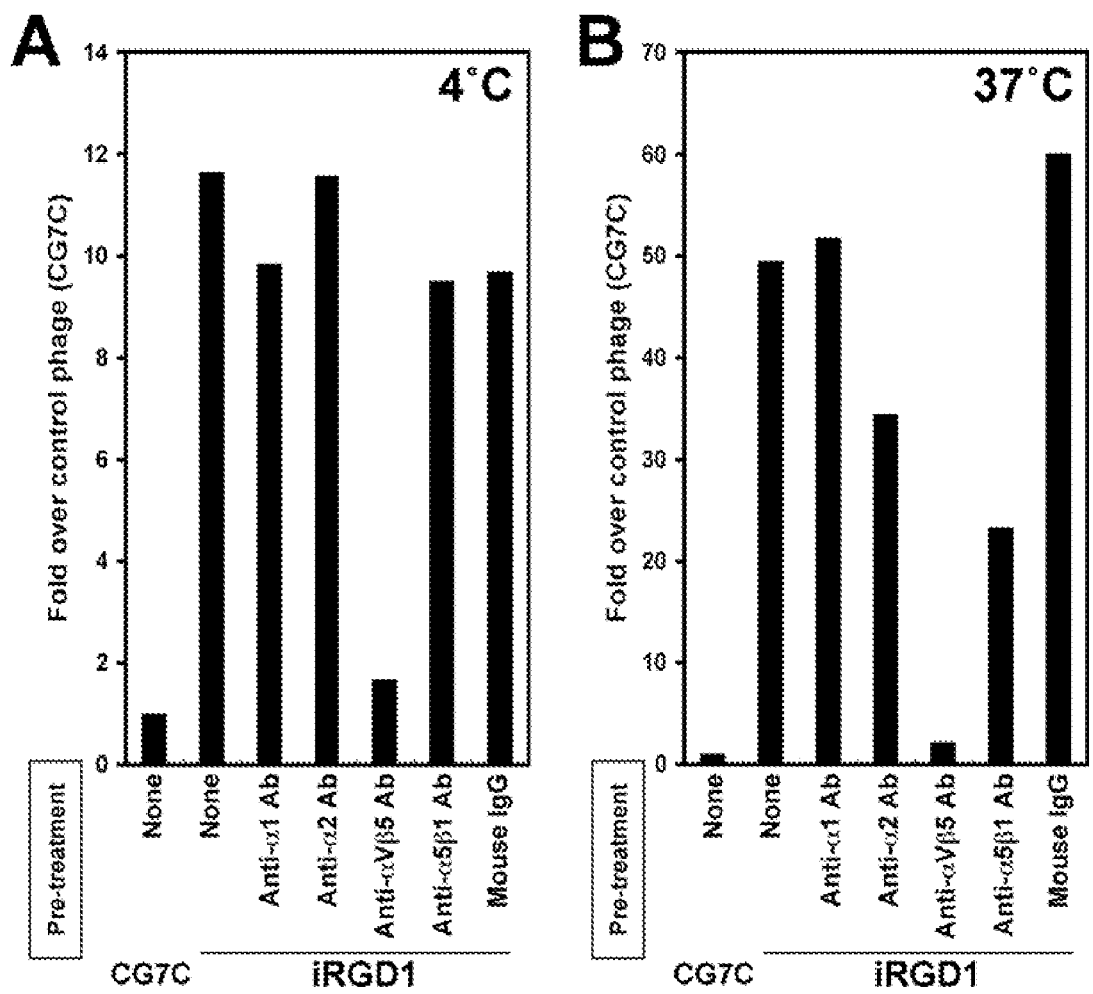
FIGS. 11A and 11B show inhibition of iRGD1 phage binding (A) and internalization (B) by series of anti-integrin antibodies. A, PPC1 cells were pre-treated with or without series of anti-integrin antibodies, or with normal mouse IgG as a control, for 30 min at 4° C., followed by incubation with iRGD1 phage or CG7C control phage for 1 hour at 4° C. (A) or 37° C. (B). Phage that bound to the cell surface (A) or those that internalized into the cells (B) were rescued and titrated. A function-blocking antibody against the αV integrin subunit efficiently inhibits both the binding and internalization of the iRGD1 phage.

As shown in FIG. 11, an antibody against the αVβ5 integrin abolished the binding of iRGD phage and peptide to the PPC1 prostate cancer cells and the subsequent internalization of the phage by these cells. In contrast, anti-α5β1 had only a slight effect on the iRGD internalization. Thus, one or more αV integrins serve as one receptor for iRGD. However, given the remarkable internalization efficacy of iRGD, and the fact that other anti-integrin antibodies such as anti-α2 and anti-α5β1 antibodies show some inhibitory effects against the internalization of iRGD, αV integrin binding is unlikely to completely explain the unique potency of iRGD in tumor homing. The iRGD sequence contains a consensus cleavage site for furin-type proteases (RXX(K/R); SEQ ID NOS: 13 and 14; Thomas, 2002). Furins are a large proteolytic enzyme family, the members of which are often expressed in a cell type-specific manner. It is speculated that, subsequent to the binding of iRGD to integrins in tumors, a proteolytic cleavage selective for the RGD(K/R) (SEQ ID NO: 11 and 12) sequence somehow promotes the internalization of the peptide and its payload. The internalization in turn causes accumulation of iRGD in the target cells, making iRGD particularly effective as a homing peptide.

Table 1 shows the sequencing results from the in vivo phage display (marked by an asterisk in FIG. 1) and the round 4 of ex vivo phage display (double asterisks in FIG. 1) performed on bone xenografts of human prostate cancers. The sequences in lowercase and not underlined were common to bone tumors and normal bones, and were eliminated. The sequences in uppercase and double underlined show iRGD and its variants, and those in uppercase and not underlined had motifs related to iRGD. Note that number of iRGD bearing phage appeared in independent screenings. Amino acid sequences of four amino acids or longer are SEQ ID NOs:15 to 289, left to right then top to bottom.

TABLE 1

| Screening 1 | |
|---|---|
| after in vivo | after last ex vivo |
| crstranpc | cssvanelc |
| clpvnqn-c | cqnqalnic |
| cevgqnaic | cqrgdspdc |
| cgengltvc | crsqdndic |
| – | cnnevnsvc |
| ceaeglvlc | casgenqvs |
| cpdqglkfc | cdlmsnelc |
| ssvdklaaale | cdnpfdpsc |
| crggnevec | ceadglsic |
| cmldpskpc | cespfeddc |
| cqrgdalpc | ctgdrrgdc |
| cerdgndic | CRGDKGENC |
| ckktgnrgc | ckaxenhic |
| ctmdgneic | csdsltvc |

TABLE 1-continued

| | |
|---|---|
| cgrgdnlqc | cadstvdgc |
| crndvsadc | cqtgnnmvc |
| clkppr-hc | ctpegltic |
| cpmdqnsic | cqtgqnnvc |
| cadqtltic | csmdenelc |
| ? | ckadgltvc |
| cmnnvemnc | cvsndvqhc |
| ckngeasqgc | cqsndiatc |
| crstrsspc | arvlrsgsaklaaale |
| cigntnniec | cgmsgneic |
| ckppr-rsc | cdtkppr-c |
| celasltic | ckppgliaklslrthlts |
| cltlcd-yc | csgtsrgdc |
| cdgkqnrac | cdltgndvc |
| a- | crppr-rvc |
| cdnllp-ac | cslndic |
| casaglvvc | cnpkppr-c |
| cmnevnakc | ctkppr |
| argpr-isc | cengsltlc |
| cdgnns-rc | cgkpar-kc |
| cenrvdgdc | cskppr-gc |
| cvkqkplic | cskppr-sc |
| argpr-isc | cndlsgc |
| cdtkppr-c | CRGDKGPDC |
| ctneingtc | cdiganmvc |
| cskppr-hc | CRGDKGPDC |
| chdgsltvc | calegnavc |
| ckk-pyksc | cqvdlntic |
| cslsndvdc | CRGDKGPDC |
| ckdnnl-ic | casdgltvc |
| cvkpar-gc | csaeglvvc |
| cnevvcr-c | clgdgvhic |
| crpar-plc | casdgltvc |
| CRGDKGVHC | ctdggltvc |

| Screening 2 | |
|---|---|
| after in vivo | after last ex vivo |
| clvisgdsc | cgpnsltvc |
| cdprydnac | crstrsspc |
| cstdsltic | csnagltvc |
| csgqddnac | clgtgrggc |

| | |
|---|---|
| clsfepc-c | cgkppr--c |
| ckgqslvvc | crstrntec |
| cdpaldnsc | crddgitic |
| cgddslric | cpaggltvc |
| cregsltvc | crppr-arc |
| casgkrgdc | csanslvvc |
| cegeglilc | cnwagnevc |
| cgsdqlhvc | cvgdgnaic |
| cegknltic | csasggprc |
| cgsdglkic | crppr-qhc |
| cqevgagtc | CRGDKHADC |
| cdgssltvc | crppr-pnc |
| cqrgdkpqc | cgrgdmpsc |
| cgadgltvc | gqldslvvc |
| cpsnsltvc | cvgdglqfc |
| cgpdalvlc | cdaeglvlc |
| CRGDKGPDC | cyrkneiec |
| crgdkgvgc | cnslnigsc |
| cksdglkic | cstryrsrc |
| cdgnglnic | cgrterkvc |
| cgedgltvc | CRGDHAANC |
| clvfesqkc | crptratnc |
| cegtgltic | cnmegltvc |
| csadgltvc | cdgngltvc |
| csadglmvc | ceydaltvc |
| ccdk-vktc | cnalhlesc |
| cqrgddktc | cgsggltvc |
| cpsdslalc | cdnglvlc |
| crptrnypc | ctkppr-gc |
| cmqeglnic | crgdaginc |
| csrgslkic | catnsltvc |
| cqetglnic | CRGDKGPEC |
| ceigdnvvc | cgpgaltvc |
| cassgltic | crgdsplscklaaale |
| cmsgtltvc | cltfgkdkc |
| — | cvqrpar-c |
| cdmtsltvc | cgsgsltvc |
| cqrgdafpc | casssltic |
| caanplvlc | CRGDKGPEC |
| cltiggtsc | cekrgdslc |

TABLE 1-continued

| | |
|---|---|
| csgkglnic | caddaltfc |
| cvgsltvc | cnslnigsc |
| cddeglnlc | cgskslvlc |
| crgeeltic | ckdyqitvc |

Screening 3

| after in vivo | after last ex vivo |
|---|---|
| stop | CRGDKGPEC |
| crtrsgqkc | arvlrsgsaklaaale |
| cevgtrldc | cqrqdnlpc |
| cslednavc | cmsdqrdrc |
| csnapnkrc | argslrvsaklaaale |
| clrsdqasc | clkdqrsac |
| ssvdklaaale | cladqrakc |
| clkdqrpac | mlgdpnparrrvg |
| canatyeac | cvdsndvsc |
| ckqtrnttc | mlgdpnparrrvg |
| cdgvv-lsc | CRGDHGVEC |
| h | cseqgitic |
| crstrsktc | cqkrqdsic |
| asrmggvgaklaaale | CRGDKGPDC |
| ceptaknnc | clndqrpac |
| cllqskndc | cksnptqrc |
| ssvdklaaale | CRGDKGPDC |
| ckatrstkc | CRGDRGPDC |
| CRGDKPLGC | cinspsadc |
| csrqgedpc | CRGDHAGDC |
| ssvdklstdytan | ctqrqdalc |
| cprdsnnvc | aglrgsisaklaaale |
| cvrrqdsac | CRGDRGPDC |
| ckgsrnlnc | cqrqdnlac |
| crq-valgc | caqsnrldc |
| cenwektsc | sgmvlrssaklaaale |
| stop | agrvlrssaklaaale |
| ctph-ahpc | CRGDKGPDC |
| stop | CRGDKGPDC |
| agrvlrssaklaaale | agrvlrssaklaaale |
| agggvrslaklaaale | CRGDKGPDC |
| stop | crgdkavgc |
| CRGDRGVHC | clqdqrakc |
| cvvqvsrkc | cekrqdnlc |
| ssvdklaaale | mlgdpnparrrvg |
| cg | cql-lvvsc |
| arvslrgsaklaaale | CRGDKGPEC |
| c-rsdrwfc | a stop |
| clpqsdakc | cekrqdsvc |
| cqqskklac | CRGDHAGDC |
| stop | CRGDKTTNC |
| crasqakkc | cqvaprdkc |
| ssvdklaaale | csqrqdslc |
| canadrvtc | cekrqdsvc |
| sgmvlrssaklaaale | CRGDRGPDC |
| avrvgvraklaaale | crqdsac |
| ar | cgneiadkc |
| cee--grrc | agvrmgrgaklaaale |

B. Example 2

Analysis of iRGD Homing and Internalization

Peptides containing the RGD integrin recognition motif (Pierschbacher and Ruoslahti, E. Cell attachment activity of fibronectin can be duplicated by small synthetic fragments of the molecule. *Nature* 309, 30-33 (1984); Ruoslahti, The RGD story: a personal account. *Matrix Biol.* 22, 459-465 (2003)) and its mimics have been used to deliver drugs, biologicals, imaging agents, and nanoparticles to αv-integrins expressed in tumor blood vessels (Eliceiri and Cheresh, Adhesion events in angiogenesis. *Curr. Opin. Cell Biol.* 13, 563-568 (2001); Ruoslahti, Specialization of tumor vasculature. *Nature Rev. Cancer* 2, 83-90 (2002); Arap et al., Cancer treatment by targeted drug delivery to tumor vasculature in a mouse model. *Science* 279, 377-380 (1998); Curnis et al., Coupling tumor necrosis factor-α with $α_v$ integrin ligands improves its antineoplastic activity. *Cancer Res.* 64, 565-571 (2004); Sipkins et al., Detection of tumor angiogenesis in vivo by $α_vβ_3$-targeted magnetic resonance imaging. *Nature Med.* 4, 623-626 (1998); Murphy et al., Nanoparticle-mediated drug delivery to tumor vasculature suppresses metastasis. *Proc. Natl. Acad. Sci. USA* 105, 9343-9348 (2008)). However, a major obstacle has been the limited capability of such RGD-targeted agents to penetrate tumor parenchyma and accumulate therein (Jain, Vascular and interstitial barriers to delivery of therapeutic agents in tumors. *Cancer Metastasis Rev.* 9, 253-266 (1990)), despite evident expression of the target integrins. Disclosed is a cyclic RGD peptide, iRGD (sequence: CRGD(K/R)GP(D/E)C; SEQ ID NOs:1, 2, 3, and 290) that is exceptionally effective in orchestrating extravasation and spreading of linked payloads within tumor tissue, and subsequently internalizing within tumor cells. The peptide incorporates two functional elements: the RGD motif that gives tumor specificity (Pierschbacher and Ruoslahti, E. Cell attachment activity of fibronectin can be duplicated by small synthetic fragments of the molecule. *Nature* 309, 30-33 (1984); Ruoslahti (2003); Eliceiri and Cheresh (2001); Ruoslahti (2002); Arap et al. (1998); Curnis et al. (2004); Sipkins et al. (1998); Murphy et al. (2008)), and an RXX(K/R) motif (CendR motif; SEQ ID NOs:13 and 14) that mediates penetration. iRGD readily adhered to cultured cells expressing αv integrins, and was internalized far more effectively than other RGD peptides. Internalization was dependent on expression of neuropilin-1, the receptor for the CendR motif. In all seven tumor models tested, iRGD coupled to a payload of fluorescein, phage, or artificial nanoparticles, accumulated around tumor vessels in vivo, spread through the tumor interstitium, and became internalized within tumor cells. Systemic administration of iRGD micelles labelled with a near infrared dye produced a strong and specific tumor signal in whole body imaging of mice. The tissue-penetrating properties of iRGD present a new tool for synaphic (docking-based) tumor targeting of nanoscale payloads for diagnostic imaging and therapy.

Mouse models of prostate cancer were used as targets in phage library selection (Hoffman et al., Progressive vascular changes in a transgenic mouse model of squamous cell carcinoma. *Cancer Cell* 4, 383-391 (2003)) to identify peptides that bind to tumor blood vessels. Phage that contained the RGD motif (Pierschbacher and Ruoslahti (1984); Ruoslahti (2003)) within three related sequences, CRGDKGPDC (SEQ ID NO:1), CRGDRGPDC (SEQ ID NO:2), and CRGDKGPEC (SEQ ID NO:3), dominated in the selected pools (Table 2). CRGDKGPDC ("iRGD" for 'internalizing-RGD'; SEQ ID NO:11 was most frequent and was chosen for further analysis.

TABLE 2

RGD peptides selected in the screenings

| Screening 1 | | Screening 2 | | Screening 3 | |
|---|---|---|---|---|---|
| Sequence | (%) | Sequence | (%) | Sequence | (%) |
| CRGDKGPDC | 15.2 | CRGDKGPDC | 13.6 | CRGDKGPEC | 10.0 |
| CRGDRGPDC | 9.1 | CRGDKGENC | 4.5 | CRGDKHADC | 5.0 |
| CRGDKGPEC | 6.1 | CGRGDSPDC | 4.5 | CRGDHAANC | 5.0 |
| CRGDKTTNC | 3.0 | | | CRGDAGINC | 5.0 |
| CRGDHAGDC | 6.1 | | | CGRGDMPSC | 5.0 |
| CRGDHGVEC | 3.0 | | | CEKRGDSLC | 5.0 |
| CGRGDNLPC | 3.0 | | | | |
| CGRGDNLAC | 3.0 | | | | |
| CEKRGDNLC | 3.0 | | | | |
| CEKRGDSVC | 6.1 | | | | |
| CSGRGDSLC | 3.0 | | | | |
| CGKRGDSIC | 3.0 | | | | |
| CTGRGDALC | 3.0 | | | | |
| CRGDSAC | 3.0 | | | | |
| Total RGD peptides | 69.6 | Total RGD peptides | 22.6 | Total RGD peptides | 35.0 |

Figure 12:
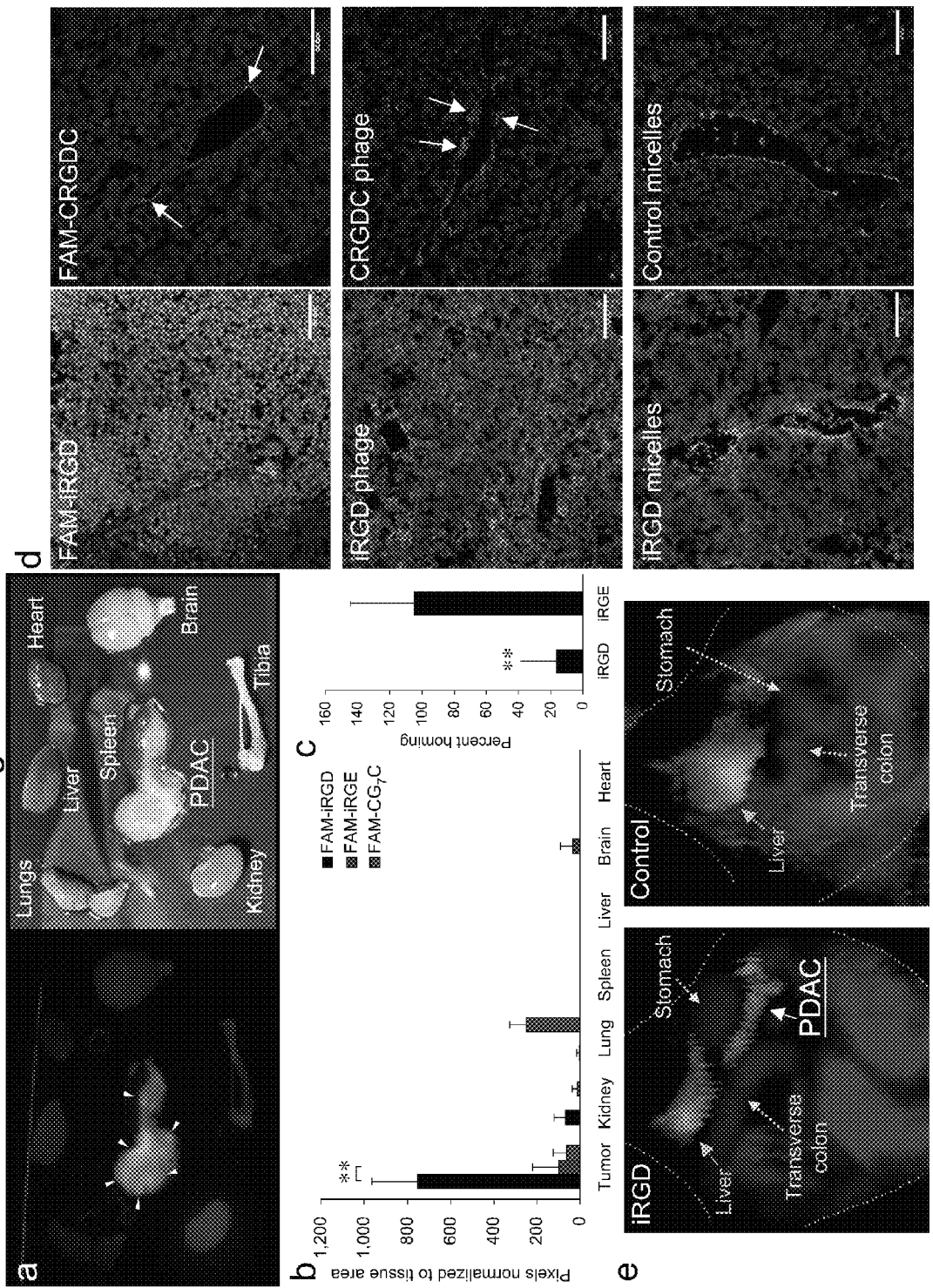
FIGS. 12A-12E show in vivo tumor homing of iRGD peptide. a, Approximately 200 μg of FAM-iRGD or control peptide in PBS was intravenously injected into LSL-Kras, p53-fl/+, p48-Cre mice bearing de novo pancreatic ductal adenocarcinoma (PDAC) (Bardeesy and DePinho, Pancreatic cancer biology and genetics. Nature Rev. Cancer 2, 897-909 (2002)). The peptides were allowed to circulate for 2 hrs and organs were collected and viewed under UV light (left panel) or white light (right panel). Arrowheads point to the tumors. b, c, Quantification of the in vivo distribution of iRGD and control peptides. FAM-iRGD; a non-integrin-binding iRGD mutant, FAM-CRGEKGPDC (SEQ ID NO:291) (FAM-iRGE); and a FAM-labelled cyclic polyglycine peptide (FAM-CG$_7$C) were injected into PDAC mice (Bardeesy and DePinho, Pancreatic cancer biology and genetics. Nature Rev. Cancer 2, 897-909 (2002)) as described elsewhere herein (b). In some cases, a 10-fold excess of unlabelled iRGD peptide or iRGE peptide was injected 30 min before FAM-iRGD (c). Fluorescence in each tissue was quantified with Image J software. Statistical analysis was performed with Student's t-test. FAM-iRGD homing without injection of unlabelled peptide was considered as 100% in c. n=3; error bars, s.d.; double asterisk, p<0.01. d, Confocal images of orthotopic 22Rv-1 human prostate cancer xenografts from mice injected with the indicated peptides, phage, and micelles. iRGD was compared to a similar integrin-binding but non-internalizing peptide, CRDGC (SEQ ID NO:301). The circulation time for the free peptides was 2 hrs, 15 min for the peptide-displaying phage, and 3 hrs for the peptide-coupled micelles. Arrows point to FAM-CRGDC (SEQ ID NO:292) peptide or CRGDC (SEQ ID NO:292) phage in or just outside the vessel walls, illustrating its homing to the tumor vasculature but not dispersion and internalization. Representative fields from multiple sections of each of three tumors are shown. Scale bars=50 μm. e, Whole body imaging of PDAC mice (Bardeesy and DePinho (2002)) injected with FAM-iRGD micelles or FAM control micelles labelled with Cy7. Images were taken 3 hrs after the injection of the micelles. Only the shaved areas of the skin delineated by the dotted lines are shown. Light staining, 800 nm (Cy7); darker staining, 700 nm (background fluorescence). The saw tooth appearance of the fluorescent organs is caused by the mouse's breathing.
Figure 16:
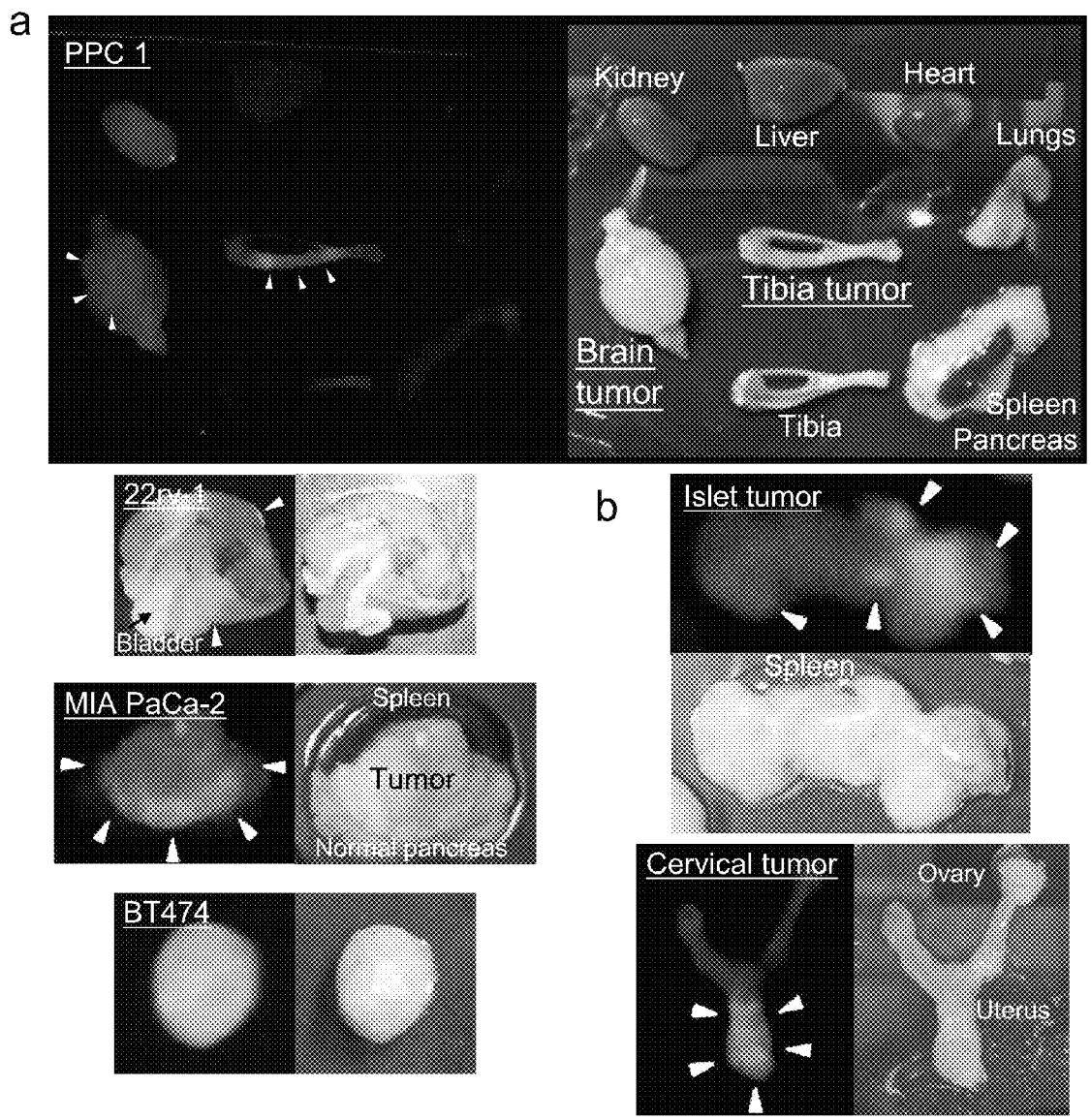

Forty-eight individual clones were randomly picked for sequencing from phage pools recovered in the final round of ex vivo phage display. Clones that gave unsuccessful sequencing results (less than 5%) were omitted during the analysis. The proportion of each RGD peptide is shown.

iRGD was synthesized as a fluorescein-labelled peptide (FAM-iRGD) and intravenously injected the peptide into tumor-bearing mice. FAM-iRGD accumulated in tumor tissue in each tumor model tested. The tumors, but not normal tissues, were strongly fluorescent under UV light (FIGS. 12A, 12B, and 16). Control peptides produced only minimal tumor fluorescence (FIG. 12B). Co-injecting an excess of unlabelled iRGD peptide greatly reduced the accumulation of FAM-iRGD in tumors, whereas a non-integrin binding (Pierschbacher and Ruoslahti (1984); Ruoslahti (2003)) variant, CRGEKGPDC (iRGE; SEQ ID NO:291), did not have the same effect (FIG. 12C). These results show that iRGD specifically targets tumors and that its RGD motif is critical for the targeting.

Confocal microscopy revealed accumulation of FAM-iRGD peptide in and around tumor vessels and in tumor parenchyma (FIG. 12D), but not in normal tissues. Remarkably, iRGD phage (diameter about 50 nm) and another iRGD-coated nanoparticle, self-assembling micelles (diameter 15-25 nm) (Karmali et al., Targeting of albumin-embedded paclitaxel nanoparticles to tumors. *Nanomedicine* in press (2008); Arleth et al., Detailed structure of hairy mixed micelles formed by phosphatidylcholine and PEGylated phospholipids in aqueous media. *Langmuir* 21, 3279-3290 (2005)), also reached extravascular tumor parenchyma (FIGS. 12D and 17). Two other RGD peptides and corresponding phage, CRGDC (SEQ ID NO:292) and RGD-4C (SEQ ID NO:293), which have a strong affinity for αv integrins (Koivunen et al., Selection of peptides binding to the $α_5β_1$ integrin from phage display library. *J. Biol. Chem.* 268, 20205-20210 (1993); Koivunen et al., Phage libraries displaying cyclic peptides with different ring sizes: ligand specificities of the RGD-directed integrins. *Biotechnology (N Y)* 13, 265-270 (1995)), also homed to tumors, but accumulated only in and around tumor blood vessels and did not disperse throughout the interstitium like iRGD (FIGS. 12D and 17).

Whole body imaging of mice injected with FAM-iRGD micelles labelled with the near-infrared dye, Cy7, produced a strong and specific signal from the tumors, illustrating the ability of iRGD for tumor targeting (FIG. 12E). The internalizing properties of the iRGD, and its apparent spreading into tumor tissue, prompted study of the mechanisms underlying these unique activities of iRGD.

Figure 13:
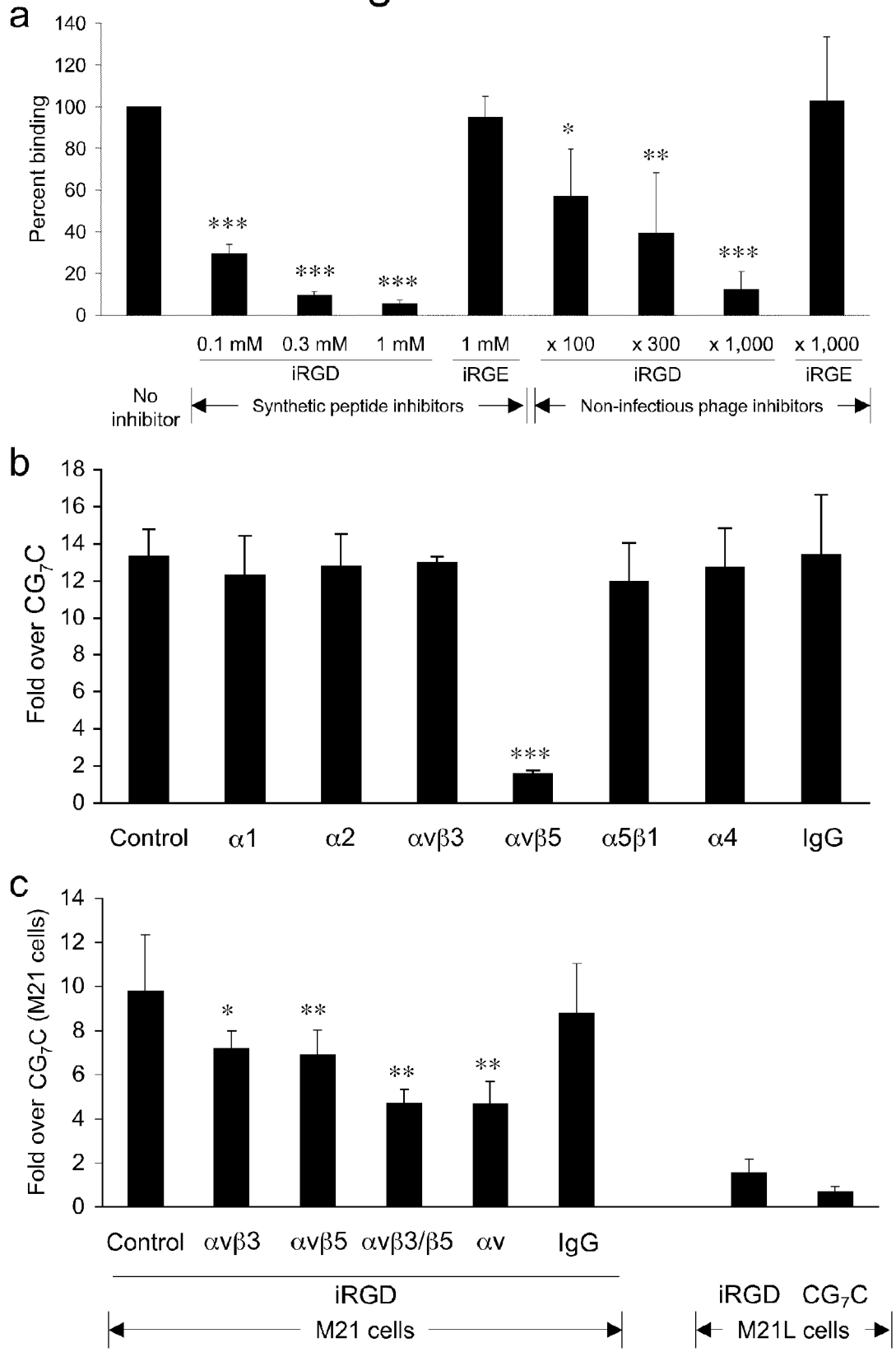
FIGS. 13A-13C show iRGD binds to αv integrins. a, Inhibition of iRGD phage binding to PPC1 prostate cancer cells by synthetic iRGD peptide and its variants, and corresponding non-infectious phage. b, c, Inhibition of iRGD phage binding to PPC1 cells (b) and M21 cells (c) by antibodies against integrins or control mouse IgG. Statistical analysis was performed with ANOVA (a, c) and Student's t-test (b).

Cultured prostate tumor cells bound iRGD phage at 4° C., but did not significantly internalize it, whereas both binding and internalization occurred at 37° C. (FIG. 18). The binding at 4° C. was inhibited in a dose-dependent manner by free iRGD peptide and by non-infectious (UV-inactivated) iRGD phage, but not by non-integrin-binding iRGE peptide or phage (FIG. 13A). The RGD-directed integrins αvβ3, αvβ5, and α5β1, are upregulated in angiogenic endothelial cells and certain tumor cells (Eliceiri and Cheresh (2001); Ruoslahti (2002)). PPC1 cells express αvβ5 and α5β1, but not αvβ3 (FIG. 19A). An anti-αvβ5 antibody almost completely inhibited iRGD phage binding to PPC1 cells, whereas inhibitory antibodies against αvβ3, α5β1, and several other integrins had no effect (FIG. 13B). M21 human melanoma cells (Cheresh and Spiro, Biosynthetic and functional properties of an Arg-Gly-Asp-directed receptor involved in human melanoma cell attachment to vitronectin, fibrinogen, and von Willebrand factor. *J. Biol. Chem.* 262, 17703-17711 (1987)) (FIG. 19B) that express both αvβ3 and αvβ5 bound iRGD, whereas variants lacking expression of these integrins did not, confirming the αv integrin dependency of iRGD binding (FIG. 13C). M21 cell binding was reduced by either anti-αvβ3 or anti-αvβ5 (FIG. 13C), indicating that iRGD recognizes both of these integrins.

Figure 14:
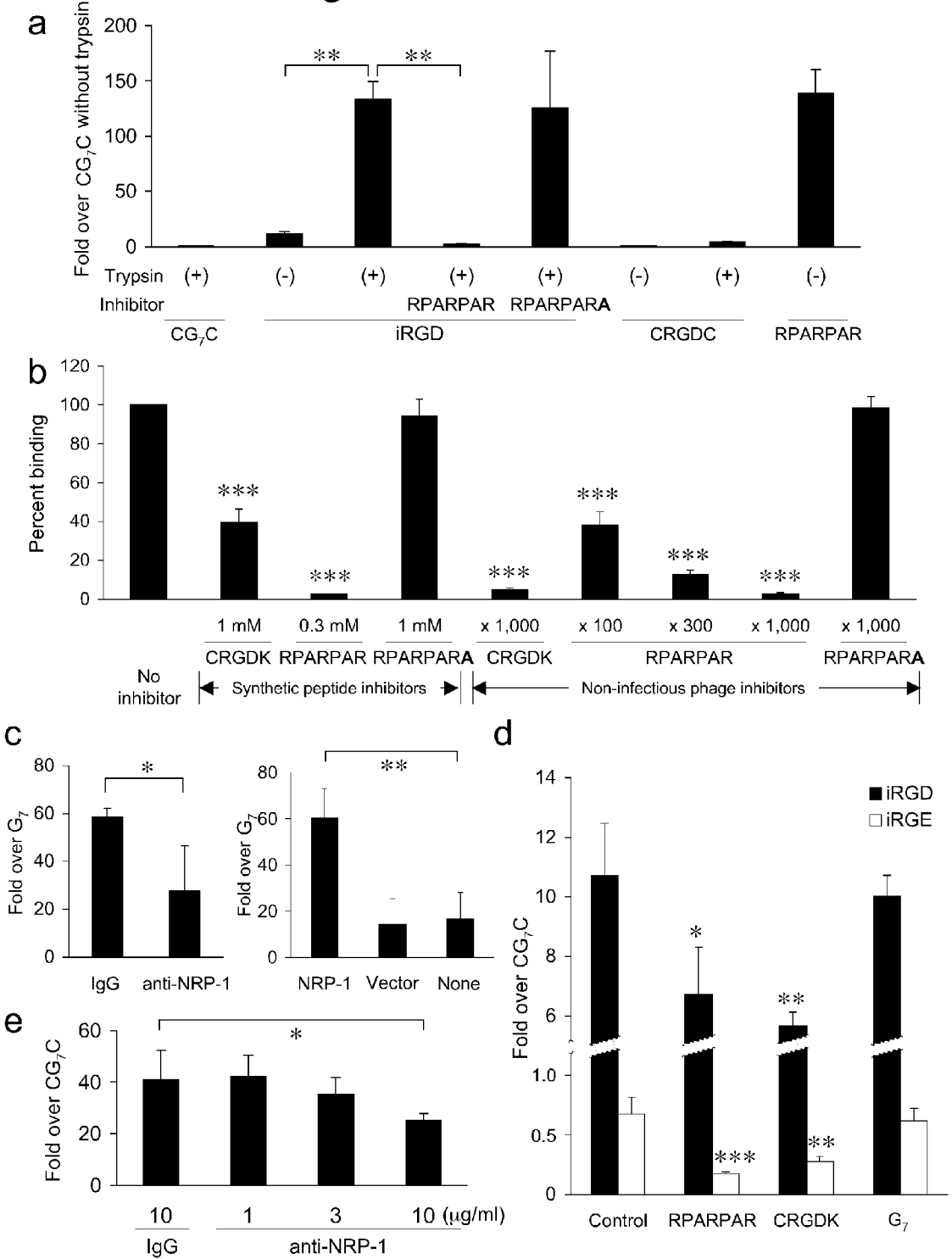

A consensus CendR motif, (R/K)XX(R/K) (SEQ ID NOs: 13, 14, 294, and 295), was shown to mediate neuropilin-1-dependent binding and internalization of peptides into cells. The motif is not active, unless it occupies a C-terminal position in the peptide. iRGD contains a CendR motif, RGDK/R, but this motif is not C-terminal. It was realized that proteolytic processing might be required to activate the CRGDK motif in iRGD. Indeed as shown in FIG. 14A, treatment of iRGD phage with trypsin, which cleaves proteins after arginine and lysine residues, enhanced the binding of iRGD phage to PPC1 cells. Trypsin had no effect on the non-internalizing peptides CRGDC (SEQ ID NO:292) or RGD-4C (SEQ ID NO:293) (not shown). The binding at 4° C. of the trypsin-treated iRGD phage, but not of intact iRGD phage (not shown), was blocked by non-infectious phage expressing a prototypic CendR peptide, RPARPAR (SEQ ID NO:296), but not by phage displaying a peptide in which the CendR motif was disrupted by addition of an alanine residue to the C-terminus (RPARPARA; SEQ ID NO:297).

To determine whether the CendR motif in iRGD is indeed activated by cellular proteases, FAM-iRGD (which carries FAM at its N-terminus) was incubated with PPC1 prostate cancer cells, and isolated intracellular products by affinity chromatography on anti-FITC antibodies. To prevent cytoplasmic proteolysis, while allowing proteolysis at the cell surface, the incubation was done in the presence of a proteasome inhibitor. No intracellular full-length FAM-iRGD was detected, the FAM-CRGDK fragment (SEQ ID NO:6) was recovered (FIG. 20).

Based on the implication that proteolytically released CRGDK (SEQ ID NO:6) is the active internalizing component of iRGD, phage expressing CRGDK (SEQ ID NO:6) was engineered and it was found that it bound to and was internalized within PPC1 cells. The binding process was not αv integrin-dependent (FIGS. 21A and 21B), but appeared to require the CendR system, as it was dose-dependently inhibited by RPARPAR (SEQ ID NO:296) phage (FIG. 14B). Moreover, an antibody against neuropilin-1, the receptor for CendR peptides, also reduced the binding (FIG. 14C, left panel). CRGDK (SEQ ID NO:6) phage did not substantially bind to or internalize into M21 cells with minimal expression of neuropilin-1 (FIG. 22), but forced expression of neuropilin-1 in these cells, increased the binding (FIG. 14C, right panel) and internalization (not shown) 3.5 fold. These results indicate that the CRGDK (SEQ ID NO:6) (as well as RPARPAR; SEQ ID NO:296) binds to cells and internalize following the CendR pathway.

Consistent with the RGDK CendR element (SEQ ID NO:11) being the internalizing sequence in iRGD, CRGDK (SEQ ID NO:6) and RPARPAR (SEQ ID NO:296) phage blocked iRGD phage internalization into PPC1 cells (FIG. 14D). Anti-neuropilin-1 also inhibited the internalization (FIG. 14E), but had little effect on binding of the phage to the cells (not shown). The relative roles of the RGD and RXXK motifs in iRGD was tested by using the iRGE phage, which does not bind to integrins due to the disrupted RGD motif (Pierschbacher and Ruoslahti (1984); Ruoslahti (2003)), but still contains a CendR motif, RXXK. The iRGE phage did internalize within PPC1 cells, and both RPARPAR (SEQ ID NO:296) and CRGDK (SEQ ID NO:6) inhibited the internalization (FIG. 14D), indicating that it follows the CendR internalization pathway. The internalization was far less effective than that of iRGD, presumably because iRGE lacks integrin binding that would concentrate the phage at the cell surface. These results show that iRGD internalizes within cells through the CendR pathway utilizing the RXXK sequence, and that the internalization is facilitated by initial binding to integrins through RGD.

Confocal microscopy showed that iRGD phage and neuropilin-1 co-localize in the perinuclear area and in the nuclei of cultured cells (FIG. 15A), supporting the involvement of the CendR pathway in the internalization of iRGD to tumor cells. Phage displaying an iRGD variant that lacks the CendR motif (CRGDGGPDC; SEQ ID NO:298), CRGDC (SEQ ID NO:292), or RGD-4C (SEQ ID NO:293) (FIG. 23) did not co-localize with neuropilin-1, nor did they internalize. After intravenous injection of FAM-iRGD peptide into mice bearing de novo PDACs (Bardeesy and DePinho, (2002)), the peptide initially co-localized with tumor vessels and then appeared within tumor cells positive for αv integrins (FIG. 15B, left panels). Importantly, tumor cells strongly positive for neuropilin-1 were particularly effective at accumulating and retaining FAM-iRGD (FIG. 15B, right panels).

These results delineate a novel multi-step targeting mechanism for iRGD; the intact peptide accumulates at the surface of cells expressing αv integrins, where it is proteolytically cleaved to produce the CendR motif-containing the CRGDK (SEQ ID NO:6) fragment. This fragment then binds to neuropilin-1 and is internalized within the target cells (FIG. 24). This mechanism makes iRGD special: it displays strong tumor specificity, is efficiently internalized within target cells, and penetrates into the tumor tissue. The multiple steps can each add to the tumor specificity of iRGD because the expression of αv integrins and neuropilin-1 is elevated in various tumor types (Eliceiri and Cheresh (2001); Ruoslahti (2002); Pellet-Many et al., Neuropilins: structure, function and role in disease. *Biochem. J.* 411, 211-226 (2008)). The same may be true of the processing protease(s). For example, matriptase, a membrane-bound protease, which preferentially cleaves proteins after a sequence similar to the (R/K) XX(R/K) CendR motif, is over-expressed in tumors (Uhland, Matriptase and its putative role in cancer. *Cell Mol. Life. Sci.* 63, 2968-2978 (2006)).

Integrins shuttle from the cell surface to intracellular compartments and back to the cell surface, and certain viral pathogens take advantage of this mechanism in entering into cells (Pellinen and Ivaska, Integrin traffic. *J. Cell Sci.* 119, 3723-3731 (2006)). However, the internalizing ability of iRGD, which requires the CendR pathway, is far more effective than that of conventional RGD peptides that follow the integrin trafficking The most remarkable result is the tissue-penetrating activity of iRGD which far exceeds what can be accomplished with conventional RGD peptides and their mimics, which only take their payload to tumor vessels (Murphy et al. (2008); Pasqualini et al., αv integrins as receptors for tumor targeting by circulating ligands. *Nature Biotechnol.* 15, 542-546 (1997)). This indicates that the CendR motif is important for penetration into the tumor interstitium, via mechanisms still to be elaborated.

Some previously described tumor-specific, cell-penetrating peptides contain cryptic CendR sequences (Hoffman et al. (2003); Laakkonen et al., A tumor-homing peptide with a targeting specificity related to lymphatic vessels. *Nature Med.* 8, 751-755 (2002); Porkka et al., A fragment of the HMGN2 protein homes to the nuclei of tumor cells and tumor endothelial cells in vivo. *Proc. Natl. Acad. Sci. USA* 99, 7444-7449 (2002); Joyce et al., Stage-specific vascular markers revealed by phage display in a mouse model of pancreatic islet tumorigenesis. *Cancer Cell* 4, 393-403 (2003)). LyP-1 (CGNKRTRGC; SEQ ID NO:299; Laakkonen et al. (2002)) is a 9-amino acid cyclic peptide with a binding site for a specific receptor (Fogal et al., Mitochondrial/cell-surface protein p32/gC1qR as a molecular target in tumor cells and tumor stroma. *Cancer Res.* 68, 7210-7218 (2008)) and a cryptic CendR motif, KRTR (amino acids 4-7 of SEQ ID NO:299). Like iRGD nanoparticles, LyP-1-coated nanoparticles extravasate into tumor tissue within minutes after an intravenous injection (Karmali et al. (2008); Laakkonen et al. (2002); von Maltzahn et al., In vivo tumor cell targeting with "click" nanoparticles. *Bioconjug. Chem.* 19, 1570-1578 (2008)). CendR involvement in the activities of LyP-1 and other homing peptides remains to be studied but seems likely. iRGD and the CendR system can be used to improve cancer targeting and treatment.

1. Methods

Mice were maintained in accordance with institutional guidelines and the animal experiments were approved by the Animal Research Committees at University of California, Santa Barbara and San Francisco. We used transgenic tumor mice (Bardeesy and DePinho, (2002); Arbeit et al., Progressive squamous epithelial neoplasia in K14-human papillomavirus type 16 transgenic mice. *J. Virol.* 68, 4358-4368 (1994); Hanahan, Heritable formation of pancreatic β-cell tumors in transgenic mice expressing recombinant insulin/simian virus 40 oncogenes. *Nature* 315, 115-122 (1985)) and xenograft tumors generated by injecting BALB/c nude mice (Harlan Sprague Dawley, Indianapolis, Ind.) with $10^6$ human cancer cells orthotopically, intracardiacly or into the brain and tibia. T7 phage expressing individual peptides (e.g., iRGE) were produced with T7-Select Phage Display System (EMD Biosciences, Gibbstown, N.J.) according to the manufacturer's instruction. Phage homing studies in vivo and cell binding studies in vitro (Zhang et al., (2006)), immunofluorescence (Karmali et al. (2008)) and flow cytometry (Sugahara et al., Hyaluronan oligosaccharides induce CD44 cleavage and promote cell migration in CD44-expressing tumor cells. *J. Biol. Chem.* 278, 32259-32265 (2003)) were done as described. Whole body imaging was performed 3 hrs after injecting the Cy7-labelled micelles with the Odyssey Infrared Imaging System (LI-COR Biosciences, Lincoln, Nebr.). In phage internalization assays, the cells were treated with $10^9$ plaque forming units (pfu) of phage for 1 hr at 37° C., washed with an acidic buffer (glycine-HCl, pH 2.5) to remove and inactivate phage bound to the cell surface, and lysed for phage titration. Peptide internalization was studied by incubating cells with 20 nM of FAM-labelled peptide for 90 min at 37° C. FAM-iRGD peptide internalized into PPC1 cells was recovered from acid-washed cells by anti-FITC affinity chromatography, and analyzed by mass spectrometry. To inhibit the binding and/or internalization of the phage, synthetic peptides or phage rendered non-infectious by UV-irradiation were added to the cells 20 min before incubation with the test phage. FAM-labelled peptides in tissues were quantified by measuring the fluorescence with Image J software. Student's t-test and one-way analysis of variance (ANOVA) followed by a suitable post hoc t-test were used for statistical analysis (Table 3).

TABLE 3

Statistical significance

| Figure | Method | p | Value § |
|---|---|---|---|
| 12B | t-test, 2 tailed | ** | p = 0.0028 |
| 12C | t-test, 2 tailed | ** | p = 0.0038 |
| 13A | one way ANOVA | *** | p < 0.0001 |
| | | *** | p < 0.0001 |
| | | *** | p < 0.0001 |
| | | * | p = 0.0298 |

TABLE 3-continued

Statistical significance

| Figure | Method | p | Value § |
|---|---|---|---|
| | | ** | p = 0.0059 |
| | | *** | p < 0.0001 |
| 13B | t-test, 2 tailed | *** | p < 0.0001 |
| 13C | one way ANOVA | * | p = 0.0458 |
| | | ** | p = 0.0030 |
| | | ** | p = 0.0012 |
| | | ** | p = 0.0012 |
| 14A | one way ANOVA | ** | p = 0.0018 |
| | | ** | p = 0.0027 |
| 14B | one way ANOVA | *** | p < 0.0001 |
| | | *** | p < 0.0001 |
| | | *** | p < 0.0001 |
| | | *** | p < 0.0001 |
| | | *** | p < 0.0001 |
| | | *** | p < 0.0001 |
| 14C | t-test, 2 tailed | * | p = 0.0237 |
| | | ** | p = 0.0027 |
| 14D | t-test, 2 tailed | * | p = 0.0403 |
| 14E | one way ANOVA | * | p = 0.0130 |
| | | *** | p = 0.0004 |
| | | ** | p = 0.0046 |
| | | ** | p = 0.0014 |
| 18 | t-test, 2 tailed | *** | p < 0.0001 |
| | | *** | p < 0.0001 |
| | | *** | p < 0.0001 |

§ The p values correspond to the asterisks from left to right in each figure; single asterisk, p < 0.05; double asterisk, p < 0.01; triple asterisk, p < 0.001.
† n = 3 for all statistical analyses.

i. Tumor Models

Xenografts were created by injecting BALB/c nude mice with $10^6$ human cancer cells orthotopically or into the tibia and brain: prostate cancers PC-3 (Yang et al., A fluorescent orthotopic bone metastasis model of human prostate cancer. *Cancer Res.* 59, 781-786 (1999)), PPC1 (Zhang et al., (2006)), and 22Rv-1 (Drake et al., Assessing tumor growth and distribution in a model of prostate cancer metastasis using bioluminescence imaging. *Clin. Exp. Metastasis* 22, 674-684 (2005)), pancreatic cancer MIA PaCa-2 (Sugahara et al., Chondroitin sulfate E fragments enhance CD44 cleavage and CD44-dependent motility in tumor cells. *Cancer Res.* 68, 7191-7199 (2008)), and breast cancer BT474 (Rusnak et al., The effects of the novel, reversible epidermal growth factor receptor/ErbB-2 tyrosine kinase inhibitor, GW2016, on the growth of human normal and tumor-derived cell lines in vitro and in vivo. *Mol. Cancer. Ther.* 1, 85-94 (2001)). Disseminated prostate tumors were generated by injecting $10^6$ GFP-PC-3 cells (Yang et al. (1999)) into the left ventricle of the heart. Tumors were monitored with the X-ray system of the Image Station In Vivo FX (Eastman Kodak Company, Rochster, N.Y.) or the Illumatool Bright Light System LT-9900 (Lightools Research, Encinitas, Calif.). Transgenic mice were maintained as described (Bardeesy and DePinho (2002); Arbeit et al. (1994); Hanahan (1985)).

ii. Screening of Phage Libraries

We used a cyclic $CX_7C$(C+cysteine; X=any amino acid) peptide library displayed on T7 phage (diversity approximately $10^9$) and a combination of ex vivo and in vivo screenings (Hoffman et al. (2003)). Bone xenografts of PPC1 and PC-3 (FIG. 25A) or disseminated bone tumors of GFP-PC-3 were used (FIG. 25B). Three rounds of ex vivo selection with tumor cell suspensions were followed by one in vivo selection for tumor homing. After a final ex vivo selection, the resulting phage pools bound to tumor-derived cell suspensions 200-400 times more than the original library, and 5 times more than to normal bone marrow-derived cells (FIG. 25C). Individual phage clones were randomly picked up from the phage pools and sequenced.

iii. In Vivo Peptide and Phage Homing

Synthetic peptides labelled with fluorescein (Karmali et al. (2008)) (approximately 200 µg) were intravenously injected into tumor-bearing mice and allowed to circulate for 15 min to 2 hrs. Tissues were collected and observed under UV light (Illumatool Bright Light System LT-9900) or processed for immunofluorescence (Karmali et al. (2008)). To assess phage homing (Zhang et al., (2006)), $10^9$ pfu of T7 phage were intravenously injected into tumor-bearing mice, and allowed to circulate for 15 min. The mice were perfused through the heart with PBS containing 1% BSA and tissues were harvested for immunofluorescence.

iv. Preparation of Micelles

Lipids were purchased from Avanti Polar Lipids (Alabaster, Ala.). $DSPE-PEG_{2,000}$-iRGD(FAM) was prepared by coupling FAM-iRGD peptide bearing a cysteine on its N-terminus to 1,2-distearoyl-sn-glycero-3-phosphoethanolamine-N-maleimide(polyethylene glycol)$_{2,000}$ ($DSPE-PEG_{2,000}$-maleimide) at 1:1 molar ratio at room temperature for 4 hrs. $DSPE-PEG_{2,000}$-FAM was prepared by coupling 1,2-distearoyl-sn-glycero-3-phosphoethanolamine-N-amino(polyethylene glycol)$_{2,000}$ ($DSPE-PEG_{2,000}$-amine) with NHS-Fluorescein (Pierce Biotechnology, Rockford, Ill.) at a 1:1 molar ratio for 1 hr at room temperature. $DSPE-PEG_{2,000}$-Cy7 was prepared similarly using 1,2-distearoyl-sn-glycero-3-phosphoethanolamine-N-amino(polyethylene glycol)$_{2,000}$ and Cy7-NHS ester (GE Healthcare, UK).

$DSPE-PEG_{2,000}$-iRGD(FAM), $DSPE-PEG_{2,000}$-amine, and $DSPE-PEG_{2,000}$-Cy7 in 3:6.7:0.3 molar ratios were dissolved in chloroform/methanol (3:1, v/v). The solvent was evaporated, and the dried lipid film was kept under vacuum for 8 hrs and allowed to swell in PBS for 2 hrs at 60° C. The vial was vortexed and sonicated to produce micelles. The micelles were sequentially filtered through 0.2 µm and 0.1 µm filters, and washed with sterile PBS to remove unreacted peptides. Control Cy7 micelles were prepared using $DSPE-PEG_{2,000}$-FAM in place of $DSPE-PEG_{2,000}$-iRGD(FAM). The micelles were 15-25 nm in diameter as measured in deionized water by dynamic laser light scattering (refractive index, 1.59; viscosity, 0.89) on a Malvern Zetasizer Nano (Malvern, UK). In vivo imaging of micelle-peptide conjugates PDAC mice (Bardeesy and DePinho, (2002)) were injected with 100 µl of 1 mM micelles in PBS. After 3 hrs, the mice were anesthetized, shaved, and subjected to whole body imaging with the Odyssey Infrared Imaging System (LI-COR Biosciences, Lincoln, Nebr.).

v. Immunofluorescence

Tissue sections were processed as described (Karmali et al. (2008)). Cells ($2 \times 10^5$ cells) were grown on collagen I-coated coverslips (BD Biosciences, San Jose, Calif.) overnight, and incubated with $10^8$ pfu/ml of T7 phage for 30 min. The cells were fixed in 4% paraformaldehyde, and stained with antibodies and DAPI (Molecular Probes, Eugene, Oreg.). The primary antibodies were rat anti-mouse CD31 monoclonal antibody (BD Biosciences), and rabbit anti-human αv integrin (Chemicon, Temecula, Calif.), rabbit anti-human neuropilin-1 (Chemicon), mouse anti-human neuropilin-1 (Miltenyi Biotec, Auburn, Calif.), and rabbit anti-T7 phage polyclonal antibodies. The secondary antibodies, Alexa594 goat antibodies to mouse, rat, and rabbit IgG and Alexa488 donkey anti-rabbit antibody were from Molecular Probes. Cells and tissue sections were examined by confocal microscopy (Fluoview 500, Olympus America, Center Valley, Pa.).

vi. In Vitro Phage Binding and Internalization Assays

Suspended cells ($10^6$ cells in DMEM containing 1% BSA) were incubated with $10^8$ pfu/ml of T7 phage for 1 hr at 4° C. The cells were washed 4 times with the binding buffer, lysed with lysogeny broth containing 1% NP-40, and titrated. Phage internalization assays used the same procedure, except that the cells were incubated with phage at 37° C., and that an acidic buffer (500 mM sodium chloride, 0.1 M glycine, 1% BSA, pH 2.5) was substituted for the binding buffer in the second wash Inhibitors of binding and internalization were added 20 min prior to incubation with phage. Non-infectious phage were prepared by treating phage with UV for 8 min in DMEM containing 1% BSA. The resulting UV-inactivated phage particles expressing about 200 peptides per particle were used as multivalent inhibitors. Free synthetic peptides, mouse antibodies against human α1, α2, αvβ3, αvβ5, α5β1, α4, or αv integrins and integrin subunits (Chemicon), goat anti-rat neuropilin-1 (R&D Systems, Minneapolis, Minn.), with mouse and a goat IgG isotype controls (Abcam) were also tested.

vii. Flow Cytometry

The experiments were performed as described (Sugahara et al., Hyaluronan oligosaccharides induce CD44 cleavage and promote cell migration in CD44-expressing tumor cells. *J. Biol. Chem.* 278, 32259-32265 (2003)) except that 1 mM of $MgSO_4$, $CaCl_2$, and $MnCl_2$ were added to the buffer. The antibodies were the same as in the cell binding assays, and were detected with Alexa488 goat anti-mouse antibody (Molecular Probes). The cells were analyzed with an EasyCyte Plus System (Guava Technologies, Hayward, Calif.).

viii. FAM-iRGD Fragment Isolation

PPC1 cells ($10^7$ cells in DMEM) were treated with 10 µM carbobenzoxyl-leucinyl-leucinyl-leucinal (MG132, EMD Chemicals, Gibbstown, N.J.) for 30 min at 37° C. to inhibit proteasomes, and incubated with 20 µM of iRGD peptide labelled with FAM at the N-terminus or C-terminus. The cells were washed once with acidic buffer and lysed in MPER (Pierce Biotechnology) containing protease inhibitors (Complete Mini EDTA-free, Roche Applied Science, Indianapolis, Ind.) on ice for 30 min. The sample was centrifuged for 30 min at 12,000 rpm. The supernatant was applied onto an anti-FITC affinity column, and after washing, bound peptides were eluted with glycine-HCl, pH 2.8. The eluate was subjected to mass spectrometry.

Throughout this application, various publications are referenced. The disclosures of these publications in their entireties are hereby incorporated by reference into this application in order to more fully describe the state of the art to which this invention pertains.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

REFERENCES

Arap, W., Pasqualini, R., and Ruoslahti, E. Cancer treatment by targeted drug delivery to tumor vasculature in a mouse model. Science 279:377-380 (1998).

Bardeesy, N. and DePinho, R. A. Pancreatic cancer biology and genetics. Nat Rev Cancer 2:897-909 (2002).

Eliceiri B P. and Cheresh D A. Adhesion events in angiogenesis. Current Opinion in Cell Biology. 13: 563-8 (2001)

Hoffman, J. A., Giraudo E., Singh, M., Inoue, M., Porkka, K., Hanahan' D., and Ruoslahti' E. Progressive vascular changes in a transgenic mouse model of squamous cell carcinoma. Cancer Cell 4:383-391 (2003).

Jarvinen T. and Ruoslahti E. Molecular changes in the vasculature of injured tissues. Am. J. Path. 171:702-711 (2007).

Joyce, J. A., Laakkonen P., Bernasconi, M., Bergers, G., Ruoslahti, E., and Hanahan, D. Stage-specific vascular markers revealed by phage display in a mouse model of pancreatic islet tumorigenesis. Cancer Cell 4:393-403 (2003).

Liu, C., Bhattacharjee, G., Boisvert, W., Dilley, R. and Edgington T. In vivo interrogation of the molecular display of atherosclerotic lesion surfaces. American Journal of Pathology 163:1859-71, 2003.

Pilch, J., Brown, D. M., Komatsu, M., Jarvinen, T., Yang, M., Peters, D., Hoffman, R. M., and Ruoslahti, E. Peptides selected for binding to clotted plasma accumulate in tumor stroma and wounds. Proc. Natl. Acad. Sci. USA. 103: 2800-2804 (2006)

Ruoslahti, E. Specialization of tumour vasculature. Nature Reviews Cancer 2: 83-90 (2002).

Ruoslahti, E. Drug targeting to specific vascular sites. Drug Discovery Today. 7:1138-1143 (2002).

Ruoslahti, E. RGD story: a personal account. A Landmark Essay. Matrix Biology. 22: 459-465 (2003).

Ruoslahti, E. Vascular zipcodes in angiogenesis and metastasis. Biochem Soc Transact 32: 397-402 (2004).

Ruoslahti, E., Duza, T., and Zhang, L. Vascular homing peptides with cell-penetrating properties. Current Pharmaceutical Design. Special Issue: Cell-penetrating Peptides, Mechanisms and Applications. Executive Editor: Ulo Langel. 11:3655-3660, (2005).

Simberg, D., Duza T., Park, J. H., Essler M., Pilch, J., Zhang, L., Derfus A. M., Yang M., Hoffman R. M., Bhatia, S., Sailor, M. J. and Ruoslahti, E. Biomimetic amplification of nanoparticle homing to tumors. Proc. Natl. Acad. Sci. USA 104: 932-936 (2007).

Thomas, G. Furin at the cutting edge: From protein traffic to embryogenesis and disease. Nat Rev Mol Cell Biol 3: 753-766 (2002).

What is claimed is:

1. An isolated peptide comprising an amino acid segment comprising the amino acid sequence of SEQ ID NO: 1, SEQ ID NO: 2, SEQ ID NO: 3, SEQ ID NO:290, one of the amino acid sequences CRGD(R/K/H)GV(D/E/H)C (SEQ ID NO:329), or one of the amino acid sequences CRGDHGP(D/E/H)C (SEQ ID NO:330).

2. The isolated peptide of claim 1, wherein the peptide has a length of less than 100 residues.

3. The isolated peptide of claim 1, wherein the peptide has a length of less than 50 residues.

4. The isolated peptide of claim 1, wherein the peptide has a length of less than 20 residues.

5. The isolated peptide of claim 1, wherein the amino acid segment is cyclic.

6. The isolated peptide of claim 5, wherein the amino acid segment is cyclized via a disulfide bond.

7. The isolated peptide of claim 1, wherein the peptide selectively homes to a site of angiogenesis.

8. The isolated peptide of claim 7, wherein the angiogenesis is at a site of injury.

9. The isolated peptide of claim 7, wherein the angiogenesis is at a surgical site.

10. The isolated peptide of claim 1, wherein the peptide selectively homes to a tumor.

11. The isolated peptide of claim 1, wherein the peptide selectively homes to a site of arthritis.

12. The isolated peptide of claim 1, wherein the peptide selectively homes to a cell or tissue expressing one or more αv integrins.

13. The isolated peptide of claim 1, wherein the peptide selectively homes to a cell or tissue expressing one or more αv integrins and neuropilin-1.

14. The isolated peptide of claim 1, wherein the peptide consists of the amino acid segment.

15. A conjugate, wherein the conjugate comprises a moiety linked to the peptide of claim 1.

16. The conjugate of claim 15, wherein the moiety is a an anti-angiogenic agent, a pro-angiogenic agent, a cancer chemotherapeutic agent, a cytotoxic agent, an anti-inflammatory agent, an anti-arthritic agent, a nanoparticle, a polypeptide, a nucleic acid molecule, a small molecule, a fluorophore, fluorescein, rhodamine, a radionuclide, indium-111, technetium-99, carbon-11, carbon-13, or a combination.

17. The conjugate of claim 16, wherein the moiety is a therapeutic agent.

18. The conjugate of claim 17, wherein the therapeutic agent is decorin.

19. The conjugate of claim 16, wherein the moiety is a detectable agent.

20. The conjugate of claim 16, wherein the conjugate comprises a virus.

21. The conjugate of claim 20, wherein the conjugate comprises a phage.

\* \* \* \* \*

UNITED STATES PATENT AND TRADEMARK OFFICE
CERTIFICATE OF CORRECTION

PATENT NO. : 8,367,621 B2
APPLICATION NO. : 12/355672
DATED : February 5, 2013
INVENTOR(S) : Erkki Ruoslahti, Tambet Teesalu and Kazuki Sugahara It is certified that error appears in the above-identified patent and that said Letters Patent is hereby corrected as shown below:

In the Specification

Column 1, Lines 15-19, replace the following paragraph:
"This invention was made with government Support under grants CA104898, CA 119414, CA 119335, CA124427, CA115410, and 30199 from the National Cancer Institute of the NIH and grant BC 076050 from the Department of Defense. The government has certain rights in the invention."

With the following paragraph:
--This invention was made with government support under CA115410, CA119414, CA030199, CA119335, CA104898, CA124427, and DK076050 awarded by the National Institutes of Health. The government has certain rights in the invention.--

Signed and Sealed this
Twenty-second Day of August, 2023

Katherine Kelly Vidal
Katherine Kelly Vidal
*Director of the United States Patent and Trademark Office*